US010002230B2

(12) United States Patent
Courchesne et al.

(10) Patent No.: US 10,002,230 B2
(45) Date of Patent: Jun. 19, 2018

(54) SCREENING, DIAGNOSIS AND PROGNOSIS OF AUTISM AND OTHER DEVELOPMENTAL DISORDERS

(71) Applicant: The Regents of the University of California, Oakland, CA (US)

(72) Inventors: Eric Courchesne, San Diego, CA (US); Tiziano Pramparo, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 219 days.

(21) Appl. No.: 14/604,834

(22) Filed: Jan. 26, 2015

(65) Prior Publication Data

US 2015/0227681 A1 Aug. 13, 2015

Related U.S. Application Data

(63) Continuation of application No. PCT/US2013/052094, filed on Jul. 25, 2013.

(60) Provisional application No. 61/675,928, filed on Jul. 26, 2012.

(51) Int. Cl.

| | |
|---|---|
| ***G06F 19/20*** | (2011.01) |
| ***C12Q 1/68*** | (2018.01) |

(52) U.S. Cl.

CPC .......... *G06F 19/20* (2013.01); *C12Q 1/6883* (2013.01); *G16H 50/20* (2018.01); *C12Q 2600/158* (2013.01); *G01N 2800/28* (2013.01)

(58) Field of Classification Search

None

See application file for complete search history.

(56) References Cited

U.S. PATENT DOCUMENTS

| | | | |
|---|---|---|---|
| 8,173,369 | B2 | 5/2012 | Geschwind et al. |
| 2003/0017481 | A1 | 1/2003 | Golub et al. |

FOREIGN PATENT DOCUMENTS

| | | | |
|---|---|---|---|
| JP | 2008-011744 | A | 1/2008 |
| WO | 2010/147714 | A1 | 12/2010 |
| WO | 2011/079299 | A1 | 6/2011 |
| WO | 2011/109440 | A1 | 9/2011 |
| WO | 2011/112961 | A1 | 9/2011 |
| WO | 2011/138429 | A1 | 11/2011 |

OTHER PUBLICATIONS

Fuller et al. "Chapter 18 Review of Weighted Gene Coexpression Network Analysis", Handbook of Statistical Bioinformatics, H. Horng-Shing Lu et al. (eds.), Springer 2011, p. 369-388.*

PCT International Search Report and Written Opinion for PCT Application No. PCT/US2013/052094 dated Oct. 16, 2013 (12 pages).

Supplementary European Search Report for EP Application No. 13823113.9 dated Jan. 28, 2016 (10 pages).

Chow et al., "Age-Dependent Brain Gene Expression and Copy Number Anomalies in Autism Suggest Distinct Pathological Processes at Young Versus Mature Ages," PLoS Genetics, 2012, 8(3):1-14.

Diaz-Uriarte, "Molecular Signatures from Gene Expression Data," http://ligarto.org/rdiaz/Papers/signatures-tech-report.pdf, 2004, pp. 1-22.

Kuwano et al., "Autism-Associated Gene Expression in Peripheral Leucocytes Commonly Observed between Subjects with Autism and Healthy Women Having Autistic Children," PLoS One, 2011, 6(9):1-12.

Voineagu et al., "Transcriptomic Analysis of Autistic Brain Reveals Convergent Molecular Pathology," Nature, 2011, 474:380-386.

Xu et al., "AutismKB: An Evidence-Based Knowledgebase of Autism Genetics," Nucleic Acids Research, 2012, 40: D1016-D1022.

* cited by examiner

*Primary Examiner* — John S. Brusca

*Assistant Examiner* — Olivia M Wise

(74) *Attorney, Agent, or Firm* — Eversheds Sutherland (US) LLP

(57) ABSTRACT

The invention provides a method and system combining functional genomic and genetic, proteomic, anatomic neuroimaging, functional neuroimaging, behavioral and clinical measurements and data analyses for autism pediatric population screening, diagnosis or prognosis. More specifically, the invention provides a weighted gene and feature test for autism which uses a weighted gene signature matrix for comparison to a reference database of healthy and afflicted individuals. The invention also provides normalized gene expression value signatures for comparison to a reference database. The invention additionally combines either the weighted gene or the normalized gene analysis with comparisons to a gene-networks signature matrix, a multi-modal signature matrix, and a collateral features signature matrix for improved accuracy in screening, diagnostic and prognostic relevance for autism, particularly for newborns, babies ages birth to 1 year, toddlers ages 1 to 2 years, toddlers ages 2 to 3 years and young children ages 3 through 4 years.

10 Claims, 24 Drawing Sheets

| | DISCOVERY | REPLICATION | ASD VS. TD | ASD VS. CONTRAST | CONTRAST VS.TD |
|---|---|---|---|---|---|
| | *ROC 1* | *ROC 2* | *ROC 3* | *ROC 4* | *ROC 5* |
| # SUBJECTS | 142 | 73 | 197 | 149 | 84 |
| BEST THRESHOLD | 0.559 | 0.547 | 0.547 | 0.614 | 0.547 |
| TRUE POSITIVE | 74 | 34 | 108 | 94 | 8 |
| TRUE NEGATIVE | 44 | 21 | 53 | 14 | 53 |
| FALSE POSITIVE | 11 | 8 | 13 | 4 | 13 |
| FALSE NEGATIVE | 13 | 10 | 23 | 37 | 10 |
| ACCURACY (%) | 82.53 | 74.84 | 81.37 | 74.77 | 62.37 |
| SPECIFICITY (%) | 80 | 72.41 | 80.3 | 77.77 | 80.3 |
| SENSITIVITY (%) | 85.05 | 77.27 | 82.44 | 71.75 | 44.44 |

| | L_CB_GM | L_CB_WM | R_CB_GM | R_CB_WM | L_CBLL_GM | L_CBLL_WM | R_CBLL_GM | R_CBLL_WM | BS | TBV | LhemiSA | RhemiSA |
|---|---|---|---|---|---|---|---|---|---|---|---|---|
| MEGREEN YELLOW | 0.25 (0.02) | 0.16 (0.1) | 0.25 (0.02) | 0.17 (0.1) | -0.00038 (1) | -0.038 (0.7) | 0.037 (0.7) | 0.038 (0.7) | 0.1 (0.3) | 0.23 (0.03) | 0.22 (0.04) | 0.21 (0.04) |
| MEMIDNIGHT BLUE | 0.0082 (0.9) | -0.051 (0.6) | 0.0034 (1) | -0.038 (0.7) | -0.068 (0.5) | -0.029 (0.8) | -0.097 (0.4) | -0.0015 (1) | -0.045 (0.7) | -0.026 (0.8) | 0.014 (0.9) | 0.0088 (0.9) |
| METURQUOISE | 0.076 (0.5) | -0.036 (0.7) | 0.054 (0.6) | -0.028 (0.8) | 0.12 (0.3) | 0.03 (0.8) | 0.042 (0.7) | 0.066 (0.5) | 0.00062 (1) | 0.033 (0.8) | 0.055 (0.6) | 0.063 (0.6 |
| MEDARKGREEN | -0.22 (0.04) | -0.19 (0.08) | -0.19 (0.08) | -0.19 (0.08) | -0.11 (0.3) | 0.0037 (1) | -0.09 (0.4) | -0.045 (0.7) | -0.31 (0.003) | -0.22 (0.04) | -0.17 (0.1) | -0.19 (0.07) |
| MEGREY60 | -0.21 (0.05) | -0.19 (0.08) | -0.21 (0.05) | -0.2 (0.06) | 0.039 (0.7) | 0.093 (0.4) | -0.085 (0.4) | 0.003 (1) | -0.18 (0.09) | -0.22 (0.04) | -0.2 (0.06) | -0.18 (0.1) |
| MEBLACK | -0.27 (0.01) | -0.21 (0.05) | -0.27 (0.01) | -0.22 (0.04) | 0.023 (0.8) | 0.073 (0.5) | -0.058 (0.6) | -0.005 (1) | -0.14 (0.2) | -0.26 (0.01) | -0.25 (0.02) | -0.24 (0.02) |
| MEBLUE | -0.23 (0.03) | -0.14 (0.2) | -0.21 (0.05) | -0.15 (0.2) | -0.044 (0.7) | 0.015 (0.9) | -0.054 (0.6) | -0.056 (0.6) | -0.083 (0.4) | -0.2 (0.06) | -0.21 (0.05) | -0.21 (0.05) |
| MELIGHT YELLOW | -0.17 (0.1) | -0.15 (0.2) | -0.2 (0.06) | -0.14 (0.2) | -0.11 (0.3) | -0.11 (0.3) | -0.16 (0.1) | -0.1 (0.3) | -0.16 (0.1) | -0.19 (0.08) | -0.11 (0.3) | -0.14 (0.2) |
| MEPURPLE | -0.26 (0.01) | -0.25 (0.02) | -0.27 (0.01) | -0.23 (0.03) | 0.18 (0.09) | -0.066 (0.5) | 0.018 (0.9) | -0.068 (0.5) | -0.026 (0.8) | -0.25 (0.02) | -0.25 (0.02) | -0.23 (0.03) |
| MEROYALBLUE | -0.26 (0.02) | -0.15 (0.2) | -0.26 (0.01) | -0.13 (0.2) | 0.12 (0.3) | -0.029 (0.8) | -0.069 (0.5) | -0.13 (0.2) | -0.054 (0.6) | -0.21 (0.05) | -0.19 (0.07) | -0.18 (0.09) |
| MEGREY | -0.3 (0.005) | -0.22 (0.04) | -0.29 (0.007) | -0.22 (0.04) | -0.098 (0.4) | 0.063 (0.6) | -0.2 (0.07) | -0.05 (0.6) | -0.22 (0.04) | -0.29 (0.005) | -0.29 (0.006) | -0.28 (0.008) |

SCREENING, DIAGNOSIS AND PROGNOSIS OF AUTISM AND OTHER DEVELOPMENTAL DISORDERS

CROSS-REFERENCE TO RELATED APPLICATIONS

This application is a continuation of PCT Application No. PCT/US2013/052094 filed Jul. 25, 2013, which claims priority to U.S. Provisional Application No. 61/675,928, filed Jul. 26, 2012, the entire contents of which are incorporated by reference herewith.

STATEMENT REGARDING FEDERALLY SPONSORED RESEARCH

This invention was made with government support under grant Nos. P50-MH081755, R01-MH080134, and R01-MH036840 awarded by National Institute of Mental Health (NIMH). The government has certain rights in the invention.

FIELD OF THE INVENTION

The invention relates generally to screening, diagnosis and prognosis of autism and other development disorders. More specifically, the invention relates to the use of a combination of functional genomic signatures and multimodality signatures in screening for autism risk and in autism diagnostics and prognostics. Its prognostics use includes prediction and characterization of likely clinical, neural and treatment progress and outcome.

BACKGROUND OF THE INVENTION

It is of the greatest importance to improve early screening and detection of risk for autism, a genetically complex neural developmental disorder affecting higher order functions such as social, communication, language and cognition. Among the benefits of early detection is that accelerating the pace of identification and treatment by even a year[1] can have a considerable impact on the outcome of affected newborns, infants, toddlers and young children.

Despite recent university-based research advances in the development of potential methods for screening, detection and diagnostic evaluation for autism within the first 2 years of life, the clinical translation of these methods into widespread and effective community practice in the US has not occurred. Instead, 3 to 5 years of age continues to be the age of first clinical identification and referral for treatment services for autism in much of the US[1]. Studies find that on average, a child with autism is diagnostically evaluated by 4 to 5 different professionals before a final diagnosis is determined and this process can take several years during which the child does not receive suitable treatment. From a neurobiological perspective, this is particularly problematic given that functional connections in the brain are strongly established during the first few years of life[2, 3]. Starting treatment after many neural connections have already been formed (rather than before) will likely reduce treatment efficacy and impact. Hundreds of websites, articles, blogs and government, professional and private organizations cite the need for the early screening, detection, diagnosis and treatment referral for children with autism, yet the gulf separating university-based research advances in early detection and actual community clinical practice is alarming; For example, in 2012 the CDC documented the median age of autism identification in the US (based on 2008 data) is about 4 years[1]. The median age of treatment referral is correspondingly even later in the US. Further, there remain large underserved segments of the population, both in terms of early screening and access to empirically-validated early intervention. The magnitude of the problem is staggering: Given recent prevalence estimates and the U.S. birth rate, every year 52,000 to 84,000 infants will go on to develop autism. Thus, there is an enormous and urgent need for useful and cost-effective pediatric population screening strategies in ordinary community settings throughout the U.S. Presently, unfortunately, hundreds of thousands of toddlers and young children with autism in the U.S. are overlooked, under-treated and may have a poorer outcome than need be.

Moreover, once children are identified with having an autism spectrum disorder (ASD), science has not yet offered insight into prognosis. Will the child face consistent extreme barriers in speech, language and social development, or will he or she fall into the minority of ASD individuals that enjoy success in school and beyond. Presently, however, there are no prognostic biomarkers of autism; specifically there is a lack of prognostic biomarkers that predict and characterize likely clinical, neural and treatment progress and outcome.

Despite the importance, the high priority of discovery of risk behavioral or biological markers with clinical impact remains largely unfulfilled. Neither biological nor behavioral markers have emerged that fulfill this need in clinical settings for the general pediatric population. For example, commonly used parent report screens (e.g., Modified Checklist for Autism in Toddlers (M-CHAT), Communication and Symbolic Behavior Scales (CSBS) have valuable strengths, but also weaknesses[4-6], including very high false positive rates. The M-CHAT has very low specificity (27%[5]) and positive predictive value (PPV, 11%) when used in the general population[7], rendering it of limited utility in routine clinical practice. Similarly, the newest and largest study to test the efficacy of the M-CHAT conducted by Chlebowski, Robins, Barton & Fein published in 2013 found an 80% false positive rate when the tool was used alone[8]. Although high-risk baby sib studies by Zwaigenbaum[9], Ozonoff[10], Paul[11], Landa[12] and others have revealed key early deficits such as abnormalities in social attention[9], they report data only at the group level and have not reported validation statistics such as PPV that are a necessary first step for determining the utility of a behavioral trait as an early marker.

Several groups have used eye tracking and reported reduced preference for biological motion[23], fixation to the eye region[24], head region[25] and difficulties in joint attention[26] as well as scene monitoring during explicit dyadic cues[27] in ASD relative to typically developing (TD) toddlers. While collectively these studies point to early developmental origins of social dysfunction, reported effects are subtle and results are provided only at the overall group level and have very weak power to detect or diagnose ASD. For example, in one study differences in fixation towards the face and eye region were no different between ASD and TD toddlers when toddlers watched a woman make a sandwich and only became evident during a specific 3-second dyadic bid condition[27]. Moreover, validation statistics that are needed to translate eye tracking into a screening tool, such as specificity or positive predictive value, are not provided in most eye tracking studies of ASD toddlers.

While great strides have been made in understanding possible genetic risk factors[13-15] and neural bases[16-18] of autism, neither gene nor brain abnormalities published to date have translated into practical clinical population screens or tests of risk for autism in toddlers. Also, links between genetic and neural developmental abnormalities at young ages have remained largely unknown. Overall, research on potential genetic and neuroimaging biomarkers has remained largely "in the lab."

Discovery by one of the present inventors[19] that a substantial percentage of autism infants and toddlers display early brain overgrowth indicates that autism might involve abnormalities in mechanisms that regulate cell production or natural apoptosis in early life. The inventor analyzed dysregulation of genetic mechanism in autism in two ways. First, the total number of neurons in prefrontal cortex tissue in postmortem autistic boys was counted to reveal a huge 67% excess of neurons[18]. Second, evidence shows that dysregulation of genetic mechanism that govern neuron number in prefrontal cortex brain tissue in postmortem autistic boys[14].

These discoveries have advanced the general understanding of the neural and genetic bases of ASD but not the early screening of ASD risk, diagnostic evaluation, and prognostic assessment of autism at the level of the individual child in the general pediatric population. While other studies raise the hope that MRI neuro-imaging biomarkers might be identified for use with older children or adults already known to have autism, they have not demonstrated the ability to improve risk assessment at very young ages in the general pediatric population when they are most needed. Still other studies suffer from limitations such as being based only on data from multiplex ASD families[18,19] leaving unaddressed the majority of autistic infants in the general population, or based on algorithms that identify genes with little or no demonstrated relevance to the underlying brain maldevelopment in autism[20,21].

Broadly speaking, "biomarkers" to date (e.g., genetic, molecular, imaging) have poor diagnostic accuracy, specificity and/or sensitivity; none have clinical outcome prognostic power; most are expensive; none are suitable as an early screening tool in community populations; and few have undergone serious clinical scrutiny and rigorous validation. For example, genetic findings have been generally non-specific, and the best characterized CNVs can occur in schizophrenia, bipolar, intellectual disability as well as ASD (e.g., 16p11.2). Few gene mutations are recurrent[22]. CNVs and recurrent genes combined account for a very small, arguably about 5-10%, of all ASD individuals. Thus, current DNA tests detect only rare autism cases and lack specificity. Moreover, genetic tests released by several companies detect only a small percent (5% to 20%) of ASD individuals, generally lack good specificity (because CNV, gene mutation and SNP markers in these tests are also found in a wide variety of non-ASD disorders such as schizophrenia or bipolar as well as in non-symptomatic, "typical" individuals), miss the vast majority of ASD individuals and are very expensive and out of the reach of most individuals. A genetic test targeting baby sibs of older ASD children provides only estimates of risk from less to more, but of course, parents who already have a child with ASD already know subsequent offspring are at risk. The benefit from this test is arguably small and of little practical clinical utility. No genetic finding has been shown to have clinical outcome prognostic power; that is, genetic testing does not provide information about likely later language, social or general functional progress and ability. A recent MRI "biomarker" works on adults with ASD, but diagnosis of ASD in adults is of very limited clinical value. A diffusion tensor imaging (DTI) study of small samples of infant siblings of older ASD children shows group differences too small to hold diagnostic promise. A gene expression classifier of previously diagnosed ASD 5 to 11 year olds performed in a validation set with accuracy, sensitivity and specificity at only 67.7%, 69.2% and 65.9%, respectively[21]. A metabolomics classifier tested only a sample of 4 to 6.9 year old children previously diagnosed as ASD and did not test newborns or 0 up to 4 year olds.[32]

In sum, no currently reported biomarker holds promise as a primary or secondary early developmental screen or an early diagnostic or prognostic tool in ordinary community pediatric settings at young ages from birth through early childhood when these clinical tools are most needed. There are no preclinical screens or tests for risk of developing ASD with the sensitivity and specificity for routine value in clinical application. Current expectations are that ASD is so etiologically and clinically heterogeneous that no diagnostic biomarker and/or combination of behavioral or biological markers is likely to do better that detect a small percentage of cases, and that such biomarkers and/or combination of behavioral and biological markers will be either sensitive but non-specific or specific but for a tiny portion of the ASD spectrum.

SUMMARY OF THE INVENTION

The invention provides a leap beyond all current early screening, diagnostic and prognostic biomarker tests for ASD. In certain embodiments, the invention is unique because, among other advantages provided, it is the only approach utilizing multimodality (functional genomic, genetic, proteomic, anatomic neuroimaging, functional neuroimaging, and neurobehavioral) data combined with deep clinical phenotyping data all from the same individual infants and toddlers representative of the general community pediatric population. Using complex bioinformatics methods in novel ways, the invention provides novel single and multimodality signatures of ASD.

In certain embodiments, the invention is unique in the identification of genes, and gene-to-gene interactions (e.g., gene pathways, gene networks, and hub-gene activity patterns and organization including quantifiable signature features) in combination with clinical, neuroimaging and behavioral information that have high accuracy, specificity and sensitivity for early screening, diagnostic evaluation and prognostic assessment for autism of subjects including particularly those at ages from birth to 1 year, 1 year to 2 years, 2 years to 3 years, and 3 years to 4 years, and older.

The invention provides highly surprising advantages for multiple reasons: ASD is thought to be highly etiologically and clinically heterogeneous, and yet the invention in certain embodiments can accurately detect the great majority (such as at least 82%) of cases, not just a small percentage of cases (which is the best other ASD risk current biological and behavioral tests can do). There is no proven preclinical marker of ASD, and yet the invention can detect ASD with high accuracy, sensitivity and specificity before clinical symptom onset in the general natural pediatric population (not just in cases already suspected of being at high risk because of an older sibling with ASD, dysmorphology, seizure, etc). By comparison, existent genetic tests have low specificity as well as poor sensitivity, detecting only 5% to 20% of ASD cases when tested in general preclinical pediatric populations. Claims of prior art are exaggerated because they are based on tests performed on patients already highly suspected of being ASD because of prior clinical testing. The invention has surprisingly high accuracy, sensitivity and specificity in the natural pediatric setting where early screening is a major unfilled need. No prior art has discovered how to utilize clinical and neurobehavior information to differentially adjust genomic signatures so that they are tuned for the different uses in general population screening, diagnostic evaluation and prognostic assessment.

In certain embodiments, for screening, weighted gene expression patterns can be used alone or in combination with readily available standard clinical measures (head circumference, age, CSBS scores, and GeoPrefernce test score) and do not depend on neuroimaging or other tools unsuited to general population screening, while for that diagnostic or prognostic use after a child has become suspected of being at risk, weighted gene expression patterns can be used in combination with specialty tools such as MRI or fMRI to optimize diagnostic and prognostic judgments. No prior screening, diagnostic and prognostic prior art using biological measures is able to accurately classify the great majority of ASD cases at such young ages. In sum, no currently available method matches the present invention for providing a combination of effectiveness across the youngest ages from birth to childhood; complex algorithmic use of gene weights, patterns and pathways in combination with clinical and neurobehavioral variables; high accuracy, specificity and sensitivity; and flexible utility in autism screening, diagnostic evaluation and prognostic assessment.

In certain embodiments, the invention provides methods of conducting a weighted gene and feature test of autism (WGFTA) for autism screening, diagnosis or prognosis. The method can include a) obtaining an analyte from a biological sample to obtain analyte-associated gene expression levels of a set of at least 20 or more genes selected from a model derived from an autism reference database, such as disclosed in Tables 1 and 2; b) statistically normalizing each expression level of the selected set of genes expressed to derive a normalized gene expression value (NGEV) for each gene in the selected set of the subject; c) preparing a weighted gene signature matrix (WGSM) of the selected gene set; d) calculating a weighted gene expression level of each gene in the selected set by multiplying the NGEV for each gene by a gene-specific weight of that gene. Gene-weights are derived from a computer-based bioinformatic analysis of the relative expression levels of at least the selected set of genes from the autism reference database including in certain embodiments at least 40 healthy individuals and 40 autistic individuals compiled in a weighted gene expression reference database (WGERD); and e) establishing the divergence of the set of each weighted gene expression level of the subject to the weighted gene expression reference database (WGERD), to thereby conduct WGFTA to indicate increasing correlation with autism risk, diagnosis or prognosis.

Genes that can be tested by the inventive method include those shown in Tables 1 and 2 and 16-25 herein. The genes can be selected based on their weighted relevance to diagosis or prognosis. These genes involve cell cycle, protein folding, cell adhesion, translation, DNA damage response, apoptosis, immune/inflammation functions, signal transduction ESR1-nuclear pathway, transcription-mRNA processing, cell cycle meiosis, cell cycle G2-M, cell cycle mitosis, cytoskeleton-spindle microtubule, and cytoskeleton-cytoplasmic microtubule functions. In certain embodiments, genes tested by the inventive method are involved in DNA-damage or mitogenic signaling in brain development.

In certain embodiments, the inventive method can use as few as 20 and include about 4000 Autism WSGM genes (including specific splice variants among these genes) which may be contained within as few as a single gene set or as many as 8 gene sets and subsets. Different sets and subsets can be used to optimize performance under different assay and application circumstances. In certain embodiments, genes are selected from at least 2, 10, 20, 25, 30, 35, 40, 45, 50, 55, 60, 70, 80, 160, 320, 640, 762, or any number in between, for example, from the genes in Table 1. Table 1 represents genes in the present methods for selection based on the highest weight ranking which are more frequently associated with ASD diagnosis. The genes may be arranged and selected from among 4 sets as shown in Table 1, depending upon the commonality of their expression patterns. The top 50 genes with absolute value of weights ranging from about 0.50-1.00 in sets 1-4 are also listed in Tables 1.1, 1.2, 1.3, and 1.4.

In other embodiments, genes are selected from at least 2, 10, 20, 25, 30, 35, 40, 45, 50, 55, 60, 70, 80, 100, 120, 150, 200, 250, 300, 400, 500, 600, 700, 800, 900, 1000, 1500, 2000, 2500, or more genes in the gene listings as shown in Tables 16 through 25 provided below. In certain embodiments, the genes are unique differentially expressed (DE) genes found in ASD and control toddlers. These genes are for instance, dysregulated in DNA-damage response, mitogenic signaling, and cell number regulation.

In certain embodiments, normalized gene expression values of the signature genes (e.g., Tables 1 and 1.1-1.4) can be used as is, thus without weighting, for the classification of ASD vs non-ASD. In certain embodiments, using Boosting (see Scoring and Classification methods) three lists of genes were identified with the smallest number of elements that classified subjects with accuracy of at least 70%, 75%, 80%, 85%, 90%, 95%, 96%, 97%, 98%, 99%, or 100%. Sets with 20, 25 and 30 features that can produce at least 70%, at least 75%, and at least 80% correct classification include but are not limited to those shown in Table 2 below. In certain embodiments, adjusting the weights of the genes based on the age of the subject is the most important single parameter for improving accuracy of ASD classification.

The invention claims the use of gene-weights and optionally, feature signatures as defined below for each of the WGSM genes that, when applied to an individual's actual gene expression can accurately predict that individual's risk for autism in screening or make accurate autism diagnostic or prognostic classification about that individual. It can also be used as a diagnostic test for autism for those already known to be at high risk for autism or suspected to have autism and other developmental disorders. It can also provide both a diagnostic classification prediction (autism, not autism) and an estimation of probability-risk for autism or other developmental disorders in newborns, infants, toddlers and young children.

The inventive method can further comprise an earlier step of obtaining an analyte in a biological sample, which refers to physically obtaining the analyte of interest in the biological sample directly from the body of a subject or physically moving a sample that has been previously taken from the subject. The biological sample can include but is not limited to, blood, cord blood, serum, plasma, cerebrospinal fluid, urine, tears, saliva, mucous, buccal swab, tooth pulp, skin, neuron, and any other bodily fluid, tissue or organ. The biological sample can also include cells obtained and/or derived from the biological samples and/or cell culture, including, but not limited to stem cells, fibroblasts, iPs, neuroprogenitor cells, and neural cells. In certain embodiments, the analyte includes, but is not limited to, DNA, RNA, protein, or metabolite in any biological sample. In certain embodiments, the analyte is blood-derived RNA from leukocytes. In certain embodiments, the WGSM applies weights gene-wise to an individual's normalized blood-derived (including a newborn's cord blood-derived) gene expression levels. Therefore, to screen and test for autism in newborns for example, the WGSM can be applied gene-wise to the individual's cord blood-derived RNA gene expression levels, and algorithms calculate autism risk. The WGSM is used alone or in combination with the other matrices discussed below. The elements contained in each of the other matrices can also be used as predictors in the diagnostic classification or prognostic analysis.

The inventive method therefore may also further comprise a comparison of a gene-network, including hub-gene network, signature matrix (GNSM) of the subject to the GNSM autism reference database, to establish a score for autism risk screening, diagnosis or prognosis based on the divergence of the subject's GNSM to the GNSM autism reference database. In certain embodiments, the GNSM comprises interaction patterns of specific gene-weights and features calculated from gene-to-gene interactions, including hub-gene interactions. The interaction patterns are calculated based on the relationship or state of a gene with non-genomic features.

The inventive method may also comprise a step of comparing a multi-modal signature matrix (MMSM) of the subject to the MMSM autism reference database, to establish a score for autism risk screening, diagnosis or prognosis based on the divergence of the subject's MMSM to the MMSM autism reference database. In certain embodiments, the MMSM is a matrix containing the quantification of non-genomic features obtained by clinical, behavioral, anatomical, and functional measurements. The non-genomic features comprise but are not limited to, age, a GeoPreference test score, a MRI/fMRI/DTI test, an Autism Diagnostic Observation Schedule (ADOS) test, or a CSBS test.

In certain embodiments, the invention is unique in utilizing a test based on specific age-weighted and age-change patterns and gene-weights of abnormal gene expression (for instance Weight Sets 1-4 in Table 1) in infants and toddlers with confirmed autism via longitudinal tracking. In certain embodiments, the invention provides a method specifically designed to leverage age-related gene expression differences between autistic and normal individuals in order to indicate probability risk for autism as it occurs at varying ages in the general pediatric population, making this a unique approach. Therefore, in certain embodiments the invention is a test based on the unique multidimensional gene and age weighted dataset of autism that is a reference standard for testing new patients/subjects at risk for autism across ages from newborns to young children. Thus, in certain embodiments, it can use age to transform values of elements in the WGSM and GNSM to improve the accuracy of tests for ASD based on the unique knowledge of how gene expression changes with age (e.g., in the first year of life) in ASD subjects. In certain embodiements, it can use age as a feature in classification (for example see Scoring/CLASS identity method below). Presented herein is the first evidence of age-related gene expression changes in any tissue that correlated with ASD at these early ages. In practice, each gene expression element in the WGSM and GNSM will change by a function of age, with functions ranging from age-independence to gain or loss of expression with decreasing age. These age dependent changes were determined and this information was used to adjust the weighting factors for each gene to age-appropriate weightings to enhance diagnostic performance at the age of individual patients.

Moreover, in some embodiments the invention provides a method further comprising a unique step of comparing a collateral feature signature matrix (CFSM) of the subject to the CFSM autism reference database, to establish a score for autism risk screening, diagnosis or prognosis based on the divergence of the subject's CFSM to the CFSM autism reference database. The CFSM comprises features collateral to the subject, for instance, the collateral features comprise analytes in maternal blood during pregnancy, sibling with autism, maternal genomic signature or preconditions, or adverse pre- or perinatal events.

In some embodiments, the invention further provides a method for autism preclinical screening, diagnosis or prognosis, comprising: a) obtaining a biological sample containing analytes of interest; b) preparing a weighted gene signature matrix (WGSM) comprising expression levels of a selected set of two or more analyte-associated genes selected from the genes listed in Tables 1-2 and 16-25; c) calculating a weighted gene expression level of each gene in the selected set by multiplying a normalized gene expression value (NGEV) of the WGSM by the gene-specific weight of that gene provided in Tables 1-2 and 16-25; and d) establishing the divergence of the set of each weighted gene expression level of the subject to a weighted gene expression reference database (WGERD), to thereby indicate increasing correlation with autism risk, diagnosis or prognosis. In certain embodiments, the WGSM is further processed to reduce dimensionality or computation time and increase power in the subsequent analysis steps.

In certain embodiments, using functional genomic and biological systems analyses, signatures of blood-derived RNA expression are derived from autism and subjects without autism that are patterns of "gene-specific-weights" (the WGSM) as well as patterns of gene-specific weights as a function of gene-gene interaction patterns (the GNSM), quantifiable features of the individual (e.g., age, sex, head circumference, neuroimaging measures, eye-tracking score; the MMSM) and collateral features (e.g., analytes in maternal blood during pregnancy, sibling with autism, adverse pre- or perinatal events; the CFSM). In essence, these genomic signatures transform the measured gene expression levels obtained from an individual through algorithm and knowledge-based selective application of the derived weighted-patterns that selectively enhance or diminish the impact of the measured levels on detection, diagnostic and prognostic classifications and risk estimates. The non-genomic feature matrices instead function as predictor variables.

In some embodiments, the invention therefore provides the use of these four derived signature matrices unified as the weighted gene and features matrix (WGFM) that is implemented as the weighted gene and feature tests for autism (WGFTA) for pediatric population screening for risk of autism and for autism diagnostics and prognostics in newborns, babies, infants, toddlers and young children. For example, its prognostics uses include prediction and characterization of likely clinical, neural and treatment progress and outcome. In certain embodiments, the WGFTA uses each in single or in any combination of the following four matrices of the WGFM: The Weighted Gene Signature Matrix (WGSM), The Gene-Networks Signature Matrix (GNSM), The Multi-Modal Signature Matrix (MMSM), and the Collateral Features Signature Matrix (CFSM). In particular embodiments, these signature matrices are designed to optimize, for example, screening for and detection of newborns and babies at risk for autism, while others are designed for use in the clinical evaluation and diagnostic confirmation of babies, infants, toddlers or young children previously identified as being at risk for autism, and in still others for use in the prognostic evaluation of probable clinical course (e.g., worse or improving clinical severity), later clinical outcome (later language, cognitive or social ability), or treatment response.

In some embodiments, the invention also provides a system for autism screening, diagnosis or prognosis, comprising a database generated model of at least two genes and corresponding gene-specific weights as provided in Tables 1-2 and 16-25, and instructions for use in applying the database to a weighted gene signature matrix (WGSM) comprising expression levels of a selected set of the same two or more genes expressed in a biological sample by a) calculating a weighted gene expression level of each gene in the selected set by multiplying a normalized gene expression value (NGEV) of the WGSM by the gene-specific weight of that gene provided in Tables 1-2 and 16-25; and b) establishing the divergence of the set of each weighted gene expression level of a subject to a weighted gene expression reference database (WGERD), to thereby indicate increasing correlation with autism risk, diagnosis or prognosis.

The invention is currently the only functional genomic test of autism that is based on direct experimental knowledge of the genetic functional effect and neural outcome defects that underlie brain maldevelopment in autism at varying young developmental ages, and the only autism genetic test that detects a majority of autism individuals. The invention is platform independent, and has been tested and validated on independent cohorts of patients and by using different methods.

BRIEF DESCRIPTION OF THE DRAWINGS

FIG. 1A) Total Brain Volume (TBV) measure distributions in ASD and control toddlers. T-test showed no statistically significant difference in the two distributions (pValue=0.645). FIG. 1B) WGCNA analysis across all ASD and control subjects together (combined analysis) identified seven modules of co-expressed genes that are associated with neauroanatomic measures (see also Table 5). The bar graph displays the enrichment scores of the seven modules using Metacore pathway analysis. FIG. 1C) The eigengene values of the same seven modules were used in a correlation analysis with the neuroanatomic measures (see Table 6). Overall six of the seven modules (gene networks) display statistically significant association with the neuroanatomic measures, but the association was different within each group. The scatter plots provide a graphical representation of the relationship between module eigengenes (gene expression variance) and total brain volume variation in the ASD (light grey) and control (dark grey) groups. The most evident differences between the two groups account for gene patterns in the cell cycle, protein folding and cell adhesion modules. Additional differences are found in the cytoskeleton, inflammation and translation gene modules. High expression levels of cell cycle and protein folding genes are found in normally small brains, while the other gene networks seem to have a weaker effect in keeping the brain from growing in size. Conversely, the combination of reduction in cell cycle and protein folding genes together with variations in gene expression levels in the other functional networks are found to drive pathological brain enlargement in ASD.

FIG. 2A) Genes involving cell cycle and protein folding. FIG. 2B) Genes involving cell adhesion and cytoskeleton. 2C) Genes involving translation and inflammation.

FIG. 4A) Pathway enrichment comparison in Metacore between the Discovery and Replication DE genes. DNA-damage and Mitogenic signaling share the strongest similarity. FIG. 4B) Pathway enrichment analysis of the commonly dysregulated genes in both Discovery and Replication samples. FIG. 4C) Left panel, ROC curves and AUC values from the classification of Discovery (ROC 1) and Replication (ROC 2) subjects. Right panel, ROC curves and AUC values from the classification of all subjects in the different diagnostic categories. ROC 3=ASD vs typically developing (TD) toddlers (thus excluding contrast subjects); ROC 4=ASD vs contrast toddlers; ROC 5=contrast vs TD toddlers. FIG. 4D) Coordinates extracted from all ROC curves in panel C. FIG. 4E) Cytoscape visualization with the PanGIA module style using the genes from the four modules with direct PPI (DAPPLE database). The number of interactions is correlated with the color and position within the network. White indicates $<8$ PPI; yellow to red indicates $8 \leq PPI < 31$. The core of the network, represented by the genes with the highest number of interactions, is enriched with translation genes.

FIG. 6A) MEDARKRED-MESALMON. FIG. 6B) METAN-MEGREY.

FIG. 8A) MEMAGENTA-MEGREEN YELLOW. FIG. 8B) MEGREY60-MEGREY.

FIG. 9A) MELIGHT GREEN-MEDARKRED. FIG. 9B) MEGREEN YELLOW-MEGREY.

FIG. 13A) example of change in gene expression with a main effect of diagnosis (ASD in light grey vs Control in dark grey). FIG. 13B) example of change in gene expression with main effects of age and diagnosis. FIG. 13C) example of change in gene expression with interaction between age and diagnosis.

FIG. 14A) Graphical representation of the classification outcome in the training set (continuous line) and after cross-validation (dotted line) with age as additional predictor. FIG. 14B) Graphical representation of the classification outcome without age as predictor. When using age as additional predictor the cross-validation error diminish from about 0.3 (30%) to about 0.2 (20%), thus suggesting that age is helpful in improving classification accuracy.

DETAILED DESCRIPTION OF THE INVENTION

Figure 1A:
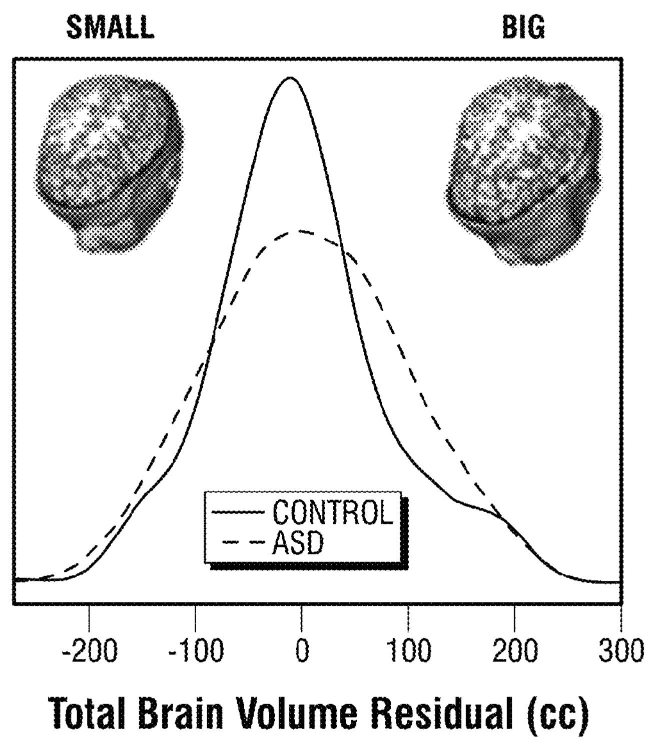
FIGS. 1A-1C. Gene Networks are associated with neuroanatomic measures variation and distinguish ASD from control toddlers.

Various publications, including patents, published applications, technical articles and scholarly articles are cited throughout the specification. Each of these cited publications is incorporated by reference herein, in its entirety.

Throughout this specification, the word "comprise" or variations such as "comprises" or "comprising" will be understood to imply the inclusion of a stated integer (or components) or group of integers (or components), but not the exclusion of any other integer (or components) or group of integers (or components).

The singular forms "a," "an," and "the" include the plurals unless the context clearly dictates otherwise.

The term "including" is used to mean "including but not limited to." "Including" and "including but not limited to" are used interchangeably.

In some embodiments, the invention provides a use of functional genomic signatures in combination with functional genomic-based multimodality signatures in screening for autism risk and in autism diagnostics and prognostics. The multimodality signatures include, but are not limited to, physical, neurobehavioral, neuroimaging, neurophysiological, clinical history, genetic, maternal precondition, parent questionnaire, family history and behavioral and psychometric test information, and derived from bioinformatic and biological systems analyses of analytes collected in vivo from peripheral tissues including cord blood, blood, skin and urine. The invention specifically provides the use of varying forms of such signatures each tailored to optimize autism screening, diagnostics and prognostics according to the individual's age, sex, ethnicity, and clinical and family history, thus, providing pediatric population screening biomarkers of risk for autism and diagnostic and prognostic biomarkers of autism (i.e., Autism Spectrum Disorders or ASD as defined in DSM V and broadly characterized in DSM-IV-TR) and risk for autism in individuals at young ages, including newborns, babies, infants, toddlers and young children. Prognostic biomarkers as used herein include those that predict and characterize likely clinical, neural and treatment progress and outcome.

In certain embodiments, the invention can test for risk of autism in any newborn, infant, toddler or young child. The functional genomic and functional genomic-based multimodal signatures presented here, developed from general pediatric populations at young ages, have far better accuracy, specificity and sensitivity than any previously developed biological- or behavior-based screen or early classifier in ASD newborns and 0 to 1 year olds 1 to 2 year olds, 2 to 3 year olds and 3 to 4 year olds. In particular embodiments, the invention provides computer-based bioinformatics analyses that have derived genomic and genomic-based multimodal signatures in vivo that efficiently predict autism at very young ages.

Because autism is a strongly genetic disorder of neural development, a major breakthrough in risk assessment of autism would be the ability to identify functional genomic defects that relate to and may underlie brain development in autism at the youngest ages possible. From such gene-brain knowledge, better and more autism-relevant biomarkers of early risk should be obtainable. Therefore, in some embodiments the invention provides unique analyses not performed previously by any other researchers in the autism field that identified functional genomic defects in blood leukocyte mRNA that are strongly correlated with brain and cerebral cortex developmental size in very young autistic subjects. In certain embodiments, the invention provides that among the genes so involved, a large percentage of them are also abnormally dysregulated as compared to the typically developing control infants and toddlers. This result is the first identification of a functional genomic pathology in the first years of life in autism. Using bioinformatics and systems biology analyses, the invention provides functional genomic and functional genomic-based multimodality signatures (the weighted gene and features matrix) for autism screening, diagnosis and prognosis, which is used in the invention of the weighted gene and feature tests of autism (WGFTA).

The WGFTA of the invention detects, quantifies risk and classifies autism, and other developmental disorders at the youngest ages in the general pediatric population with greater accuracy, specificity, sensitivity and positive predictive value than any other published method. These are the first clinically-relevant, brain development-relevant and practical genomic signatures of risk for autism in newborns, infants, toddlers and young children. This set of signatures detects subtypes of autism with more severe as well as less severe involvement. As such, the WGFTA impacts identification of those with more severe neuropathology and reveals differential prognosis. Moreover, repeat testing with the WGFTA enables tracking and understanding longitudinal changes in autism neural and clinical pathology across development in autism. Not only does the invention of WGFTA set of tests have substantial clinical impact at the level of the individual child—a first in the autism field, but the invention also impacts studies linking genetic and non-genetic etiological variables in this disorder.

More detailed descriptions of the invention of WGFTA and associated signature matrices are provided below. In certain embodiments, the invention provides the weighted gene feature tests of autism (WGFTA), which is the application of each single or any combination of the following matrices, unified under the name "Weighted Gene and Features Matrix" ("WGFM"):

The weighted gene signature matrix (WGSM) is a matrix containing sets of genes and gene-weights, which constitutes a model of referenced dataset. In certain embodiments, gene weights are derived from a computational bioinformatics analysis of the relative expression levels of at least the selected set of genes from more than 40 healthy individuals and 40 autistic individuals compiled in a weighted gene expression reference database (WGERD). In certain embodiments, the invention provides a WGSM and/or WGERD with at least 2, 10, 20, 25, 30, 35, 40, 50, 60, 70, 80, 160, 320, 640, 762, 800, 900, 1,000, 1,500, 2,000, 2,500 or more genes, or any number of genes and their respective weights determined as described and exemplified herein. The genes can be arranged into sets of common expression patterns, as an example, 4 sets are shown in Table 1. In certain embodiments, the referenced database WGERD of the invention is designed to be constantly updated with new subjects and additional features (e.g., sequencing data) so that the genes and gene weights, as well as non-genomic features can be updated accordingly.

The weights of genes provided in Table 1 can be rounded to the nearest 1/10; 1/100; 1/1,000; 1/10,000; 1/100,000; 1/1,000,000; 1/10,000,000; or 1/100,000,000. The genes are provided in ranked order of their weighted correlation as provided in Tables 1.1 through 1.4.

One computer-based bioinformatic algorithm used to determine the weighted values is part of the Weighted Gene Co-expression Network Analysis (WGCNA) package in R computer environment (cran.us.r-project.org/). The use of this package is also described in example 1 and 2 methods (see below). Quantification of gene expression levels and therefore weight calculations are platform and method independent. Microarray-based platforms (for instance, Affymetrix, Illumina Nimblegen chips), sequencing-based reactions (for instance Illumina or Roche next-generation seq or traditional Sanger seq) and any other quantitative approaches (for instance qPCR-based such as the Fluidigm system) can be used to determine nominal gene expression levels and with any of the weight calculation methods described herein. Using recommended settings in the WGCNA package, cleaned and normalized gene expression data is clustered into gene sets (herein called Modules) based on similarity of co-expression. Genes with similar expression patterns across subjects are assigned to a specific module. For each module and each subject an eigengene is then calculated. Calculation of the eigengene values is done via the computer formula "moduleEigengenes (data)" where "data" is the variable containing the gene expression values of all subjects. This step is equivalent to the conventional principal component analysis in which the variance of a multi-dimensional dataset (many genes) is represented by one value (component 1 or eigengene value). The weights are then calculated by using the "cor( )" formula in R with "data" and "eigengenes" as arguments. This function performs correlation analysis between a module eigengene value and the expression value of each gene within the same module. Correlations are performed for all genes in a module and for all modules. Using this method, weights values range from −1 to 1, and represent the contribution of genes to the overall gene expression variance of each particular module. Genes with weights values closer to −1 and 1 have the highest contribution, thus importance. Weights are calculated also using other analogous data-reduction methods that may or may not include a priori clustering steps as to the case of WGCNA (based on co-expression). Examples are Principal Component Analysis (PCA), Multi-Dimensional Scaling (MDS), and Independent Component Analysis (ICA). In these examples, weights are commonly referred as "Loadings". Weights calculation is extended also to the use biological information, such as protein-protein interactions (PPIs), gene-to-gene interactions (GGIs), Gene Ontology (GO) information, and network or ranking position; therefore both statistical and biological-based methods can be applied to derive weights/loadings from gene expression data.

The present invention provides, for the first time, the use of weights in the screening and diagnosis of autistic subjects, especially at young ages (birth to age 4 years). Autism involves disrupted hub genes and gene pathways, sub-networks, networks and modules (see EXAMPLE 1), and the patterns of less to more abnormal gene expression within these systems is encoded and used for autism screening and diagnostics in the invention. In some embodiments, this is done via PPIs and/or GGIs as just stated and such pattern information is in the GNSM. In other embodiments, the patterns of less to more abnormal gene expression are encoded by gene weights. This gene-weighting improves performance, and can be used in combination with classifying genes into modules or independently of modules.

Similarly, clustering the genes into modules can be used alone or in combination with GNSM, MMSM, and CFSM.

The study of the unique reference dataset of ASD and control infants and toddlers provided the unique opportunity to discover importance levels of genes (from low to high priority) for the identification of autism risk. Based on the biological information present in our reference dataset, genes with higher priority have a higher importance in correctly classifying ASD patients. Priority was assigned based on the weight value calculated for each gene. As described above, genes with weights values closer to −1 and 1 have the highest contribution (and, thus importance). Therefore, gene lists can be selected based on the weight values. For example, in some embodiments, a gene list can be selected from genes with an absolute weight value of 0.15 to 0.4, from 0.5 to 0.7, or above 0.8. In certain embodiments, a gene list can be generated by selecting genes with an absolute weight value of above 0.15, above 0.20, above 0.25, above 0.30, above 0.35, above 0.40, above 0.45, above 0.50, above 0.55, above 0.60, above 0.65, above 0.70, above 0.75, above 0.80, above 0.85, above 0.90, above 0.91, above 0.92, above 0.93, above 0.94, above 0.95, above 0.96, above 0.97, above 0.98, or above 0.99. The genes can be selected with or without using clustering to define particular modules before applying the weighting. The four "Top 50" gene sets show weights ranging from approximately 0.53 to 0.98 for the top 50 genes of four different modules. Alternatively, the absolute weights can be used as a threshold (with or without clustering) to determine a number of genes having a weight above, for example, any of the absolute weights listed above.

TABLE 1

| GeneID__set 1 | Weights Set 1 | GeneID__set 1 | Weights Set 1 | GeneID__set 2 | Weights Set 2 | GeneID__set 3 | Weights Set 3 | GeneID__set 4 | Autism Dx Set 4 |
|---|---|---|---|---|---|---|---|---|---|
| CD3D | 0.935783593 | C2orf3 | 0.643325498 | CUTL1 | 0.899346773 | LOC44926 | 0.952217397 | SDPR | 0.982476 |
| UXT | 0.899396969 | PDCL | 0.641692741 | MAST3 | 0.891222232 | ITM2B | 0.918889397 | PDE5A | 0.936387 |
| RPS4X | 0.897584727 | ZNF544 | 0.641399133 | STK4 | 0.858164628 | HOXC6 | 0.899386247 | PTGS1 | 0.885464 |
| LOC283412 | 0.893348386 | PAK1IP1 | 0.641392622 | KIAA247 | 0.842925274 | LOC392288 | 0.895514994 | CTDSPL | 0.883295 |
| LOC127295 | 0.891939246 | LOC4455 | 0.639352929 | MYH9 | 0.829782866 | YIPF4 | 0.891398192 | CTTN | 0.88314 |
| LOC42694 | 0.891528532 | PAQR8 | 0.639332216 | RAPGEF2 | 0.817284111 | RBMS1 | 0.888876658 | ALOX12 | 0.872153 |
| SKAP1 | 0.891256553 | TMEM5B | 0.638786733 | ARAP3 | 0.815255748 | USP6 | 0.871882682 | MPL | 0.867286 |
| LOC72882 | 0.889935118 | C22orf32 | 0.636925896 | RAB11FIP1 | 0.797221635 | KIAA133 | 0.868831295 | DNM3 | 0.856197 |
| LOC645173 | 0.888169553 | CXCR7 | 0.63651849 | WBP2 | 0.796352118 | LOC642567 | 0.867721395 | C1orf47 | 0.848722 |
| RPL23A | 0.887966784 | RTBDN | 0.635348948 | GNAI2 | 0.795553329 | EVI2B | 0.865616513 | C7orf41 | 0.828971 |
| LOC646942 | 0.883945464 | EEF1G | 0.634822364 | MTMR3 | 0.795286983 | UBE2W | 0.851386357 | C5orf4 | 0.827413 |
| LOC646294 | 0.881255183 | RPL37 | 0.633756743 | CBL | 0.792889746 | DDX3X | 0.849399278 | RAB27B | 0.815966 |
| LOC728428 | 0.881254479 | KIAA355 | 0.63224944 | UBE4B | 0.792663385 | UBE2D1 | 0.844426485 | CXorf2 | 0.811991 |
| LOC44737 | 0.871745735 | MRPS27 | 0.631945943 | IGF2R | 0.791413796 | HIAT1 | 0.841479672 | GRAP2 | 0.797727 |
| LOC7329 | 0.871551112 | SSR4 | 0.629113287 | YPEL3 | 0.789244232 | TTRAP | 0.837658199 | CDC14B | 0.782988 |
| LOC391833 | 0.868862845 | TOMM7 | 0.628843995 | SETD1B | 0.784239228 | LOC44525 | 0.83588163 | DAB2 | 0.771423 |
| RPS3 | 0.867774287 | LOC1131672 | 0.628653337 | PIK3CD | 0.782776396 | C18orf32 | 0.828614134 | TAL1 | 0.755586 |
| RPL36 | 0.864561634 | KRT73 | 0.628159669 | RASSF2 | 0.775818951 | LOC1132888 | 0.826453522 | NCALD | 0.747679 |
| LOC1127993 | 0.86394855 | POLR1D | 0.625815554 | KDM6B | 0.774456479 | ROCK1 | 0.821534228 | ITGB5 | 0.74494 |
| LOC73187 | 0.862255251 | INPP4B | 0.625699386 | TP53INP2 | 0.769228192 | LOC64798 | 0.818875634 | GUCY1A3 | 0.732784 |
| LOC72831 | 0.861398415 | ALKBH7 | 0.623546371 | NUAK2 | 0.764937137 | FAM91A2 | 0.8151116 | FERMT3 | 0.725864 |
| LOC653162 | 0.857976375 | AKR7A3 | 0.622561242 | PAK2 | 0.764551187 | SENP6 | 0.81341925 | TSC22D1 | 0.725234 |
| LOC729679 | 0.856634917 | OGFOD1 | 0.622236454 | MYO9B | 0.758257515 | LOC732229 | 0.812945123 | LIMS1 | 0.722976 |
| LOC441246 | 0.856563215 | COX7A2L | 0.622161758 | NDE1 | 0.757911755 | CEP63 | 0.812863172 | SLC8A3 | 0.721372 |
| LOC387841 | 0.853626697 | SNORD16 | 0.619846554 | IRS2 | 0.748758318 | ATG3 | 0.811914569 | ABCC3 | 0.716486 |
| C13orf15 | 0.853475792 | PRKCA | 0.619788175 | PHF2 | 0.747211227 | LOC1128269 | 0.79772624 | HOMER2 | 0.713716 |
| LOC728576 | 0.852817639 | MAN1C1 | 0.617174926 | MAP2K4 | 0.746288868 | PLAGL1 | 0.79624413 | NAT8B | 0.712372 |
| EIF3K | 0.851382429 | COX11 | 0.617173924 | CAMK1D | 0.743845616 | MBD2 | 0.794667574 | FBLN1 | 0.695683 |
| EEF1B2 | 0.848139827 | EDAR | 0.616832496 | CDC2L6 | 0.739975446 | EXOC8 | 0.789627347 | ARHGAP21 | 0.688976 |
| LCK | 0.847839497 | SMYD2 | 0.615536584 | ASAP1 | 0.734296313 | MRRF | 0.788483797 | C21orf7 | 0.688378 |
| LOC39345 | 0.846855595 | C2orf196 | 0.615182754 | TSC22D3 | 0.729781326 | LOC113377 | 0.785194167 | C15orf52 | 0.687782 |
| RPL4 | 0.846548149 | ACYP2 | 0.61357462 | TLN1 | 0.728642978 | POTE2 | 0.784824825 | CABP5 | 0.682826 |
| LOC1132742 | 0.842833281 | GCET2 | 0.613272559 | ANXA11 | 0.727162993 | C8orf33 | 0.783663596 | ENDOD1 | 0.663152 |
| EIF3H | 0.842637899 | SNORD13 | 0.612937581 | EP3 | 0.726274852 | LOC38953 | 0.78121382 | SOCS4 | 0.66279 |
| CD27 | 0.842195295 | C1orf14 | 0.612368536 | ROD1 | 0.725977368 | CPEB3 | 0.773273834 | C15orf26 | 0.644173 |
| RPS15 | 0.841763438 | LOC647276 | 0.611266653 | RXRA | 0.725773276 | C6orf211 | 0.769958713 | PVALB | 0.638495 |
| LOC649447 | 0.839379287 | PLEKHF1 | 0.598224876 | RASSF5 | 0.721366824 | LOC1128533 | 0.769836835 | SLC24A3 | 0.637579 |
| LOC1131713 | 0.838956452 | FKBP14 | 0.598185865 | PELI2 | 0.719737185 | LOC648863 | 0.769661334 | HGD | 0.635255 |
| LOC286444 | 0.837678151 | FOXO1 | 0.597245265 | SEMA4D | 0.717738781 | STX7 | 0.767879114 | ZNF185 | 0.628879 |
| LOC729789 | 0.837517553 | LOC339352 | 0.594815425 | PPM1A | 0.716812485 | 14-Sep | 0.764666259 | CA2 | 0.624763 |
| RPL1A | 0.828892451 | ZNF395 | 0.594235542 | CREBBP | 0.716647465 | LOC4493 | 0.763746743 | CXCL5 | 0.618479 |
| CD6 | 0.826562257 | DSTN | 0.592351455 | LAPTM5 | 0.716353697 | LOC442319 | 0.763346856 | GRB14 | 0.617611 |
| LOC646766 | 0.824653268 | RPS29 | 0.591862228 | CABIN1 | 0.715925162 | NCRNA81 | 0.751898522 | VWF | 0.611157 |
| C17orf45 | 0.823936864 | SNORD21 | 0.591444476 | PLCB2 | 0.715345575 | CLEC7A | 0.744233541 | DKFZp686I15217 | 0.599262 |
| CUTA | 0.823637548 | LOC64663 | 0.589558195 | WNK1 | 0.711353632 | CSNK1A1L | 0.733761775 | NDUFS1 | 0.593178 |
| EIF3F | 0.82286832 | TBCA | 0.588271553 | BCORL1 | 0.698292888 | LOC643896 | 0.731569432 | GRASP | 0.581414 |
| LOC642741 | 0.822312667 | PLAG1 | 0.586638621 | SIK3 | 0.697558261 | P74P | 0.725849778 | RGS18 | 0.572236 |
| LOC388339 | 0.821936639 | TTC39C | 0.585818195 | SLC44A2 | 0.696529915 | GABARAPL2 | 0.723517197 | C16orf68 | 0.562993 |
| RPS14 | 0.821669767 | ZNF16 | 0.585192385 | EPOR | 0.692878472 | FCGR3A | 0.717268353 | MGC135 | 0.552543 |

TABLE 1-continued

| GeneID_set 1 | Weights Set 1 | GeneID_set 1 | Weights Set 1 | GeneID_set 2 | Weights Set 2 | GeneID_set 3 | Weights Set 3 | GeneID_set 4 | Autism Dx Set 4 |
|---|---|---|---|---|---|---|---|---|---|
| LOC11398 | 0.818423753 | LOC645233 | 0.584896119 | SP2 | 0.686587522 | LOC65638 | 0.714919235 | LOC64926 | 0.548172 |
| LOC643531 | 0.818367581 | CENPL | 0.58453599 | IP6K1 | 0.686339387 | FAM126B | 0.713524823 | HIST1H2AE | 0.53314 |
| LOC642357 | 0.815418616 | XYLT2 | 0.583954832 | LPIN2 | 0.686253547 | TOP1P2 | 0.711774489 | TCEA3 | 0.472277 |
| LOC4455 | 0.815254917 | TSPAN5 | 0.581829618 | TGFBR2 | 0.681731345 | TFEC | 0.697721596 | MEIS1 | 0.453958 |
| RPS5 | 0.81396843 | LOC4464 | 0.578616713 | MYST3 | 0.67599148 | HERPUD2 | 0.692843953 | MSRB3 | 0.448888 |
| PIK3IP1 | 0.812422946 | HABP4 | 0.578161674 | MID1IP1 | 0.675927736 | RPAP3 | 0.689713938 | DNHD2 | 0.448113 |
| RPL5 | 0.799548493 | NHP2 | 0.577712263 | AHCTF1 | 0.675368429 | LOC644964 | 0.688291553 | IRX3 | 0.396578 |
| FLT3LG | 0.798617496 | SELM | 0.571396694 | CHES1 | 0.675156518 | LOC391769 | 0.673227357 | SPG21 | 0.389869 |
| ATXN7L3B | 0.798521571 | DCXR | 0.56883363 | MAP1LC3A | 0.673939379 | BRD7P2 | 0.664481299 | SPC25 | 0.374118 |
| DKFZp761P423 | 0.797275569 | PHB | 0.56679772 | KDM5B | 0.673634194 | ANP32A | 0.662291765 | | |
| POLR1E | 0.795479112 | CD32 | 0.565674142 | ZYG11B | 0.673297864 | LOC641992 | 0.647881441 | | |
| C2orf89 | 0.794392985 | DLEU1 | 0.564859273 | POLR2A | 0.665496976 | PAPSS2 | 0.637828688 | | |
| C11orf2 | 0.793512166 | DUSP14 | 0.562495337 | AKT1 | 0.663541972 | LOC1128627 | 0.637538136 | | |
| FAM1A4 | 0.793287257 | MSX2P1 | 0.559554447 | TBL1X | 0.662364885 | KRT8P9 | 0.63712914 | | |
| LDHB | 0.791745887 | RNF144A | 0.559297465 | IMPA2 | 0.65781512 | TMX4 | 0.612694353 | | |
| LOC73196 | 0.791625893 | AHCY | 0.558954772 | ATG2A | 0.654245217 | LOC64552 | 0.59882446 | | |
| LOC44927 | 0.789154863 | FAM134B | 0.558375382 | MAPKAPK2 | 0.653979578 | LOC389286 | 0.596113393 | | |
| TNFRSF25 | 0.786317228 | TYSND1 | 0.556848766 | FAM11B | 0.649818256 | CWC22 | 0.592755277 | | |
| ZNF329 | 0.782992446 | LOC728953 | 0.554168254 | CENTB2 | 0.648915988 | SH3BP2 | 0.55771393 | | |
| LOC644464 | 0.779129219 | LOC387791 | 0.551536874 | RFX1 | 0.648867183 | LAPTM4A | 0.551788533 | | |
| RAB33A | 0.776193173 | SELPLG | 0.549789855 | SPI1 | 0.642942512 | SYTL2 | 0.499767546 | | |
| RPL22 | 0.775782518 | KLRB1 | 0.548467766 | ZNF281 | 0.641915681 | ANP32C | 0.378151333 | | |
| LOC388564 | 0.774155475 | ATP5E | 0.547577933 | USP9X | 0.641791596 | LOC1134291 | 0.277985424 | | |
| C6orf48 | 0.772942779 | TCP1 | 0.547495293 | DPEP2 | 0.641158453 | LARP1 | −0.312422458 | | |
| DDHD2 | 0.772697886 | ZDHHC9 | 0.544612934 | PACS1 | 0.636214668 | C18orf1 | −0.315553843 | | |
| PKIA | 0.771777911 | CCDC72 | 0.543531769 | GATAD2B | 0.631961987 | TCEAL4 | −0.394177985 | | |
| C11orf1 | 0.77146654 | RNF144 | 0.543479417 | MGC42367 | 0.631548612 | SDHAF1 | −0.415292518 | | |
| RWDD1 | 0.769315667 | MARCKSL1 | 0.543422113 | PJA2 | 0.629172534 | CCDC9A | −0.418249658 | | |
| LOC389342 | 0.769266259 | GPX4 | 0.541737879 | BRD3 | 0.628793665 | ODC1 | −0.488451364 | | |
| CA5B | 0.768742497 | VSIG1 | 0.539617567 | KIDINS22 | 0.622713163 | ARHGAP1 | −0.495153647 | | |
| DAP3 | 0.765349952 | DHRS3 | 0.538953789 | FAM12A | 0.59691644 | TADA1L | −0.517862143 | | |
| ATPGD1 | 0.765166323 | CNNM3 | 0.537386642 | RAB11FIP4 | 0.596547435 | LOC92249 | −0.579379826 | | |
| C12orf65 | 0.764854517 | FBLN2 | 0.535467587 | OSBPL8 | 0.593855675 | CD99 | −0.59333825 | | |
| ATP5A1 | 0.7645682 | ELOVL4 | 0.535114973 | CCNK | 0.592217195 | HCST | −0.625513721 | | |
| IL27RA | 0.763477657 | PRRT3 | 0.534237637 | SGK | 0.588593659 | TRAPPC4 | −0.643976448 | | |
| ORC5L | 0.762996289 | VHL | 0.532395335 | PCBP2 | 0.586773694 | EIF2AK1 | −0.644486837 | | |
| MFNG | 0.761418624 | HNRNPU | 0.531745499 | SNORA28 | 0.584584438 | CS | −0.653859524 | | |
| APOA1BP | 0.759114222 | FCGBP | 0.527263632 | C14orf43 | 0.573927549 | LOC1128731 | −0.654961437 | | |
| USP47 | 0.758717998 | GOLPH3L | 0.527213868 | ELMO1 | 0.571788753 | ILVBL | −0.655857192 | | |
| PEX11B | 0.754628868 | LMNB2 | 0.524692549 | TMCC1 | 0.566173385 | SETD1A | −0.662596368 | | |
| CRBN | 0.754152497 | CCT3 | 0.524567526 | DGCR8 | 0.564982984 | LOC4948 | −0.724984343 | | |
| C12orf29 | 0.753564787 | CRIP1 | 0.52227375 | NCOR2 | 0.563615666 | | | | |
| TTC4 | 0.752585135 | ZFP3 | 0.517155756 | UBAP2L | 0.558982967 | | | | |
| C1QBP | 0.752379867 | PEBP1 | 0.515338931 | PRKCB | 0.556183699 | | | | |
| LOC728128 | 0.751472664 | 9-Sep | 0.514442369 | SEC16A | 0.555783769 | | | | |
| GDF11 | 0.74939769 | TSTD1 | 0.51172194 | C13orf18 | 0.555593833 | | | | |
| C16orf53 | 0.748642633 | SNHG9 | 0.498816845 | HNRPUL1 | 0.54417842 | | | | |
| LOC347292 | 0.748154744 | NDUFAF3 | 0.493661179 | LASP1 | 0.543199946 | | | | |
| EIF3L | 0.747991338 | ACOT4 | 0.493494423 | SF3A1 | 0.537427512 | | | | |
| QARS | 0.746682333 | LIAS | 0.493133496 | HELZ | 0.532982164 | | | | |
| TCEAL8 | 0.738139918 | ST6GALNAC4 | 0.492572367 | ABAT | 0.532615683 | | | | |

TABLE 1-continued

| GeneID_set 1 | Weights Set 1 | GeneID_set 1 | Weights Set 1 | GeneID_set 2 | Weights Set 2 | GeneID_set 3 | Weights Set 3 | GeneID_set 4 | Autism Dx Set 4 |
|---|---|---|---|---|---|---|---|---|---|
| LOC4963 | 0.737889313 | C1orf35 | 0.491497922 | PRKCB1 | 0.531452289 | | | | |
| LOC25845 | 0.73723136 | KIAA143 | 0.489514968 | NCF1B | 0.528432749 | | | | |
| SMYD3 | 0.734452589 | TIMM22 | 0.489238613 | CUGBP2 | 0.526196965 | | | | |
| MGC87895 | 0.733843872 | TMEM116 | 0.489235392 | ANGPT1 | 0.523883946 | | | | |
| SEC62 | 0.733293263 | DBP | 0.488445622 | MAPRE3 | 0.522517685 | | | | |
| PRAGMIN | 0.731919211 | TMEM17 | 0.487266629 | DAPK2 | 0.521285458 | | | | |
| LOC73246 | 0.731324172 | C22orf29 | 0.485679679 | NLRX1 | 0.518491497 | | | | |
| ABHD14A | 0.729919691 | WDR82 | 0.47897466 | GATAD2A | 0.515499364 | | | | |
| LOC729279 | 0.729691569 | C2orf15 | 0.477568944 | NR4A2 | 0.514797225 | | | | |
| RAPGEF6 | 0.729549364 | AK5 | 0.476192334 | JARID2 | 0.514354883 | | | | |
| C19orf53 | 0.728514239 | AKTIP | 0.474998212 | GATS | 0.499114393 | | | | |
| LOC44113 | 0.728397238 | ZBED3 | 0.474981147 | ARID4A | 0.492115532 | | | | |
| HSPB1 | 0.726571375 | SH3PXD2A | 0.46973856 | CHPF2 | 0.489985486 | | | | |
| GPN1 | 0.726566569 | NENF | 0.468411812 | EPN2 | 0.488233339 | | | | |
| SLC25A3 | 0.726435744 | TGIF1 | 0.467594838 | TMEM33 | 0.482944342 | | | | |
| POLR2G | 0.726261788 | ZNF559 | 0.465617668 | AGAP8 | 0.477844348 | | | | |
| SUMF2 | 0.726147864 | MMGT1 | 0.461621563 | ATP2B4 | 0.477783292 | | | | |
| GLTSCR2 | 0.725737593 | ZNF252 | 0.458778973 | DIAPH1 | 0.471135458 | | | | |
| LOC6473 | 0.724122215 | PRUNE | 0.457978567 | METTL9 | 0.469936938 | | | | |
| FBXO32 | 0.722432538 | LOC646836 | 0.457692454 | HSPA1L | 0.469749354 | | | | |
| TSGA14 | 0.719854653 | LDOC1L | 0.457631285 | LOC113383 | 0.468335258 | | | | |
| MDH2 | 0.718886435 | CRIP2 | 0.455459825 | KBTBD11 | 0.46717114 | | | | |
| RPS8 | 0.716652755 | ARRDC2 | 0.453694329 | BRPF3 | 0.465177555 | | | | |
| SEPW1 | 0.716486338 | AP2S1 | 0.452824193 | UBE3B | 0.461616795 | | | | |
| FAM3A | 0.715548165 | LRRC16A | 0.442652223 | CD3LB | 0.4557268 | | | | |
| MAL | 0.71483775 | CDC42SE2 | 0.439226622 | PAN3 | 0.455644279 | | | | |
| EIF3G | 0.713911847 | LARGE | 0.433862128 | TACC1 | 0.451198563 | | | | |
| LOC653737 | 0.713386474 | LOC642755 | 0.429488267 | RAB43 | 0.449652328 | | | | |
| LOC1129424 | 0.713323277 | LOC729985 | 0.427293919 | CLASP1 | 0.447777232 | | | | |
| PLCG1 | 0.712268761 | SERPINE2 | 0.426932499 | FLJ1916 | 0.445564612 | | | | |
| TMEM23 | 0.711859266 | LOC1128252 | 0.425642295 | PDPK1 | 0.444597997 | | | | |
| LYRM7 | 0.711826946 | LOC64634 | 0.422889942 | FAM65B | 0.44427143 | | | | |
| COMMD7 | 0.711479625 | RTKN2 | 0.421221582 | ARID1A | 0.442712377 | | | | |
| TECR | 0.711389973 | ZFP14 | 0.413753175 | DACH1 | 0.439734865 | | | | |
| C16orf3 | 0.696214995 | DECR2 | 0.392967984 | SREBF1 | 0.429394886 | | | | |
| PECI | 0.694839698 | ZNF24 | 0.39244688 | SRRM2 | 0.423932667 | | | | |
| LOC646688 | 0.694445665 | HPCAL4 | 0.392296965 | ZFYVE27 | 0.421452588 | | | | |
| C1orf151 | 0.691589944 | NT5DC3 | 0.385937142 | TAF4 | 0.418321979 | | | | |
| LOC72942 | 0.689981631 | SNORD18C | 0.377829771 | RNF13 | 0.417795315 | | | | |
| BTBD2 | 0.689831116 | C19orf39 | 0.377367974 | ZNF644 | 0.4159187 | | | | |
| LOC645515 | 0.6893317 | CNN3 | 0.374713277 | CCDC97 | 0.399889593 | | | | |
| SMPD1 | 0.688971964 | PDZD4 | 0.371554119 | MED31 | 0.392396434 | | | | |
| PPP1R2 | 0.688489262 | LOC652837 | 0.364795947 | NCRNA85 | 0.382898142 | | | | |
| NMT2 | 0.688136554 | KIAA226 | 0.361262176 | ANKRD12 | 0.382668594 | | | | |
| PPM1K | 0.687738718 | C2orf1 | 0.354822868 | LOC64235 | 0.382215946 | | | | |
| LOC731365 | 0.686367864 | C3orf1 | 0.354718283 | FNBP1 | 0.36114745 | | | | |
| RSL1D1 | 0.685958983 | LOC64331 | 0.354694241 | TWSG1 | 0.351262263 | | | | |
| EEF2 | 0.685894553 | PLD6 | 0.348358154 | AHNAK | 0.341474449 | | | | |
| PIN1 | 0.685299297 | GSTM3 | 0.347442317 | CMTM4 | 0.33968982 | | | | |
| MTCP1 | 0.684631822 | CBR3 | 0.322565348 | EPAS1 | 0.335925656 | | | | |
| LYRM4 | 0.683961594 | CAMSAP1L1 | 0.321123437 | FAM19A2 | 0.331599374 | | | | |

TABLE 1-continued

| GeneID_set 1 | Weights Set 1 | GeneID_set 1 | Weights Set 1 | GeneID_set 2 | Weights Set 2 | GeneID_set 3 | Weights Set 3 | GeneID_set 4 | Autism Dx Set 4 |
|---|---|---|---|---|---|---|---|---|---|
| LOC439949 | 0.682459967 | C21orf33 | 0.316181939 | BMPR2 | 0.265431535 | | | | |
| MOAP1 | 0.679537354 | ZNF773 | 0.294777162 | C5orf53 | 0.251347985 | | | | |
| NIP7 | 0.678675569 | POTEE | 0.294494551 | OR7E156P | −0.215227946 | | | | |
| IFFO2 | 0.677846416 | ELA1 | 0.293626752 | LOC1132493 | −0.281312391 | | | | |
| NUCB2 | 0.677791323 | SPNS3 | 0.28537988 | SIL1 | −0.286555239 | | | | |
| MAGEE1 | 0.677713541 | AKR1C3 | 0.27769758 | BCL2L11 | −0.341419371 | | | | |
| LOC1131662 | 0.677193155 | CCDC23 | 0.263623678 | UHRF2 | −0.354936336 | | | | |
| MRPS15 | 0.675764332 | GSTM2 | 0.257679191 | PARP15 | −0.37762429 | | | | |
| NOG | 0.675741187 | DNTT | 0.242897277 | SGOL2 | −0.411241473 | | | | |
| POLR3GL | 0.675617726 | ACSM3 | 0.241276627 | LOC644482 | −0.415712543 | | | | |
| RPL17 | 0.675285949 | ZNF683 | 0.231965799 | NCKAP1L | −0.418321587 | | | | |
| AK3 | 0.674199622 | LAPTM4B | 0.228282129 | HCFC1R1 | −0.449654339 | | | | |
| IL23A | 0.672979677 | C6orf16 | 0.225251342 | LOC92755 | −0.452596549 | | | | |
| ALDH5A1 | 0.671134823 | GSTM4 | 0.215359789 | BATF | −0.463729569 | | | | |
| ZNF54 | 0.667378217 | PFKFB3 | 0.213262843 | LOC729779 | −0.468574718 | | | | |
| SFRS2B | 0.667128489 | PEMT | 0.188677328 | ING3 | −0.479326333 | | | | |
| LOC649821 | 0.663376153 | TOX2 | 0.157468472 | LOC64746 | −0.51635382 | | | | |
| LPAR5 | 0.661938675 | LOC72949 | −0.198886269 | LOC644745 | −0.516637429 | | | | |
| ZNF792 | 0.661844441 | TROVE2 | −0.229347861 | SERPINB8 | −0.523912813 | | | | |
| CD4LG | 0.659346237 | MPDU1 | −0.236721729 | C15orf57 | −0.524154265 | | | | |
| LOC147727 | 0.658543639 | BRWD2 | −0.272935165 | SLC25A19 | −0.533627461 | | | | |
| FAM12A | 0.658423623 | ANKRD41 | −0.278587817 | GNG7 | −0.541637763 | | | | |
| SLC25A23 | 0.65773867 | WASH2P | −0.283377589 | CEPT1 | −0.568436894 | | | | |
| GLRX5 | 0.655646442 | ECT2 | −0.326623195 | RPS7 | −0.573623857 | | | | |
| HIGD2A | 0.654182518 | LGSN | −0.351114879 | MRPL41 | −0.578622978 | | | | |
| ZNF26 | 0.653666419 | CLEC12A | −0.35367923 | CCDC28B | −0.58366246 | | | | |
| NFX1 | 0.653548398 | LOC44264 | −0.384431314 | PSMB7 | −0.586314985 | | | | |
| NELL2 | 0.653478218 | AP1G1 | −0.389494962 | LOC644877 | −0.587312525 | | | | |
| NDUFB11 | 0.653473711 | ADCY7 | −0.427648158 | TCEB1 | −0.614147656 | | | | |
| CCDC65 | 0.651898138 | MIR1974 | −0.429379598 | CKS2 | −0.619366364 | | | | |
| ZNF518B | 0.651475739 | CTRL | −0.448386681 | THOC4 | −0.625798657 | | | | |
| TCEA2 | 0.649342463 | LOC42112 | −0.453281873 | LOC113181 | −0.636264657 | | | | |
| LOC113291 | 0.649229319 | ANXA2P3 | −0.457511395 | LOC7292 | −0.648413997 | | | | |
| PABPC4 | 0.649134234 | LOC1133875 | −0.459712358 | MRPL17 | −0.672451965 | | | | |
| EIF2S3 | 0.648894172 | HM13 | −0.461368312 | DBI | −0.689455395 | | | | |
| RPS18 | 0.646475474 | CD74 | −0.465298864 | LOC113932 | −0.717395773 | | | | |
| STAT4 | 0.646221522 | LILRA3 | −0.467695852 | ETFB | −0.734397533 | | | | |
| CCDC25 | 0.644689569 | ARHGAP3 | −0.469736658 | NUDCD2 | −0.74328978 | | | | |
| RPL8 | 0.644367573 | NLRC5 | −0.474588382 | TMEM126B | −0.757728329 | | | | |
| PGM2L1 | 0.643897977 | SULT1A2 | −0.482875287 | GTF3C6 | −0.795216188 | | | | |
| | | FKBP1A | −0.492172182 | | | | | | |
| | | JAM3 | −0.497945832 | | | | | | |
| | | FCGR2B | −0.514251626 | | | | | | |
| | | CLEC12B | −0.515195232 | | | | | | |
| | | TRPC4AP | −0.519258529 | | | | | | |
| | | C11orf82 | −0.521156625 | | | | | | |
| | | PTK2B | −0.524676726 | | | | | | |
| | | GPR65 | −0.525797342 | | | | | | |
| | | KLF5 | −0.527857833 | | | | | | |
| | | PKM2 | −0.539118323 | | | | | | |
| | | SAP3L | −0.539171373 | | | | | | |

TABLE 1-continued

| GeneID_set 1 | Weights Set 1 | GeneID_set 1 | Weights Set 1 | GeneID_set 2 | Weights Set 2 | GeneID_set 3 | Weights Set 3 | GeneID_set 4 | Autism Dx Set 4 |
|---|---|---|---|---|---|---|---|---|---|
| | | SULT1A3 | −0.547825718 | | | | | | |
| | | ANXA2P1 | −0.548762819 | | | | | | |
| | | NFKBIB | −0.558246324 | | | | | | |
| | | GDI1 | −0.561865494 | | | | | | |
| | | PSRC1 | −0.564178565 | | | | | | |
| | | HHEX | −0.583227669 | | | | | | |
| | | DIP2B | −0.594517957 | | | | | | |
| | | WWP2 | −0.614284312 | | | | | | |
| | | LOC42221 | −0.626577759 | | | | | | |
| | | SIGLEC7 | −0.627915225 | | | | | | |
| | | LOC1124692 | −0.6312228 | | | | | | |
| | | LILRA1 | −0.634928539 | | | | | | |
| | | MEF2A | −0.639317827 | | | | | | |
| | | HSH2D | −0.649436192 | | | | | | |
| | | CTSC | −0.655139391 | | | | | | |
| | | BIN2 | −0.655173425 | | | | | | |
| | | LSP1 | −0.668495558 | | | | | | |
| | | TNFSF13 | −0.67161967 | | | | | | |
| | | EFCAB2 | −0.682346884 | | | | | | |
| | | LOC113251 | −0.688489257 | | | | | | |
| | | ILK | −0.693325115 | | | | | | |
| | | HIST1H2AD | −0.695734597 | | | | | | |
| | | LOC648733 | −0.696389547 | | | | | | |
| | | C1orf58 | −0.712867866 | | | | | | |
| | | KDM1B | −0.718128564 | | | | | | |
| | | AQP12A | −0.724567526 | | | | | | |
| | | LOC65275 | −0.73677314 | | | | | | |
| | | ITGAX | −0.744397547 | | | | | | |
| | | IRF2 | −0.769235155 | | | | | | |
| | | AFF1 | −0.784337538 | | | | | | |

TABLE 1.1

| Top 50 genes of set 1 with absolute value of weights closer to 1 (highest weight from 0.818423753 to 0.935783593): | | | | | |
|---|---|---|---|---|---|
| CD3D | UXT RPS4X | LOC283412 | LOC127295 | LOC42694 | SKAP1 LOC72882 |
| | LOC645173 | RPL23A | LOC646942 | LOC646294 | LOC728428 |
| | LOC44737 | LOC7329 | LOC391833 | RPS3 RPL36 | LOC1127993 |
| | LOC73187 | LOC72831 | LOC653162 | LOC729679 | LOC441246 |
| | LOC387841 | C13orf15 | LOC728576 | EIF3K EEF1B2 | LCK |
| | LOC39345 | RPL4 LOC1132742 | EIF3H | CD27 RPS15 | LOC649447 |
| | LOC1131713 | LOC286444 | LOC729789 | RPL1A CD6 | LOC646766 |
| | C17orf45 | CUTA EIF3F | LOC642741 | LOC388339 | RPS14 LOC11398 |

TABLE 1.2

| Top 50 genes of set 2 with absolute value of weights closer to 1 (highest weight from 0.711353632 to 0.899346773): | | | | | | | | | | | |
|---|---|---|---|---|---|---|---|---|---|---|---|
| CUTL1 | MAST3 | | STK4 | KIAA247 | | MYH9 | RAPGEF2 | | ARAP3RAB11FIP1 | | |
| | WBP2 | GNAI2 | MTMR3 | | GTF3C6 | | CBL | UBE4BIGF2R | | YPEL3 | SETD1B |
| | PIK3CD | | RASSF2 | | KDM6B | | TP53INP2 | | NUAK2 | | PAK2 |
| | MYO9B | | NDE1 | TMEM126B | | IRS2 | PHF2 | MAP2K4 | | CAMK1D | |
| | NUDCD2 | | CDC2L6 | | ETFB | ASAP1 | TSC22D3 | | TLN1 ANXA11 | | |
| | EP3 | ROD1 | RXRA | RASSF5 | | PELI2 | SEMA4D | | LOC113932 | | PPM1A |
| | CREBBP | | LAPTM5 | | CABIN1 | | PLCB2 | WNK1 | | | |

TABLE 1.3

| Top 50 genes of set 3 with absolute value of weights closer to 1 (highest weight from 0.717268353 to 0.952217397) | | | | | | | | | |
|---|---|---|---|---|---|---|---|---|---|
| LOC44926 | ITM2B | HOXC6 | LOC392288 | | YIPF4 | RBMS1 | USP6 | | |
| | KIAA133 | LOC642567 | EVI2B | UBE2W | | DDX3X | | UBE2D1 | |
| | HIAT1 | TTRAPLOC44525 | C18orf32 | | LOC1132888 | | ROCK1 | | |
| | LOC64798 | FAM91A2 | SENP6 | LOC732229 | | CEP63 | ATG3 | LOC1128269 | |
| | PLAGL1 | MBD2 EXOC8MRRF | | LOC113377 | | POTE2 | C8orf33 | | |
| | LOC38953 | CPEB3 C6orf211 | | LOC1128533 | | LOC648863 | | STX7 | SEPT14 |
| | LOC4493 | LOC442319 NCRNA81 | | | CLEC7A | | CSNK1A1L | | |
| | LOC643896 | P74P LOC4948 | | GABARAPL2 | | FCGR3A | | | |

TABLE 1.4

| Top 50 genes of set 4 with absolute value of weights closer to 1 (highest weight from 0.53314 to 0.982476) | | | | | | | | | | |
|---|---|---|---|---|---|---|---|---|---|---|
| SDPR | PDE5A PTGS1 | CTDSPL | | CTTN | ALOX12 | | MPL | DNM3 | C1orf47 | |
| | C7orf41 | C5orf4 | RAB27B | | CXorf2 | GRAP2CDC14B | | | DAB2 | TAL1 |
| | NCALD | ITGB5 | GUCY1A3 | | FERMT3 | | TSC22D1 | | LIMS1 | SLC8A3 |
| | ABCC3HOMER2 | | NAT8BFBLN1 | | ARHGAP21 | | C21orf7 | | C15orf52 | |
| | CABP5 ENDOD1 | | SOCS4 C15orf26 | | | PVALB | | SLC24A3 | | HGD |
| | ZNF185 | CA2 | CXCL5 GRB14 | | VWF | DKFZp686I15217 | | | NDUFS1 | |
| | GRASPRGS18 | C16orf68 | | MGC135 | | LOC64926 | | HIST1H2AE | | |

In certain embodiments, normalized gene expression values of the signature genes in Table 1 can be used as is, thus without weighting, for the classification of ASD vs non-ASD. In certain embodiments, using Boosting (see Scoring and Classification methods) three lists of genes were identified with the smallest number of elements that classified subjects with accuracy of at least 70%, at least 75%, and at least 80%. Sets with 20, 25 and 30 features that can produce at least 70%, at least 75%, and at least 80% correct classification include but are not limited to those shown in Table 2 below. In certain embodiments, adjusting the weights of the genes based on the age of the subject is the most important single parameter for improving accuracy of ASD classification

TABLE 2

| Accuracy % | Minimum # of features | Gene list + AGE | | | | | | |
|---|---|---|---|---|---|---|---|---|
| 80% | 30 | "AGE" | AK3 | LOC100132510 | ARID4A | CMTM4 | KIAA1430 | LOC441013 |
| | | MAL | SETD1B | AKR1C3 | ATXN7L3B | PARP15 | AP2S1 | CA2 |
| | | PAN3 | MTMR3 | TOP1P2 | UHRF2 | LOC92755 | EPOR | MED31 |

TABLE 2-continued

| Accuracy % | Minimum # of features | Gene list + AGE | | | | | | |
|---|---|---|---|---|---|---|---|---|
| | | LOC389286 | LOC646836 | MSRB3 | GPR65 | SMPD1 | GPX4 | LOC100133770 |
| | | PRKCB | LOC100129424 | | | | | |
| 75% | 25 | "AGE" | FCGR3A | LOC389342 | IGF2R | ARAP3 | PDE5A | MPL |
| | | CUTL1 | LOC642567 | SDPR | PTGS1 | MIR1974 | MAP1LC3A | LILRA3 |
| | | LOC100133875 | SPI1 | LOC653737 | IRS2 | MAST3 | NCF1B | STK40 |
| | | KIAA0247 | LOC648863 | CTDSPL | NCALD | | | |
| 70% | 20 | "AGE" | IGF2R | ARAP3 | FCGR3A | LOC389342 | LOC648863 | SPI1 |
| | | LOC642567 | CUTL1 | PDE5A | ASAP1 | KIAA0247 | MAP1LC3A | ZNF185 |
| | | IRS2 | MTMR3 | LOC100132510 | IMPA2 | NCALD | MPL | |

The gene-networks signature matrix (GNSM) is a matrix containing weights and features calculated from gene-to-gene interaction patterns. These interaction patterns can also be calculated based on the relationship or state of a gene with non-genomic features.

The multi-modal signature matrix (MMSM), which is a matrix containing the quantification of non-genomic features obtained by clinical, behavioral, anatomical and functional measurements. In certain embodiments, the MMSM includes, but is not limited to, age, GeoPref Test[28], MRI/fMRI/DTI, and ADOS test.[29,30] Scores from questionnaires are also included in the MMSM for instance the CSBS test.[31]

The collateral features signature matrix (CFSM), which is a matrix containing any features that are not related to the subject under study. In certain embodiments, the CFSM includes, but is not limited to, analytes in maternal blood during pregnancy, sibling with autism, maternal genomic signature or preconditions, and adverse pre- or perinatal events.

In certain embodiments, the invention provides the use of the weighted gene signature matrix (WGSM) which is based for example on four sets of genes and gene-weights (Weight Sets 1-4, see Table 1) that predict autism with high accuracy. In some exemplary embodiments, the WGSM includes a total of 762 genes as listed above (see Table 1), 2 or more genes arranged in any number of sets can be included, as well. It is to be understood that the exact number of genes used in the method can vary as well as the type of genes based on the model derived from the Autism Reference Database.

In certain embodiments, the WGSM technology of the invention comprises the following steps:

Step 1: Collection of quality blood leukocyte samples and extraction of RNA from leukocytes. Blood leukocytes are collected from a newborn, infant, toddler or young child as part of a general pediatric screening procedure or as a diagnostic test for those at high risk for autism (such as younger siblings of an autistic child) or suspected to have autism. Temperature and history are taken and documented prior blood sample collection. Samples are collected if the child has no fever, cold, flu, infections or other illnesses or use of medications for illnesses 72 hours prior blood-draw. If a child has a fever, cold, etc, then blood samples should be collected no sooner than a week after the illness is over.

Four to six ml of blood is collected into EDTA-coated tubes. Leukocytes are captured and stabilized immediately (for instance via a LEUOLOCK filter, Ambion, Austin, Tex., USA) and placed in a −20 degree freezer for later processing.

mRNA is extracted from leukocytes according to standard practices. For example, if LEUKOLOCK disks are used, then they are freed from RNAlater and Tri-reagent is used to flush out the captured lymphocytes and lyse the cells. RNA is subsequently precipitated with ethanol and purified though washing and cartridge-based steps. The quality of mRNA samples is determined with RNA Integrity Number (RIN) assays and only values of 7.0 or greater are considered acceptable for use in the next steps. Quantification of RNA is performed using, as an example, Nanodrop (Thermo Scientific, Wilmington, Del., USA).

Step 2: Determination of gene expression levels for genes used in the Weighted Gene Test of Autism. Whole-genome gene expression levels are obtained by using either a microarray-based platform (such as Illumina HT-12 or equivalent) or next-generation sequencing. The analysis of gene expression levels can also be performed using a targeted approach based on custom microarrays, targeted sequencing or PCR-based amplification of the WGSM and/or gene-networks signature matrix (GNSM) genes (see below Gene Expression Profiling).

Whichever method is used, however, it should provide high fidelity expression levels for each of the genes in the WGSM. This is achieved by using methods that interrogate the signal intensity and distribution of each probe/gene. For instance, a detection call p-value of 0.01 is used as the threshold to filter out probes/genes with expression levels of poor quality. For analyses performed on multiple subjects simultaneously, any probe/gene with no detectable levels in at least one subject is also eliminated. Once the final set of probes/genes with high fidelity expression levels is determined, the data is transformed (for instance with the "log 2" function) and normalized. The normalization step is helpful in order to obtain informative and comparable expression levels to the weighted gene expression reference database.

In certain embodiments, the weighted gene feature test of autism (WGFTA) technology utilizes the simultaneous analysis of at least 20, 40, 80, 150 or more subjects (recruited and processed with similar criteria of the reference dataset discussed below) for independent normalization. In the case of fewer subjects, these subjects can be added to the reference database prior to normalization. Normalization can then be performed using for instance the "quantile" method.

At the conclusion of Step 2, the normalized gene expression value (NGEV) for an individual subject or patient has been determined for each gene in the WGM. In some embodiments, one or more NGEVs are used to classify genes for use in the methods of the invention without further using a gene-specific weight. In certain embodiments, the NGEVs are used with MMSM and/or CFSM values. In alternative embodiments, the NGEVs are used without MSSM and/or CFSM values.

Step 3: The procedure in the weighted gene feature test of autism (WGFTA) involves application of the gene-specific weights from the weighted gene signature matrix to the NGEV in each child. For each gene in the WGSM, its NGEV is multiplied by that gene's gene-specific weight (for example, see Table 1). The resultant value for each gene is the weighted gene expression level. In certain embodiments, the genes in the representative example Weights Sets 1-4 constitute the genes in the WGSM and used in the WGFTA.

The weighted gene expression levels in a subject's (or patient's) sample can be further processed to reduce dimensionality using methods such as principal component analysis (PCA) or eigenvalues or multi-dimensional scaling (MDS). This step reduces computation time, data noise and increases power in the subsequent analysis steps, while it preserves the biological information useful for the classification. If computation power, time and data noise is not an obstacle, then the weighted gene expression level data in each subject or patient can be used as is in the next step.

Step 4: the second procedure in the weighted gene feature test of autism (WGFTA) is the comparison of weighted gene expression levels to a unique autism and control weighted gene expression reference database. The subject or patient's set of weighted gene expression levels is compared to the specific multidimensional weighted gene expression reference database to establish a score for autism risk and/or a class identity (ASD, non ASD). Two different scoring or CLASS identity methods are applied (see below).

In certain embodiments, the performance of the invention includes: the prediction accuracy of the weighted reference database, the ROC curves with estimated AUC, Accuracy, Specificity, Sensitivity and the matrix of weights for the identified gene-sets. See FIGS. 4C and 4D (Logistic regression analysis and classification outcome of the weighted reference database) and Table 1.

Scoring/CLASS Identity Methods

In certain embodiments, the following scoring methods are used. However, any available scoring methods, now known or later developed, are encompassed within the scope of the invention.

In certain embodiments, methods use boosted classification trees to build the screening, diagnostic and prognostic classifiers, with or without the use of modules to classify the genes. This classification regime is divided into two main components. First, the underlying classification algorithm is a classification tree. Second, boosting is applied to this baseline classifier to increase the prediction strength. The resulting learning algorithm retains the strengths of the baseline classifier while improving the overall predictive capability. In particular embodiments, there are two classes, ASD and non-ASD; the classes are represented symbolically by +1 and −1. The training dataset consists of labeled cases $(x_1, y_1), (x_2, y_2), \ldots, (x_N, y_N)$. Here, $y_i$ is a class label and $x_i$ is vector of variables or features measured for the i-th individual. A classifier is represented by a function C(x) whose input is a vector x in the feature space and whose output is one of the class labels.

Figure 15:
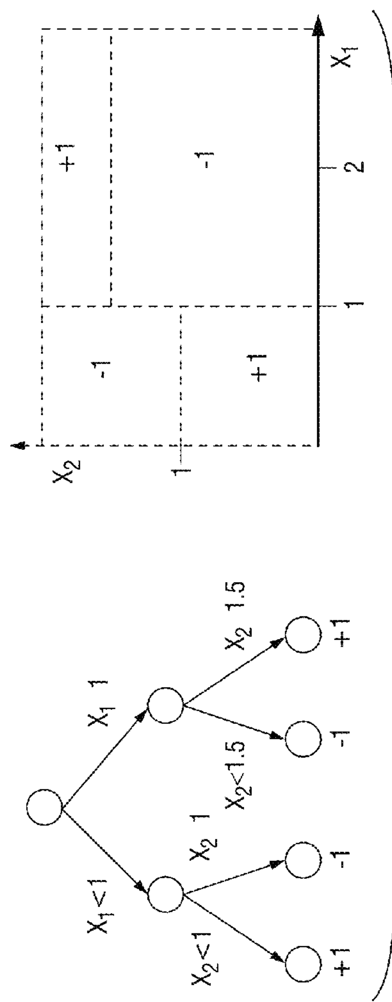
FIG. 15. Diagram representing the splits of decision tree classification (left panel) for ASD (+1) and control (−1) and the feature space that is recursively divided into finer sub-regions accordingly to the number of feature used (right panel).

In the first component, namely classification trees, the underlying learning algorithm used is a decision tree for classification. Any classifier can be represented by a partition of the feature space into disjoint regions $R_1, R_2, \ldots, R_k$ and associated labels $c_1, c_2, \ldots, c_k$. The class of a new, unlabeled case is predicted by locating the region into which the feature coordinates of the case falls and reading off the class label for that region. In a decision tree, this partition is represented by the leaf nodes in a binary tree (see FIG. 15). Starting at the root of the tree, each node represents a subdivision of a region of the feature space by splitting it on one of the variables. The feature space is thus recursively divided into increasingly finer sub-regions. The "leaf" nodes at the bottom of the tree are affixed with class labels. The best partition for classification is learned from the data: for a given node, the variable from the full feature set and the threshold value for that variable that best separate the data into its constituent classes is selected, producing two child nodes. The selection is based on maximizing some measure of fitness of the resulting classifier, such as the information gain. The process is repeated for each node until a halting criterion is reached, such as when all of the training data points in a given sub-region are of the same class.

Figure 16:
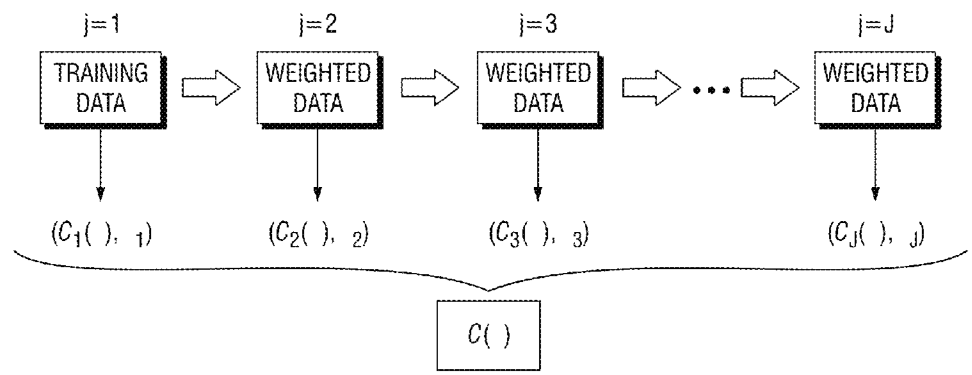
FIG. 16. Diagram representing the boosting algorithm (for example AdaBoost) by fitting a baseline classifier and using its performance on the training data to re-weight the importance of each point in subsequent fits.
Figure 17:
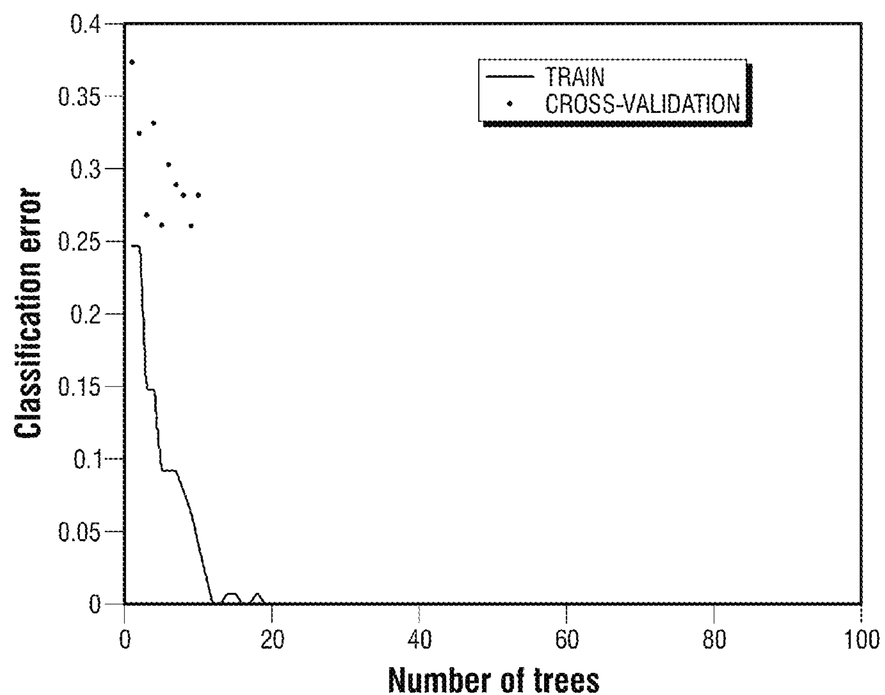
FIG. 17. Boosting classification performance using 25 genes of the signature matrix. The cross-validation error is about 25%, thus giving a classification accuracy of 75%.

Then, in the second component, namely boosting, the classification tree is improved using a boosting algorithm (such as AdaBoost). This algorithm works by iteratively fitting a baseline classifier and using its performance on the training data to re-weight the importance of each point in subsequent fits (see FIG. 16). Initially, each of the data points is given equal weight. After fitting the classifier, the error rate on the training data is used to produce a weight α associated with the classifier. The weights of the data points are then updated: the weights of misclassified points are increased while correctly labeled points are de-emphasized. This forces the next classifier to pay more attention to cases where errors were previously made. The process is repeated using the re-weighted observations in the next iteration; it halts when the test error—computed from a test data set or via cross validation—has stabilized, or when a fixed number of iterations has been reached. Formally, the algorithm proceeds as follows. Let $w_i$ be the weight of the i-th training point, $i=1, \ldots, N$. Initialize the weights as $w_i=1/N$. For $j=1, \ldots J$, do the following:

1. Fit the classifier $C_j(x)$ to the weighted data set.
2. Compute the weighted training error rate $e_j=\Sigma_{i=1}^{N}w_iI(y_i\neq C_j(x_i))/\Sigma_{i=1}^{N}w_i$.
3. Compute the weight $\alpha_j=\ln((1-e_j)/e_j)$.
4. For each i, update the weights according to $w_i \leftarrow w_i \times e^{\alpha_j I(y_i \neq C_j(x_i))}$.

The result is a sequence $(C_1(x), \alpha_1), (C_2(x), \alpha_2), \ldots, (C_J(x), \alpha_J)$ of classifiers and associated weights. The sequence is combined into a final classifier by taking the sign of a weighted sum of the sequence: $C(x)=\mathrm{sign}(\Sigma_{j=1}^{J}\alpha_jC_j(x))$.

In other embodiments, an alternative to the tree-based classifier can be used such as distance-based methods that utilize distances in the feature space in order to predict the class labels. The procedure can quantify the extent to which a given set of features conforms to each of the classes, and predicts the label of the class with the highest concordance. For each class, the mean vector μ and covariance matrix Σ of the feature distribution is estimated using the sample mean and sample covariance matrix. Then, for a given point x in the feature space, the Mahalanobis distance between the x and the mean $d=((x-\mu)^T\Sigma^{-1}(x-\mu))^{1/2}$ is computed. The predicted label for x is the label corresponding to the class that minimizes this distance. The performance of the resulting classifier can then be improved by using it as the baseline classifier in the boosting procedure outlined above.

With multiple feature sets, the model detailed here can be fit using a wide range of features for prediction. In some instances, only certain types of features may be available at the time of prediction. For example, only gene expression signatures and age might have been observed for a particular patient. The model can be fit using various combinations of feature modalities from the MMSM and CFSM as well as GNSM. The result is a suite of classifiers, each one suited to a different configuration of feature types. This yields a classification procedure that can be utilized for a range of patient data availabilities and thus is robustly useful in the applied setting.

Performance of the WGSM was tested with several algorithms including, but not limited to, Random Forest-, Neural Network-, Support Vector Machine-, Boosting- and Logistic Regression-based methods and independently validated on a second dataset of autism and non-autism subjects. This testing showed high-accuracy in diagnostic classification of autism (80% or greater classification accuracy), thus confirming: 1) the efficacy and specificity of a unique pattern of gene weights, 2) the relevance, sensitivity and specificity of the identified four sets of genes, and 3) the reliability of the multi-dimensional weighted reference of autism and control.

Score calculation and class prediction are generated by the computer-based algorithms selected to test the WGSM on the new subject(s) (see previous paragraphs). A comparison of matrices is performed by using distance-based classification between the new subject(s) matrices and the referenced matrices from both the ASD and control subjects.

Gene Expression Profiling

The invention enables the use of both genome-wide and gene targeted approaches to quantify gene expression levels of peripheral blood leukocyte of a test subject. As used herein, the Genome-wide approaches include, but are not limited to, the use of microarray-based platforms and next-generation sequencing. Expression levels of the genes belonging to the WGSM are extracted after standard normalization, transformation and filtering steps (see Methods in the Examples below). As used herein, the Gene-targeted approaches include, but are not limited to, microarray-based platforms or PCR-based amplification.

With the targeted approaches only the expression levels of the genes belonging to the WGSM are determined. The use of whole-genome microarrays requires an a priori construction of a gene-library or the use of a gene-capturing method. Alternatively, the targeted approach via microarray-based platform is done by the construction of custom-designed gene expression microarrays containing only the genes from the four gene-sets with control and reference probes and replicated on the same platform to allow high reproducibility and testing of multiple patients. Gene expression levels are then calculated with the use of control probes, reference genes and/or experiments.

WGSM Features:

1) Signature gene composition: The provided example of the WGSM includes 762 genes. However, any 2 or more genes can be assayed on different platforms, array-based, sequencing based or PCR-based.
2) Splice variants information of the genes within the WGSM is also used.
3) Data redaction tools are also applied to the genes of the WGSM.

In some embodiments, the invention provides that the WGSM can be used alone in the Weighted Gene Feature Tests of Autism (WGFTA) or in combination with one or more of the other matrices described above. In certain embodiments, the combination use of the WGSM with subject's age as Multi-Modal Signature Matrix (MMSM) is provided.

A major strength of the signature discovery was the recruitment of subjects using a general, naturalistic population screening approach. This approach allowed the unbiased, prospective recruitment and unique study of autism and contrast patients as they occur in the community pediatric clinics. To maximize the number of ASD and control subjects for the signature discovery, a slight age difference is tolerated in the two subject distributions and age is included as a predictor in the classification analysis. The impact of all predictors was then assessed in the classification of the subjects by logistic regression with binomial distribution. The output of these analyses is provided as follows:

a) Analysis using age as the only predictor of diagnosis showed a very small ODDS ratio of 1.07 towards the ASD CLASS.
b) Analysis using the Weights Sets 1-4 as predictor singularly showed ODDS ratios (9577.88, 17423.52, 4.16e-05 and 3716.94 respectively).
c) Analysis using all predictors together (Weights Sets 1-4 and age) showed again very large ODDS ratios for the Weights Sets 1-4 predictors (1.73e+06, 1.46e+05, 5.31e-03 and 6.235152e+01 respectively) and an ODDS ratio close to 1 for age (1.089). Using different algorithms, classification performance improved on average by 3-4% (see Table 3).

TABLE 3

Classification performance using different algorithms with and without age as predictor

| Algorithm Name | % Accuracy without AGE discovery set | % Accuracy without AGE replication set | % Accuracy with AGE discovery set | % Accuracy with AGE replication set |
|---|---|---|---|---|
| glmnet | 78 | 72 | 82 | 75 |
| mlp | 78 | 72 | 83 | 69 |
| cforest | 87 | 70 | 91 | 72 |
| svm radial | 81 | 68 | 87 | 70 |
| random forest | 100 | 70 | 100 | 67 |
| qvnnet | 84 | 65 | 84 | 71 |

It is known that the transformation from ODDS values to probability is a monotonic transformation following an exponential curve. An ODDS ratio of 1 indicates a 0.5 probability to fall into either CLASS, in this case ASD and non-ASD. An ODDS value tending to infinity or zero indicates a very high or very low probability, respectively, to be classified ASD. Therefore, it is demonstrated that although age effects are present in this study, they are very small considering the effects of the gene expression signature predictors (Weights Sets 1-4 in Table 1). Moreover, this effect is empirically quantified by classification of both discovery and replication subjects with and without age as a predictor. It was found that classification accuracy increased by about 3-4% or more when age was included as a predictor in the analysis, and so in certain embodiments, the invention uses age as a predictor in screening, diagnostic and prognostic signatures of ASD, as shown in one Example 3 below.

Similarly, additional predictors from the MMSM which includes non-genomic quantifiable features obtained by clinical, behavioral, anatomical and functional measurements. In certain embodiments, clinical features are scores on the ADOS, Mullen, Vineland, and any other diagnostic and psychometric test instruments. In certain embodiments, neurobehavioral features are eye-tracking tests such as the GeoPreference Test of autism and exploration tests. In certain embodiments, anatomical features are MRI neuroanatomical measures including, but not limited to, global and regional gray or white matter volumes, cortical surface areas or thickness and cortical gyrification as determined by methods including, but not limited to, voxel-based, statistical mapping-based and surface or structure reconstruction based methods (e.g., temporal grey matter volumes, and DTI measures including tract fractional anisotropy (FA) and volume and gyral patterns of cortical tract projections).

In certain embodiments, the functional features are fMRI measures including, but not limited to, activation, psychophysiological (PPI), dynamic causal modeling, unsupervised classification information maps and values. Similarly features from the GNSM and CFSM are used with or without the WGSM as predictors in the classification and prognostic analyses.

Therefore, the invention in some embodiments utilizes a test based on a specific pattern of specific-gene weights in a person that are involved in governing cell cycle, DNA damage response, apoptosis, protein folding, translation, cell adhesion and immune/inflammation, signal transduction ESR1-nuclear pathway, transcription-mRNA processing, cell cycle meiosis, cell cycle G2-M, cell cycle mitosis, cytoskeleton-spindle microtubule, and cytoskeleton-cytoplasmic microtubule functions. The WGFTA provided by the invention requires high quality molecular components, including RNA, genomic DNA, cellular and serum proteins, and small molecule analytes, that are extracted by clinically standard methods from blood and other tissues collected using clinically routine methods from ages of birth to 1 year, 1 year to 2 years, 2 years to 3 years and 3 years to 4 years. The present invention provides that the DNA and/or mRNA can be collected in many ways and/or isolated or purified directly from a biological tissue or cell sample, including but not limited to tears, saliva, mucous, buccal swab, whole blood, serum, plasma, cerebrospinal fluid, urine, and the like, or cells including, but not limited to fibroblasts, iPS cells, neuroprogenitor cells derived from iPS cells, and neurons derived from iPS cells, etc. A biological sample could also be obtained from specific cells or tissue, or from any secretions or exudate. In certain embodiments, the biological sample is a biological fluid obtained from peripheral blood. In certain embodiments, DNA is isolated or purified from peripheral blood nuclear cells (PBMCs) derived from fresh blood. Techniques for purification of biomolecules from samples such as cells, tissues, or biological fluid are well known in the art. The technique chosen may vary with the tissue or sample being examined, but it is well within the skill of the art to match the appropriate purification procedure with the test sample source.

In some embodiments, the WGFTA of the invention uses any one of several known and state-of-the-art whole genome RNA-based/gene expression assay (such as RNA sequencing, custom gene expression arrays, PCR-based assays, state-of-the-field whole genome microarrays or genome sequencing) that give accurate expression levels. In some embodiments, the WGFTA is based on gene sets such as, for example the four sets: Weights Set 1, Weights Set 2, Weights Set 3 and Weights Set 4 in Table 1. In certain embodiments, the WGFTS includes specific splice variants of the genes. In some embodiments, the Weighted Gene Matrix comprises genes in the WGFTA and their Gene-Specific Weights (see Table 1). Furthermore, in certain embodiments, the autism-critical weighted gene expression levels is the transformation of an individual's normalized expression levels of the genes in the weighted gene signature matrix by gene-wise multiplication of the gene-specific weights.

Depending upon the factors unique to each case and desired level of specificity and accuracy, any number of genes may be selected, for example, from those described in Table 1. In some embodiments, the genes are generally ranked according to relative importance based on the absolute value of the weight. In certain embodiments, the number of genes chosen includes at least 10, 20, 25, 30, 35, 40, 50, 60, 70, 80, 90, 100, 110, 120, 130, 140, 150, 160, 170, 180, 200, 210, 220, 230, 240, 250, 260, 270, 280, 290, 300, 350, 400, 450, 500, 550, 600, 650, 700, 750 or more genes, including intervening and greater numbers, within a selected gene set.

In certain embodiments, the invention of the WGFTA is (a) the application of the unique gene-specific weights to an individual's normalized gene expression values for those genes in order to derive that individual's autism-critical weighted gene expression levels; (b) the application of any subset of the unique Gene-Specific Weights derived from the effort in optimizing the classification performance of the Weighted Gene and Feature Test of Autism; (c) the modification of the Weights in the Weighted Gene Signature Matrix as the result of the optimization of the Autism and non-autism Weighted Gene Expression Reference Database from which the WGM is derived; (d) the comparison of an individual's Autism-Critical Weighted Gene Expression Levels to the Autism and not-autism Weighted Gene Expression Reference Database; and (e) the development and use of any RNA-based assay that uses the Weighted Gene Signature Matrix to test risk for autism.

In some embodiments, the invention also provides that the development and use of any RNA-based gene expression data combine with MMSM measures (for example anatomical and/or functional brain measurements) to screen for autism risk or diagnostically classify autism and other developmental disorders. For example, in certain embodiments, age is considered in conjunction with a subject's gene expression levels and as a predictor (for example see Scoring/CLASS identity methods above) in adjusting and/or improving screening for autism risk, autism diagnostic classification and prognosis analysis, and the WGFTA is based on the comparison of an autistic subject(s) to a non-autistic subject(s). Further, the use of the GeoPreference test score, CSBS (communication and symbolic behavior scales) test scores and genomic DNA (CNV, SNV, indel) markers in combination with expression signatures (for example in one embodiment of the method described in Scoring/CLASS identity methods above) increase the WGFTA performance and improve classification of autism and other developmental and neuropsychiatric disorders.

In some embodiments, the autism and non-autism reference database provided by the invention comprises the collection of Gene Expression Levels, Weights and all non-genomic features already described that were uniquely derived from the fully clinically characterized and diagnostically confirmed infants, toddlers and young children with autism, typically developing (TD), and non-autism non-TD subjects.

Therefore, the weighted gene and features tests of autism (WGFTA) provided by the invention can in some embodiments be used in pediatric population screens for risk of autism and in clinical follow-up diagnostic and prognostic evaluations of newborns, infants, toddlers, and young children who are suspected to be at risk for autism. Some attributes of the invention are based on analyses of in vivo functional genomic abnormalities in mRNA expression from blood leukocytes as they relate to the measures of brain and cerebral size and to mRNA expression patterns in typically developing controls. Thus, in certain embodiments the invention is based on direct experimental knowledge of the functional genomic defects and the resulting brain size relationships that are disrupted in autistic toddlers as compared to control subjects.

REFERENCES

1. Developmental Disabilities Monitoring Network Principal Investigators. Prevalence of autism spectrum disorders—Autism and Developmental Disabilities Monitoring Network, 14 sites, United States, 2008. *MMWR Surveill Summ* 61, 1-19 (2012)

2. Huttenlocher, P. R. Dendritic and synaptic development in human cerebral cortex: Time course and critical periods. *Developmental Neuropsychology* 16, 347-349 (1999).
3. Huttenlocher, P. R. & Dabholkar, A. S. Regional differences in synaptogenesis in human cerebral cortex. *Journal of Comparative Neurology* 387, 167-78 (1997).
4. Pierce K, Carter C, Weinfeld M, et al. Detecting, studying, and treating autism early: the one-year well-baby check-up approach. The Journal of pediatrics 2011; 159:458-65 e1-6.
5. Wetherby A M, Brosnan-Maddox S, Peace V, Newton L. Validation of the Infant-Toddler Checklist as a broadband screener for autism spectrum disorders from 9 to 24 months of age. Autism 2008; 12:487-511.
6. Pandey J, Verbalis A, Robins D L, et al. Screening for autism in older and younger toddlers with the Modified Checklist for Autism in Toddlers. Autism 2008; 12:513-35.
7. Kleinman, J. M. et al. The modified checklist for autism in toddlers: a follow-up study investigating the early detection of autism spectrum disorders. *J Autism Dev Disord* 38, 827-39 (2008).
8. Chlebowski, C., Robins, D. L., Barton, M. L. & Fein, D. Large-scale use of the modified checklist for autism in low-risk toddlers. *Pediatrics* 131, e1121-7 (2013).
9. Zwaigenbaum L, Bryson S, Rogers T, Roberts W, Brian J, Szatmari P. Behavioral manifestations of autism in the first year of life. Int J Dev Neurosci 2005; 23:143-52.
10. Ozonoff S, Young G S, Carter A, et al. Recurrence risk for autism spectrum disorders: a Baby Siblings Research Consortium study. Pediatrics 2011; 128:e488-95.
11. Paul R, Fuerst Y, Ramsay G, Chawarska K, Klin A. Out of the mouths of babes: vocal production in infant siblings of children with ASD. J Child Psychol Psychiatry 2011; 52:588-98.
12. Landa R, Garrett-Mayer E. Development in infants with autism spectrum disorders: a prospective study. Journal of child psychology and psychiatry, and allied disciplines 2006; 47:629-38.
13. Abrahams B S, Geschwind D H. Advances in autism genetics: on the threshold of a new neurobiology. *Nature reviews. Genetics.* 2008; 9:341-355.
14. Chow M L, Pramparo T, Winn M E, et al. Age-dependent brain gene expression and copy number anomalies in autism suggest distinct pathological processes at young versus mature ages. PLoS Genet. 2012; 8(3):e1002592.
15. Devlin B, Scherer S W. Genetic architecture in autism spectrum disorder. *Current opinion in genetics & development*. June 2012; 22(3):229-237.
16. Courchesne E, Pierce K, Schumann C M, et al. Mapping early brain development in autism. *Neuron.* 2007; 56:399-413.
17. Stanfield A C, McIntosh A M, Spencer M D, Philip R, Gaur S, Lawrie S M. Towards a neuroanatomy of autism: a systematic review and meta-analysis of structural magnetic resonance imaging studies. *European psychiatry: the journal of the Association of European Psychiatrists*. June 2008; 23(4):289-299.
18. Courchesne E, Mouton P R, Calhoun M E, et al. Neuron number and size in prefrontal cortex of children with autism. *JAMA*. Nov. 9, 2011; 306(18):2001-2010.
19. Courchesne E, Karns C M, Davis H R, et al. Unusual brain growth patterns in early life in patients with autistic disorder: an MRI study. *Neurology.* 2001; 57:245-254.
20. Glatt S J, Tsuang M T, Winn M, et al. Blood-based gene expression signatures of infants and toddlers with autism. J Am Acad Child Adolesc Psychiatry 2012; 51:934-44 e2. And also
21. Kong S W, Collins C D, Shimizu-Motohashi Y, et al. Characteristics and predictive value of blood transcriptome signature in males with autism spectrum disorders. *PloS one.* 2012; 7(12):e49475.
22. O'Roak, B. J. et al. Multiplex targeted sequencing identifies recurrently mutated genes in autism spectrum disorders. *Science* 338, 1619-22 (2012).
23. Klin, A., Lin, D. J., Gorrindo, P., Ramsay, G. & Jones, W. Two-year-olds with autism orient to non-social contingencies rather than biological motion. Nature 459, 257-61 (2009).
24. Jones, W., Carr, K. & Klin, A. Absence of preferential looking to the eyes of approaching adults predicts level of social disability in 2-year-old toddlers with autism spectrum disorder. *Arch Gen Psychiatry* 65, 946-54 (2008).
25. Shic, F., Bradshaw, J., Klin, A., Scassellati, B. & Chawarska, K. Limited activity monitoring in toddlers with autism spectrum disorder. *Brain Res* 1380, 246-54 (2011).
26. Bedford, R. et al. Precursors to Social and Communication Difficulties in Infants At-Risk for Autism: Gaze Following and Attentional Engagement. *J Autism Dev Disord* (2012).
27. Chawarska, K., Macari, S. & Shic, F. Context modulates attention to social scenes in toddlers with autism. *J Child Psychol Psychiatry* 53, 903-13 (2012).
28. Pierce, K., Conant, D., Hazin, R., Stoner, R. & Desmond, J. Preference for geometric patterns early in life as a risk factor for autism. *Archives of General Psychiatry* 68, 101-9 (2011).
29. Luyster, R. et al. The Autism Diagnostic Observation Schedule-toddler module: a new module of a standardized diagnostic measure for autism spectrum disorders. *J Autism Dev Disord* 39, 1305-20 (2009).
30. Lord, C. et al. The Autism Diagnostic Observation Schedule—Generic: A Standard Measure of Social and Communication Deficits Associated with the Spectrum of Autism. in *Journal of autism and developmental disorders* Vol. 30 205-223-223 (Springer Netherlands, 2000).
31. Wetherby A M, Allen L, Cleary J, Kublin K, Goldstein H. Validity and reliability of the communication and symbolic behavior scales developmental profile with very young children. Journal of speech, language, and hearing research: JSLHR 2002; 45:1202-18.
32. Burrier et al, INSAR abstract, 2013.

EXAMPLES

Example 1

Disrupted Gene Networks in Autistic Toddlers Underlie Early Brain Maldevelopment and Provide Accurate Classification Genetic mechanisms underlying abnormal early neural development in toddlers with Autism Spectrum Disorder (ASD) remain unknown, and no genetic or functional genomic signatures exist to detect risk for ASD during this period. The objective in this example was to identify functional genomic abnormalities underlying neural development and risk signatures in ASD.

A general naturalistic population screening approach was used to allow prospective, unbiased recruitment and study of ASD and control (typically developing and contrast) toddlers from community pediatric clinics. Whole-genome leukocyte expression and MRI-based neuroanatomic measures were analyzed in a discovery sample of 142 males ages 1-4 years. Co-expression analyses were applied to identify gene modules associated with variations in neuroanatomic measures and a candidate genomic signature of ASD. Class comparison and network analyses were used to identify dysregulated genes and networks in ASD toddlers. Results were compared to a Replication sample of 73 toddlers.

Correlations of gene expression profiles with deviation in neuroanatomic measures from normative values for age were performed in ASD and control toddlers. Classification performance was tested using logistic regression and ROC analysis. Cell cycle and protein folding gene networks were strongly correlated in control toddlers with brain size, cortical surface area, and cerebral gray and white matter, but weakly correlated in ASD. ASD toddlers instead displayed correlations with an abnormal array of different gene networks including immune/inflammation, cell adhesion, and translation. DNA-damage response and mitogenic signaling were the most similarly dysregulated pathways in both Discovery and Replication samples. A genomic signature enriched in immune/inflammation and translation genes displayed 75-82% classification accuracy.

The functional genetic pathology that underlies early brain maldevelopment in ASD involves the disruption of processes governing neuron number and synapse formation and abnormal induction of collateral gene networks. The orderly correlation between degree of gene network dysregulation and brain size, suggest there may be a common set of underlying abnormal genetic pathways in a large percentage of ASD toddlers. Knowledge of these will facilitate discovery of early biomarkers leading to earlier treatment and common biological targets for bio-therapeutic intervention in a majority of affected individuals.

Significant advances have previously been made in understanding the genetic[1-3] and neural bases[4-6] of autism spectrum disorder (ASD). However, establishing links between these two fundamental biological domains in ASD has yet to occur. Clinical macrocephaly at young ages occurs in an estimated 12% to 37% of patients, but a subgroup has small brain size. However, genetic explanations for this wide variation remain uncertain. Moreover, genetic signatures of risk for ASD in infants and toddlers in the general pediatric clinic have not yet been found.

A long-theorized brain-gene link is supported by new ASD postmortem evidence, at least in ASD with brain enlargement. The theory[7] is that early brain overgrowth, which occurs in the majority of ASD cases[4,5,8-12], may result from overabundance of neurons due to prenatal dysregulation of processes that govern neurogenesis, such as cell cycle, and/or apoptosis. A recent postmortem study discovered overabundance of neurons in prefrontal cortex, a region that contributes to autistic symptoms, in ASD children with brain enlargement[6], and a second postmortem study reported abnormal gene expression in cell cycle and apoptosis pathways also in prefrontal cortex in ASD male children[2]. Gene pathways identified in the latter ASD postmortem study are consistent with those identified by CNV pathway enrichment analyses in living ASD patients[13]. A complementary theory is that synapse abnormalities may also be involved in ASD[14], but how this may relate to early brain growth variation is unknown. Because direct analyses of brain-genome relationships during early development have never been done in ASD, it remains unknown whether genetic dysregulation of cell cycle, apoptosis and/or synapse processes underlie variation in brain growth and size in the majority of ASD toddlers. Since neuron number and synapse formation and function are developmentally foundational and drive brain size, common pathways leading to ASD may involve their dysregulation.

A novel study of genomic-brain relationships in vivo was performed in ASD and control toddlers. Unique to this study was that all toddlers came from a general naturalistic population screening approach that allows for the unbiased, prospective recruitment and study of ASD, typically developing (TD) and contrast toddlers as they occur in community pediatric clinics. Unbiased data-driven bioinformatics methods were used to discover functional genomic abnormalities that are correlated with brain anatomy at the age of clinical onset in ASD and distinguish them from TD and contrast toddlers. With this naturalist general population approach, it is also able to test whether some functional genomic abnormalities might also provide candidate diagnostic signatures of risk for ASD at very young ages.

Methods

Subjects, Tracking and Clinical Measures

Participants were 215 males ages 1-4 years. 147 toddlers were in a Discovery sample (N=91 ASD, 56 control) and 73 (N=44 ASD, 29 control) in a Replication sample. Toddlers were recruited via the 1-Year Well-Baby Check-Up Approach from community pediatric clinics[15] (see Methods in Example 2) that enables a general naturalistic population screening approach for prospective study of ASD, typically developing subjects and contrast patients. In this approach, parents of toddlers completed a broadband developmental screen at their pediatrician's office, and toddlers were referred, evaluated and tracked over time. This provided an unbiased recruitment of toddlers representing a wide range and variety of ability and disability. Blood samples for gene expression, DNA analysis and MRI brain scans were collected from a subset of subjects at time of referral, regardless of referral reason, and before final diagnostic evaluations. Every subject was evaluated using multiple tests including the appropriate module of the Autism Diagnostic Observation Schedule (ADOS)[16,17] and the Mullen Scales of Early Learning[18]. Parents were interviewed with the Vineland Adaptive Behavior Scales[19] and a medical history interview. Subjects younger than 3-years of age at the time of blood draw were longitudinally diagnostically and psychometrically re-evaluated every 6-12 months until their 3$^{rd}$ birthday, when a final diagnosis was given. Subjects were divided into two study groups: ASD and control. The control group was comprised of typically developing (TD) and contrast (e.g., language, global developmental or motor delay) toddlers (Table 4).

TABLE 4

| Summary of subject characteristics and clinical information | | | | | | |
|---|---|---|---|---|---|---|
| | Discovery | | | Replication | | |
| Subjects Characteristics | ASD | TD | Contrast | ASD | TD | Contrast |
| Age in years - Mean (SD) | 2.3 (0.7) | 2.0 (0.9) | 1.5 (0.6) | 2.3 (0.8) | 1.6 (0.7) | 1.2 (0.2) |
| AD | 77 | | | 31 | | |
| TD | | 41 | | | 25 | |
| PDD-NOS | 10 | | | 13 | | |
| Language Delayed ‡ | | | 9 | | | 2 |
| Globally Developmentally Delayed⁝ | | | | | | 1 |
| Radiological abnormality | | | 1 | | | 1 |
| Premature birth, testing normally“ | | | 2 | | | |
| Socially Emotionally Delayed‹‹ | | | 1 | | | |
| Drug Exposure₪ | | | 1 | | | |
| Ethnicity | | | | | | |
| Hispanic | 24 | 5 | 2 | 13 | 3 | 1 |
| Race | | | | | | |
| Caucasian | 44 | 29 | 9 | 23 | 17 | 3 |
| Asian | 4 | 2 | 1 | 2 | | |
| African-American | 1 | 1 | 1 | | 1 | |
| Mixed | 13 | 4 | 1 | 6 | 3 | |
| Indian | 1 | | | | | |
| Unknown | | | | | 1 | |
| Subjects Clinical Information | ASD | TD | Contrast | ASD | TD | Contrast |
| Mullen Scales of Early Learning (T-Scores) - Mean (SD) | | | | | | |
| Visual Reception | 39.7 (11.0) | 59.0 (10.3) | 48.1 (9.0) | 40.6 (13.6) | 51.6 (10.2) | 44.3 (4.5) |
| Fine Motor | 37.3 (12.2) | 55.9 (9.1) | 55.8 (8.4) | 40.1 (16.0) | 57.5 (8.5) | 55.7 (2.9) |
| Receptive Language | 29.1 (12.0) | 52.4 (8.3) | 46.9 (8.5) | 31.6 (16.1) | 50.7 (10.2) | 36.7 (4.9) |
| Expressive Language | 29.1 (11.4) | 53.7 (9.5) | 46.3 (7.9) | 31.4 (16.4) | 52.0 (8.6) | 41.0 (2.6) |
| ADOS T Social Affect Total, Modules 1 and 2 Communication + Social Interaction Total - Mean (SD) | | | | | | |
| ADOS CoSo/SA Score * | 15.0 (3.9) | 2.1 (1.7) | 0.6 (1.1) | 12.8 (4.8) | 2.4 (2.2) | 5.0 (5.0) |
| ADOS RRB Score | 4.1 (1.9) | 0.3 (0.5) | 4.1 (4.7) | 2.5 (1.6) | 0.3 (0.4) | 0.7 (1.2) |
| ADOS Total Score | 19.1 (4.7) | 2.4 (1.9) | 2.1 (2.5) | 15.3 (5.4) | 2.6 (2.3) | 5.7 (6.0) |
| Early Learning Composite | 71.0 (16.2) | 110.5 (12.4) | 98.7 (11.4) | 76.1 (21.6) | 106.0 (12.9) | 89.3 (6.7) |
| Vineland scores (VABS) † | 82.2 (9.4) | 101.6 (9.3) | 92.4 (7.6) | 83.6 (14.1) | 100.8 (7.3) | 95.0 (1.0) |

‡ >1 standard deviation below expected values on the language subtests on the Mullen ⁝ >1 standard deviation below expected values on 3 or more of the subtests of the Mullen and the overall developmental quotient was >1 standard deviation below expected values (i.e., <85)

“ <than 37 weeks gestation

‹‹ Diagnosis of social emotional delay

Z,53 Mother with drugs exposure during pregnancy

* Replication: 32% of ASD population had ADOS T, 48% had ADOS 1, and 20% had ADOS 2

Discovery: 64% of ASD population had ADOST, 31% had ADOS 1, and 5% had ADOS 2

† Adaptive Behavioral Scales Adaptive Behavior Composite Score

Blood Sample Collection and Processing

Leukocytes were captured using LEUKOLOCK filters (Ambion, Austin, Tex.) from four-to-six ml of blood (see Methods in Example 2) for Discovery and Replication samples. RNA samples in the Discovery set were tested on the Illumina Human-HT12_v.4 platform, while the Illumina WG-6 platform was used for the Replication set. Five low-quality arrays were identified and excluded from statistical analyses (see Methods in EXAMPLE 2). Final samples were 87 ASD and 55 control Discovery toddlers and 44 ASD and 29 control Replication toddlers (Table 4).

MRI Scanning and Neuroanatomical Measurement

MRI data were obtained during natural sleep from Discovery toddlers (65 ASDs, 38 controls) whose parents consented to scanning. Twelve neuroanatomic measurements were obtained using a semi-automated pipeline integrating modified features of FSL and BrainVisa (fmrib.ox-.ac.uk/fsl/; brainvisa.info), and included total brain volume, left and right cerebral gray and white matter volumes, left and right cerebral cortical surface areas, left and right cerebellar gray and white matter volumes, and brainstem volume (See Methods in EXAMPLE 2).

Statistical and Bioinformatic Analyses

Statistical analyses were performed on normalized and filtered expression data. Effects of age on neuroanatomic measures were removed via Generalized Additive Models (GAM-R package v1.06.2)[20].

Figure 1B:
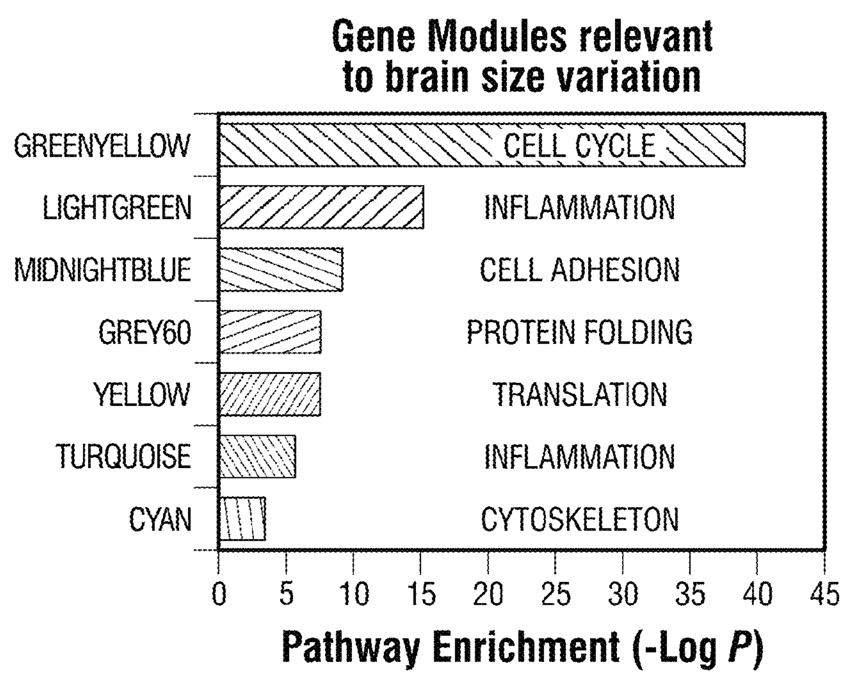

Co-expression analysis (WGCNA) was used to identify gene modules across all Discovery subjects and within each study group separately (See Methods in EXAMPLE 2). WGCNA analysis, Pearson and Spearman correlations were used to identify associations between gene expression patterns and neuroanatomy across all Discovery toddlers. Gene Significance (gene expression level to phenotype correlation) and Module Membership (gene connectivity within each module) were also computed using WGCNA (See Methods in Example 2). Class comparison analyses were performed using a random variance model with 10,000 univariate permutation tests in BRB-Array Tools (linus.nci.nih.gov/BRB-ArrayTools.html). MetaCore software was used for pathway enrichment analyses. Hyper-geometric probability (Hyp. P) was used to test the significance of Venn analyses versus random gene sets of equal size (See Methods in EXAMPLE 2). Differentially expressed (DE) genes from Discovery toddlers were used to identify a potential gene expression signature of ASD, Four DE modules were selected based on AUC performance in classification of Discovery toddlers using a logistic regression function (glmnet). CNVision was used to call copy number variations (CNVs) in misclassified ASD subjects as previously described.[2,21]

modules displayed the strongest correlations with brain and cerebrum volumes across groups (Table 5) and all seven modules were associated with TBV measures. The greenyellow module displayed top enrichment in cell cycle functions, while protein folding genes were highest in the grey60 module (FIG. 1B, Table 8). Seven different gene modules were instead associated with diagnosis (see Table 26 in EXAMPLE 2) and Metacore analysis displayed no significant enrichment for the strongest correlated modules followed by cell cycle, translation and inflammation genes (see Table 26 in EXAMPLE 2).

TABLE 5

WGCNA association analysis (Pearson correlation) of module-eigengenes and age-corrected neuroanatomic measures in ASD and control toddlers together

| ASD/Control MODULE | CB_GM (L/R) | CB_WM (L/R) | CBLL_GM (L/R) | CBLL_WM (L/R) | BS | TBV | Hemi_SA |
|---|---|---|---|---|---|---|---|
| GreenYellow | −0.32***/−0.33*** | −0.3***/−0.28*** | ns/ns | ns/ns | ns | −0.31*** | −0.29***/−0.3*** |
| Grey60 | −0.31***/−0.32*** | −0.26**/−0.24** | ns/ns | ns/ns | ns | −0.3*** | −0.26**/−0.27** |
| Cyan | 0.21*/0.2* | 0.18*/0.17* | ns/ns | ns/ns | ns | 0.18* | 0.14*/0.15* |
| Turquoise | 0.18*/0.19* | 0.17*/0.17* | ns/ns | ns/ns | ns | 0.19* | 0.16*/0.16* |
| Yellow | −0.2*/−0.21* | −0.17*/−0.17* | ns/ns | ns/ns | ns | −0.19* | −0.18*/−0.18* |
| LightGreen | −0.19*/−0.21* | −0.18*/−0.17* | ns/ns | ns/ns | ns | −0.21* | −0.15*/−0.17* |
| MidnightBlue | 0.21*/0.22** | ns/ns | ns/ns | ns/ns | ns | 0.21* | 0.21*/0.21* |

Signif. codes relate also to FIG. 1B: p-value
***<0.001;
**< 0.01;
*<0.05 Signif
L = Left,
R = Right,
CB = Cerebrum,
CBLL = Cerebellum,
GM = Gray Matter,
WM = White Matter,
TBV = Total Brain Volume,
hemi = hemisphere,
SA = Surface Area,
BS = Brain Stem,
ns = not significant Results The majority of Discovery and Replication subjects were of Caucasian origin. Pearson's Chi-squared test showed no significant difference in race/ethnicity distribution between ASD and control (Discovery $X^2$=7.98, P=0.1569; Replication $X^2$=7.19, P=0.2065).

Across ASD and control toddlers, age-corrected MRI total brain volume (TBV) measures followed a normal distribution with no statistically significant difference (FIG. 1A, P=0.645), as well as for the other measures.

After filtering across all Discovery subjects, 12208 gene probes were used for downstream analyses.

Figure 1C:
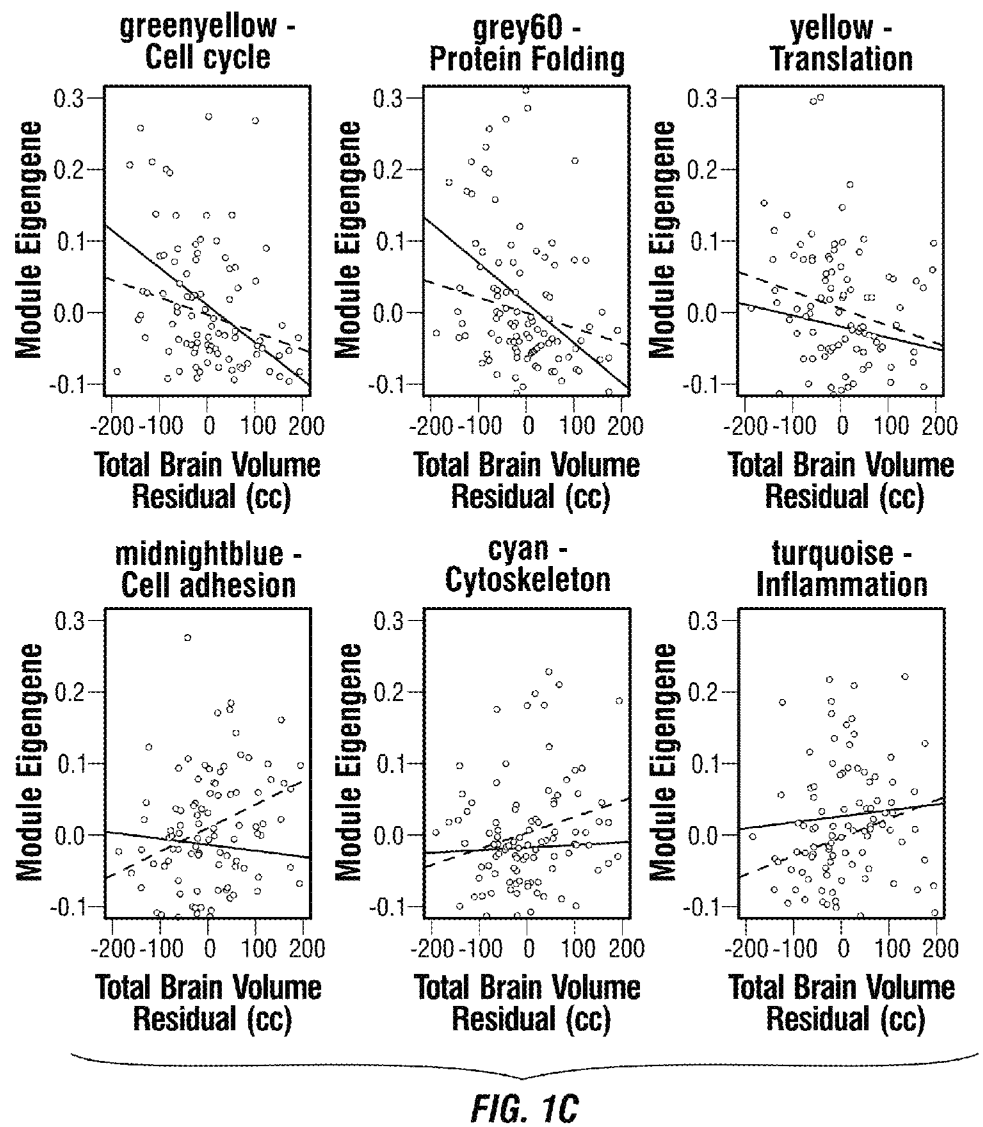
Figure 5:
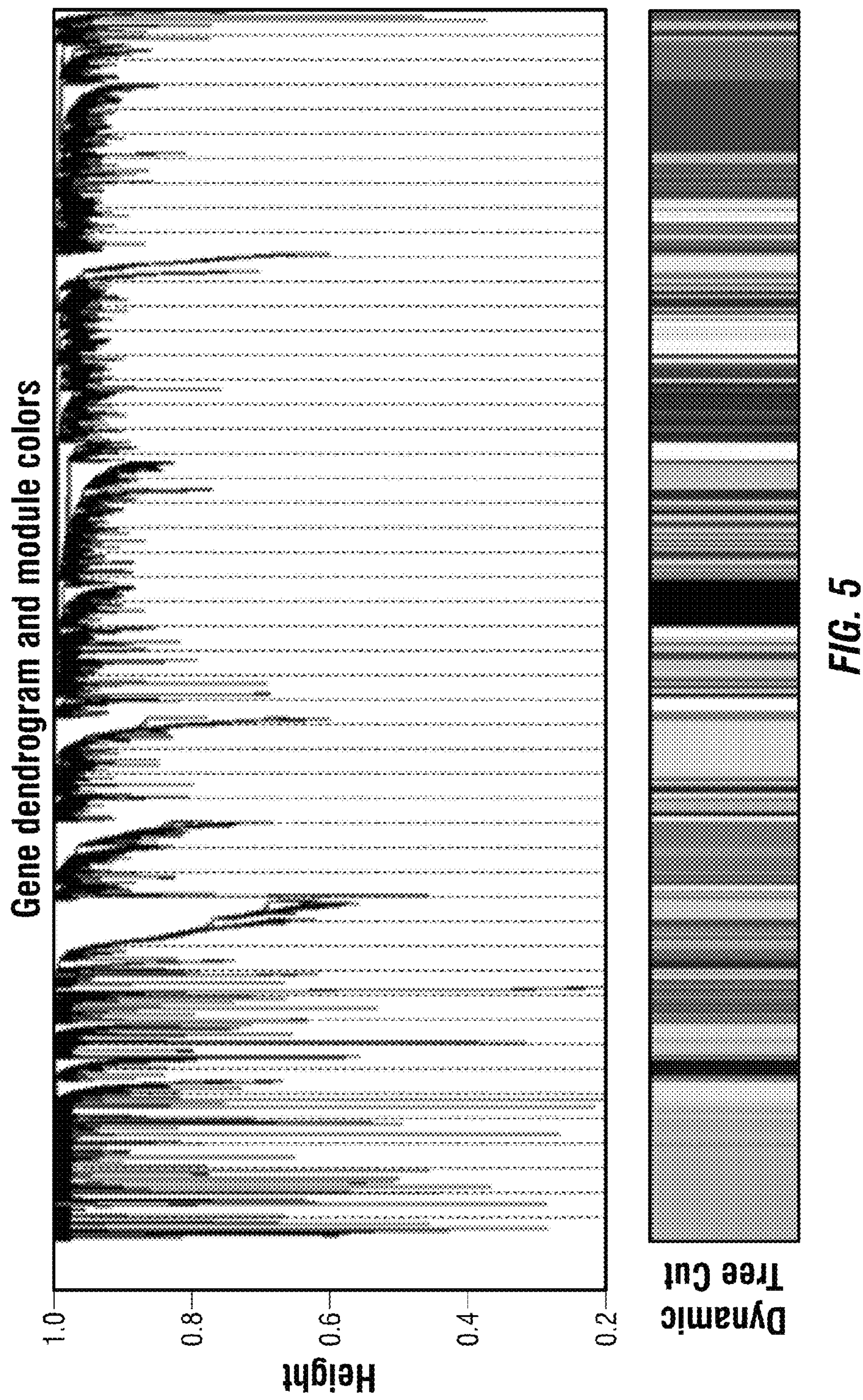
FIG. 5 WGCNA analysis across ASD and control toddlers. Co-expression modules are generated and color-coded (here showed in grey scale). Each vertical line corresponds to a gene, and genes with similar expression are clustered into modules. Modules are herein called by the assigned WGCNA default colors. Module eigengenes are computed for each subject and each module.
Figure 6A:
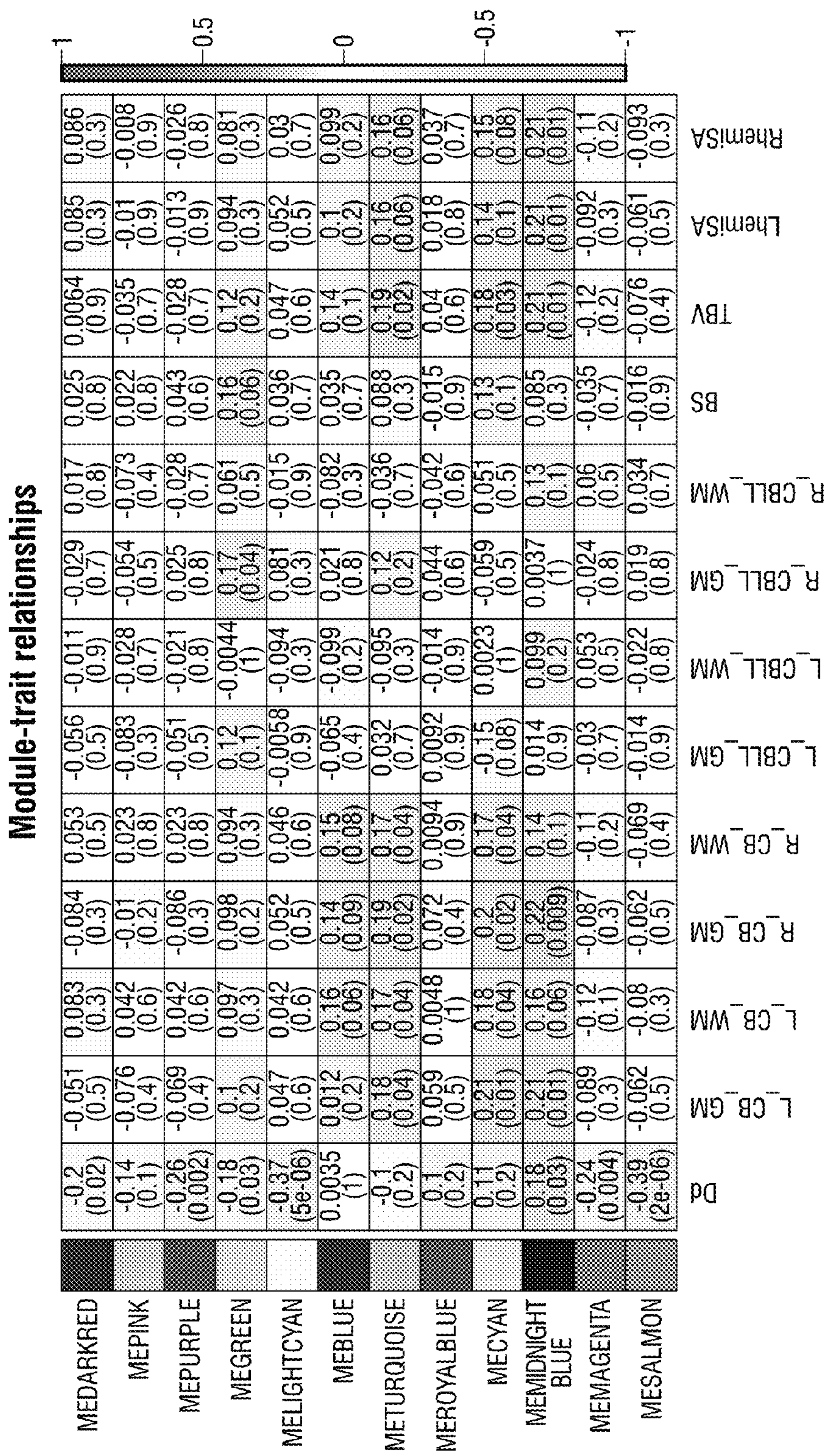
FIGS. 6A-6B Correlation analysis between modules and neuroanatomic measures using WGCNA on all discovery subjects. pValues are in parentheses. Dx=diagnosis, L=Left, R=Right, CB=Cerebrum, CBLL=Cerebellum, GM=Gray Matter, WM=White Matter, TBV=Total Brain Volume, hemi=hemisphere, SA=Surface Area, BS=Brain Stem.
Figure 6B:
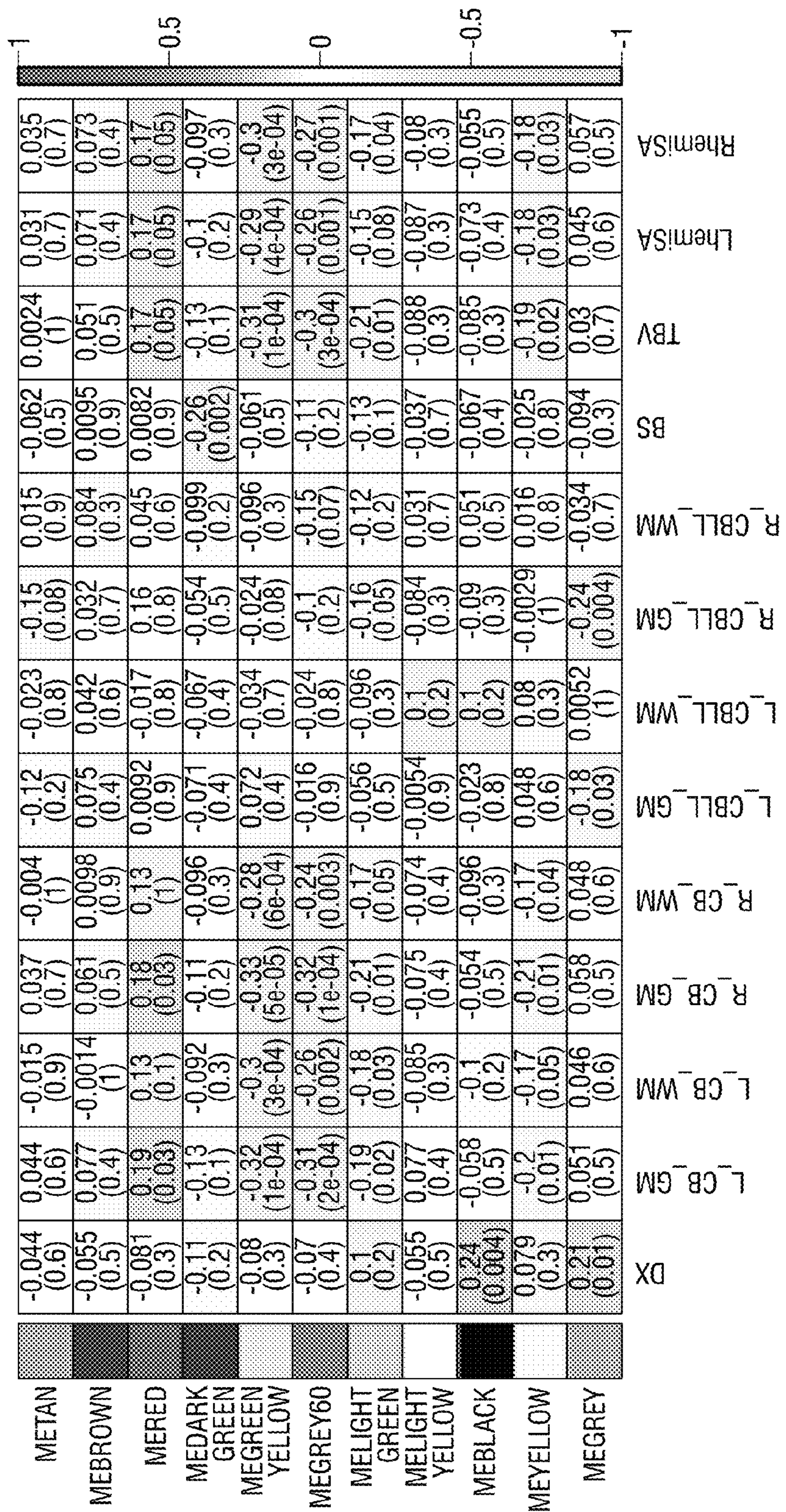

Different Gene-Networks Underlie Variation of Neuroanatomic Measures in ASD and Control Groups WGCNA Across Combined ASD and Control Groups Unsupervised co-expression analysis using WGCNA identified 22 modules of co-expressed genes (see FIG. 5) with eigengene values computed for each module and each ASD and control subject. Of these 22 modules, seven were consistently correlated with neuroanatomic measures across all subjects, including TBV, cerebral gray, cerebral white and cerebral cortical surface area (Table 5, FIG. 6) and displayed statistically significant enrichments (P<0.05, FDR<0.05; FIG. 1B). The greenyellow and grey60 gene In control toddlers, only the cell cycle and protein folding module eigengenes (MEs) were strongly correlated with TBV and all cerebral measures (Tables 6 and 8). In contrast, ASD toddlers displayed correlations with several MEs, with the strongest being cell adhesion, inflammation and cytoskeleton regulation and the weakest being cell cycle, protein folding and transcription (Tables 6 and 8). Unlike control toddlers, cell cycle and protein folding MEs in ASD toddlers were not significantly correlated with cerebral white matter measures; instead, cerebral white matter volume was strongly correlated with cell adhesion and, to a lesser extent, inflammation and cytoskeleton regulation MEs (Table 6). Linear modeling of MEs with TBV variation (from small to big) displayed that cell cycle and protein folding genes have highest expression in normal small brains, while reduced to neutral effects are carried out by translation, cell adhesion, cytoskeleton and inflammation genes (FIG. 1C). Conversely, the combinatorial action of reduced activity of cell cycle and protein folding genes with a gain in expression of cell adhesion, cytoskeleton and inflammation seems to drive pathological brain enlargement in ASD (FIG. 1C).

TABLE 6

Pearson and Spearman correlations of module-eigengenes and age-corrected neuroanatomic measures in ASD and control toddlers separately

| Control MODULE | CB_GM (L/R) | CB_WM (L/R) | TBV | Hemi_SA (L/R) | Top Network |
|---|---|---|---|---|---|
| Grey60 | −0.41**/−0.42** −0.47^^/−0.46^^ | −0.49**/−0.48** −0.49^^/−0.49^^ | −0.47** −0.53^^^ | −0.4*/−0.42** −0.4^/−0.41^ | Protein folding_ER and cytoplasm |
| GreenYellow | −0.43**/−0.44** −0.44^^/−0.45^^ | −0.42**/−0.41* −0.37^/−0.36^ | −0.44** −0.42^^ | −0.39*/−0.43** −0.31^/−0.35^ | Cell cycle_core |
| **ASD MODULE** | **CB_GM (L/R)** | **CB_WM (L/R)** | **TBV** | **Hemi_SA (L/R)** | **Top Network** |
| MidnightBlue | 0.35**/0.37** 0.42^^^/0.41^^^ | 0.29*/0.26* 0.31^/0.3^ | 0.35** 0.4^^ | 0.33**/0.34** 0.42^^^/0.41^^^ | Cell adhesion_integrin-mediated |
| Turquoise | 0.29*/0.29* 0.39^^/0.38^^ | ns/ns 0.29^/0.29^ | 0.29* 0.39^^ | 0.26*/0.25* 0.35^^/0.31^ | Inflammation_interferon signaling |
| Cyan | 0.31*/0.31* 0.26^/0.27^ | ns/ns 0.25^/ns | 0.27* 0.28^ | 0.24*/0.25* ns/ns | Cytoskeleton_regulation and rearrangement |
| Yellow | −0.25*/−0.25* −0.3^/−0.3^ | ns/ns ns/ns | ns −0.27^ | ns/ns −0.27^/−0.25^ | Translation_reulation of initiation |
| GreenYellow | −025*/−026* −0.26^/−0.3^ | ns/ns ns/ns | ns −0.27^ | ns/ns −0.28^/−0.27^ | Cell cycle_core |
| Grey60 | −0.25*/−025* −0.29^/−0.29^ | ns/ns ns/ns | ns −0.28^ | ns/ns −0.28^/−0.3^ | Protein folding_ER and cytoplasm |

Figure 2A:
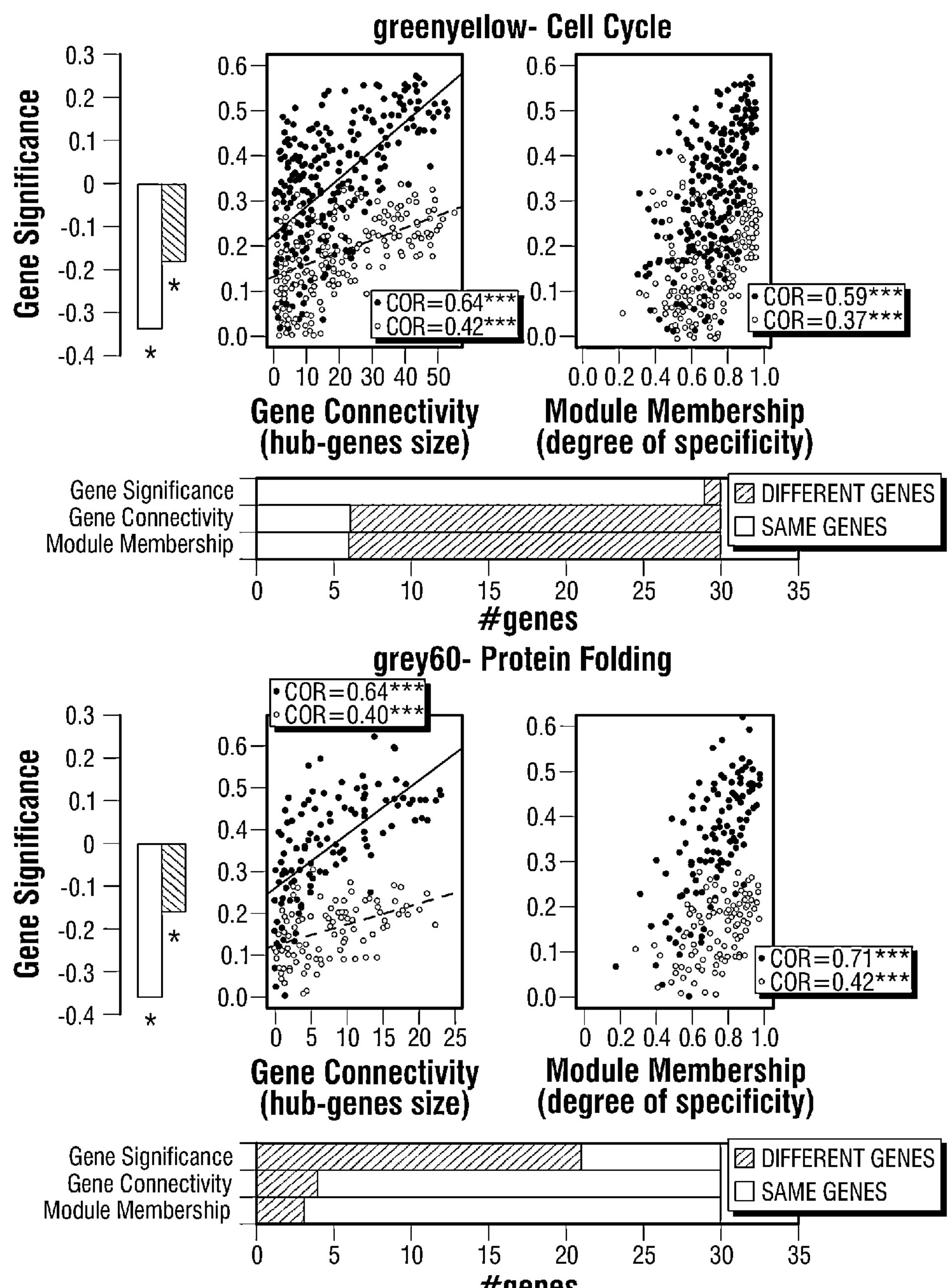
FIGS. 2A-2C. WGCNA analysis of the combined dataset (ASD and control together) defined which modules are associated with Total Brain Volume (TBV) measures in control toddlers and which modules in ASD toddlers. The impact of gene expression on brain size variation is calculated as Gene Significance (GS) for each TBV-associated module within control (dark grey) and ASD toddlers (light grey). The bar graphs show the difference in GS between the two groups. Negative GS values reflect the opposite relationship between eigengenes and TBV variation (see Table 6), thus high gene expression levels associated with small brain and vice versa. Solid bars with an asterisk indicate that the association is statistically significant. Empty bars without the asterisk on top indicate that the association is not significant. The correlation between the GS and Gene Connectivity (GC; defining hub-genes) for each gene within a module displays the change in activity patterns and impact on brain size variation of hub genes (left scatterplot for each module). The correlation between GS and Module Membership (MM; specificity of a gene to the assigned module) display consistent activity pattern changes relative to hub-genes alterations (right scatterplot for each module). The analysis of the top 30 genes for the three network features (GS, GC, MM) displayed that GS was the feature with the highest number of altered genes in each module. The module enriched in translation was overall the one with the highest number of genes that changed between ASD and control toddlers.
Figure 2B:
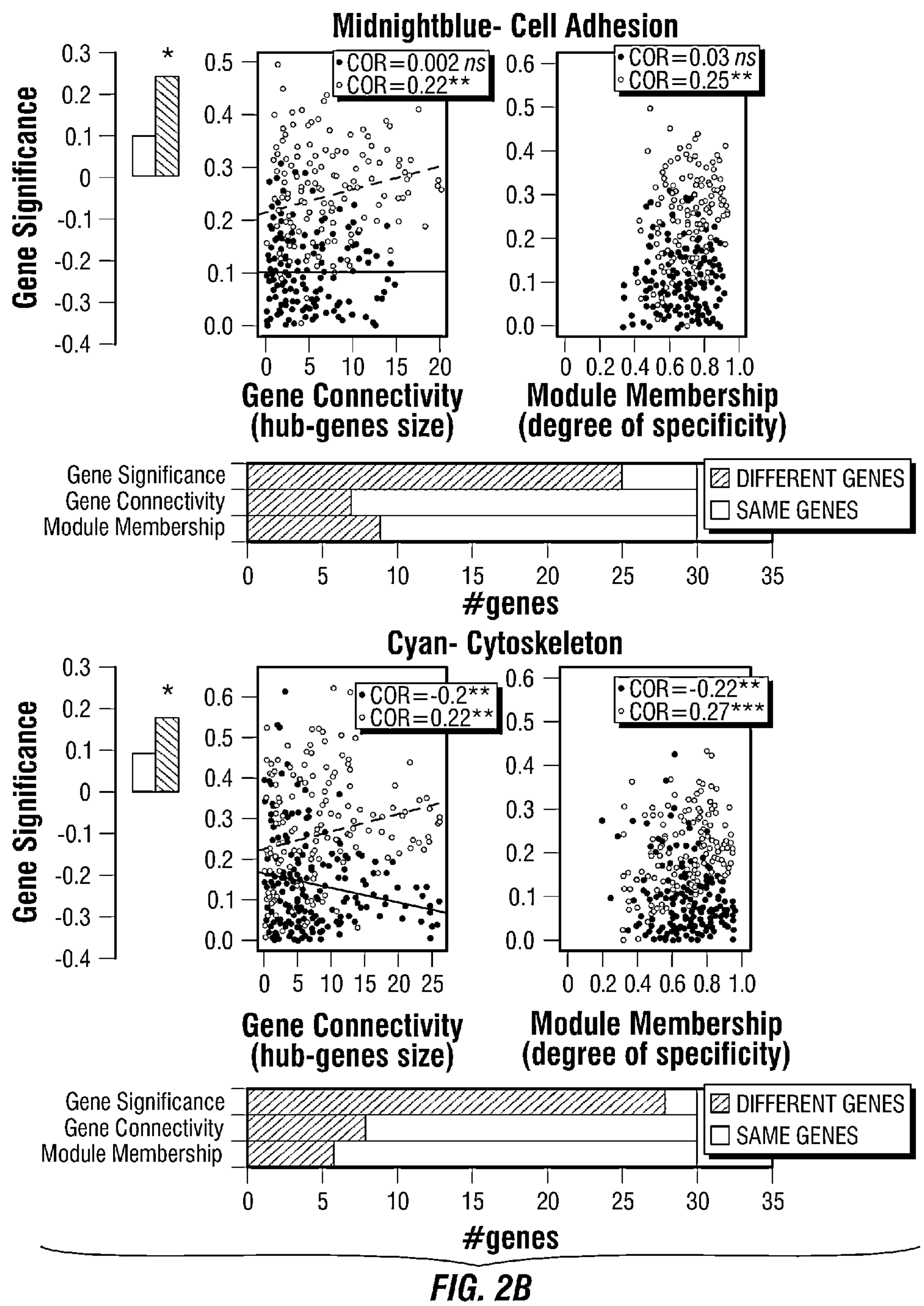
Figure 2C:
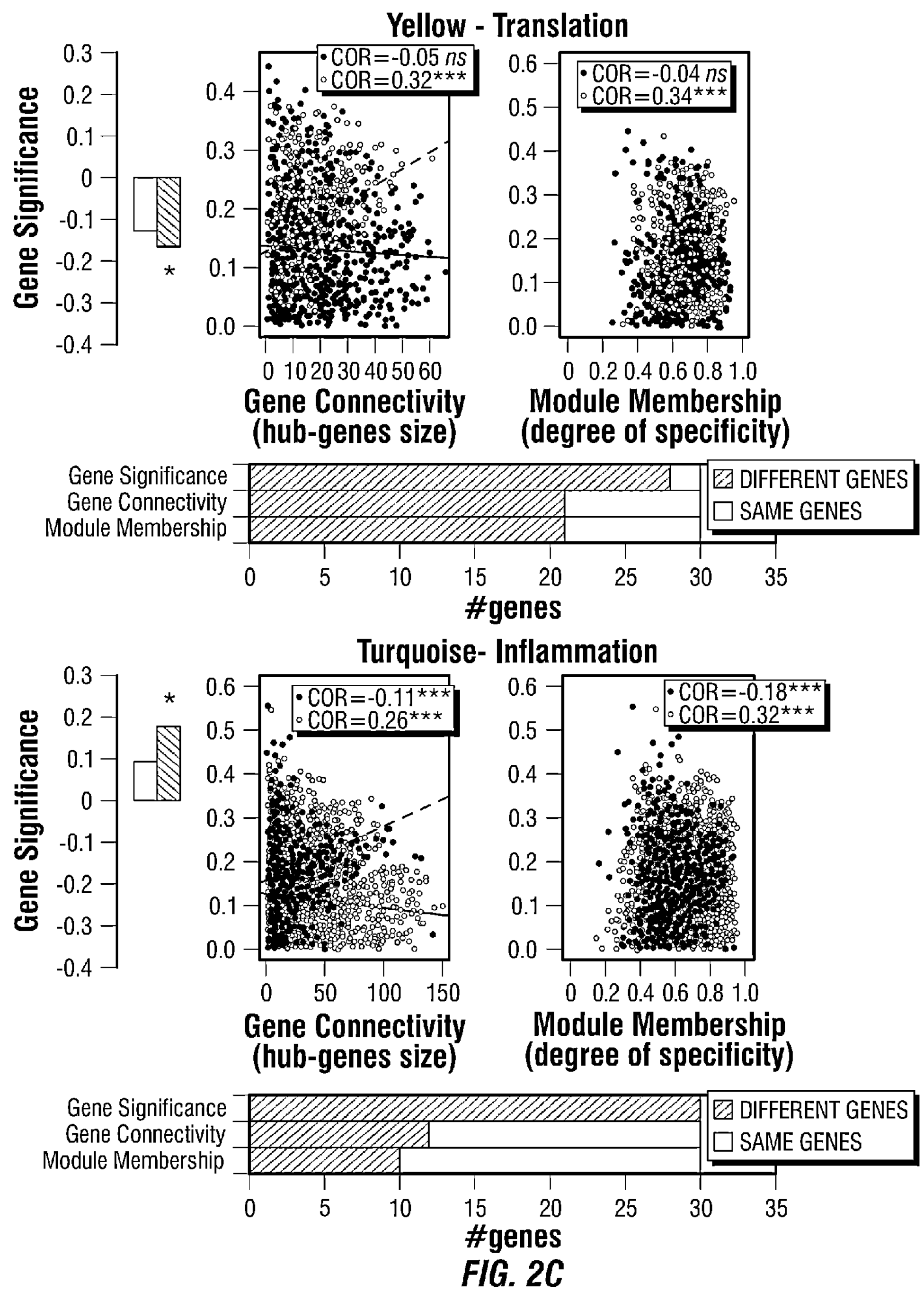
Figure 7:
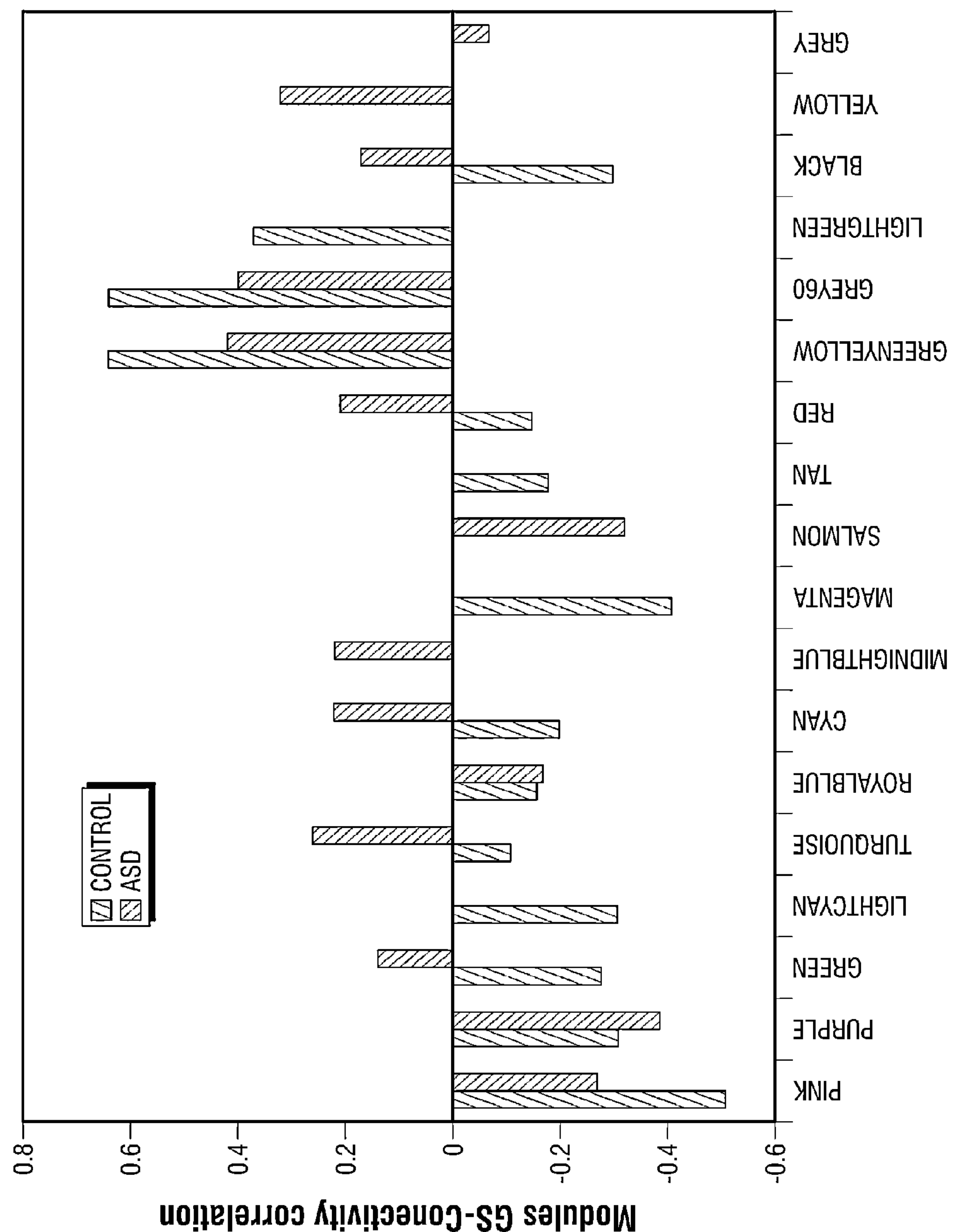
FIG. 7 Gene Significance (GS) to Gene Connectivity (GC) correlation within each module in the ASD and control groups. 12 of the 22 co-expressed modules across groups displayed a severe change in pattern direction (negative to positive or not significant correlation), while 4 modules had a modest change in correlation (same direction).

Signif. codes: p-value Pearson
***<0.001;
**<0.01;
*<0.05; p-value Spearman
^^^<0.001;
^^<0.01;
^<0.05
Correlations relate to FIG. 1C, D;
L = Left,
R = Right,
CB = Cerebrum,
GM = Gray Matter,
WM = White Matter,
TBV = Total Brain Volume,
hemi = hemisphere,
SA = Surface Area
ns = not significant Network Patterns Alteration in ASD Vs. Control Groups Calculation of the Gene Significance (GS) value for each module provides a measure of the impact of co-expressed genes on normal and pathologic brain size variation. Correlation analysis between GS and intra-modular Gene Connectivity (GC) revealed a major rearrangement of activity patterns across several gene networks (See Tables 21-23 for the genes with highest GS and GC). Twelve (12) of the 22 modules displayed a shift in pattern direction (negative to positive or not significant, and vice-versa) suggesting that for each of these 12 modules the impact of hub-genes on brain size variation was significantly altered in ASD compared to control (FIG. 7). Importantly, Cell cycle and Protein folding hub-genes displayed reduced GS values in ASD toddlers, while a substantial gain in GS was observed for hub-genes in the cytoskeleton, inflammation, cell adhesion and translation modules (FIG. 2). Similar analyses, assessing the specificity of a gene to a module (Module Membership, MM) in respect to its GS, supported the alterations in gene connectivity (FIGS. 2A-2C; See Tables 24 & 25 for the genes with highest MM).

WGCNA in ASD and Control Groups Separately

Figure 3:
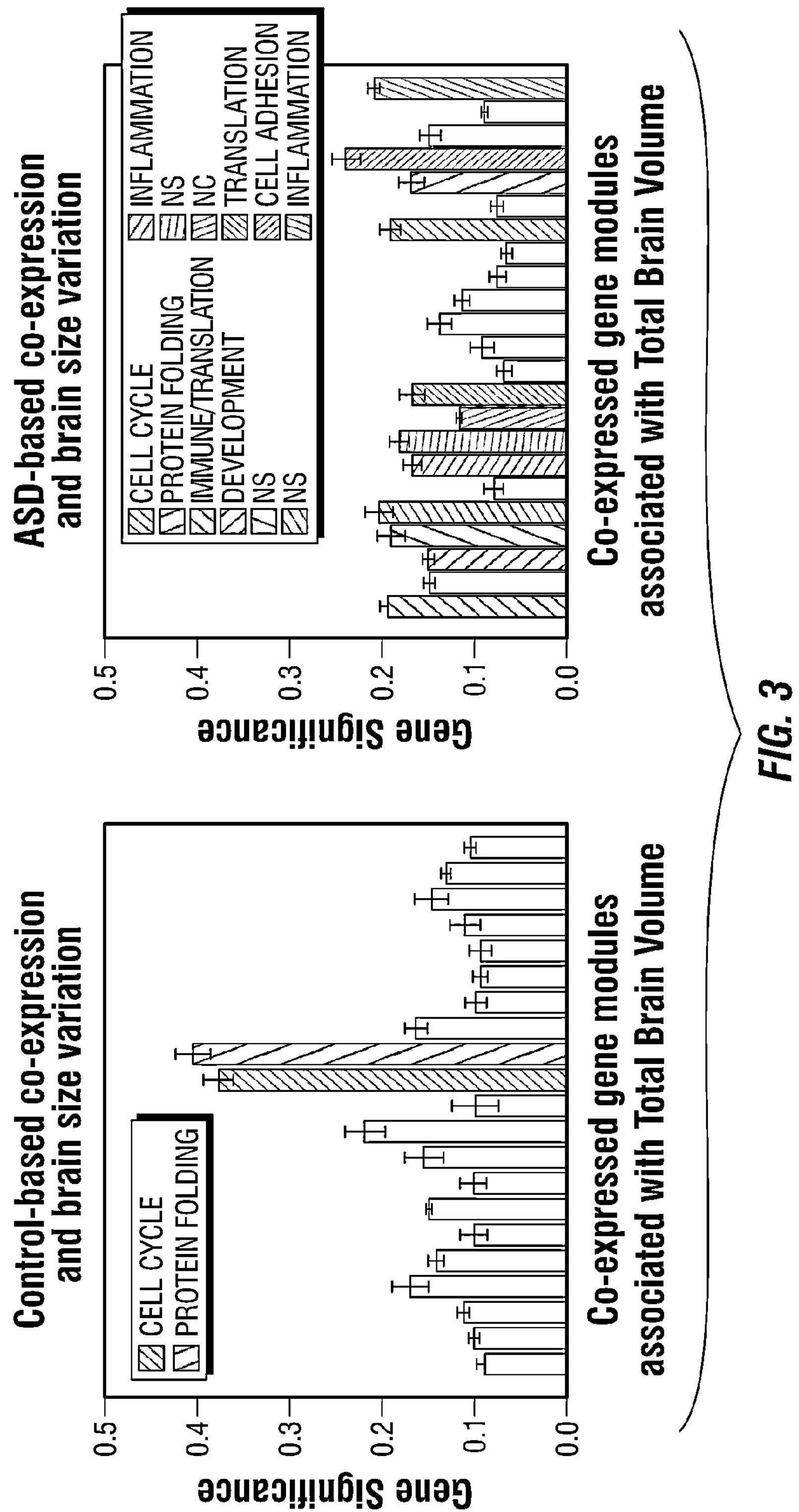
FIG. 3. Co-expression modules generated from the WGCNA analysis of control and ASD samples separately. The absolute values of GS for control-based modules (left) are consistent with the modules from the combined analysis within the control group (FIGS. 2A-2C). The absolute values of GS for ASD-based modules (right) are consistent with the combined analysis within the ASD group (FIGS. 2A-2C) and displayed an increase in the number of modules associated with TBV measures. The differences in modules associated with TBV measure in the separate WGCNA analysis are hence accentuated.
Figure 8A:
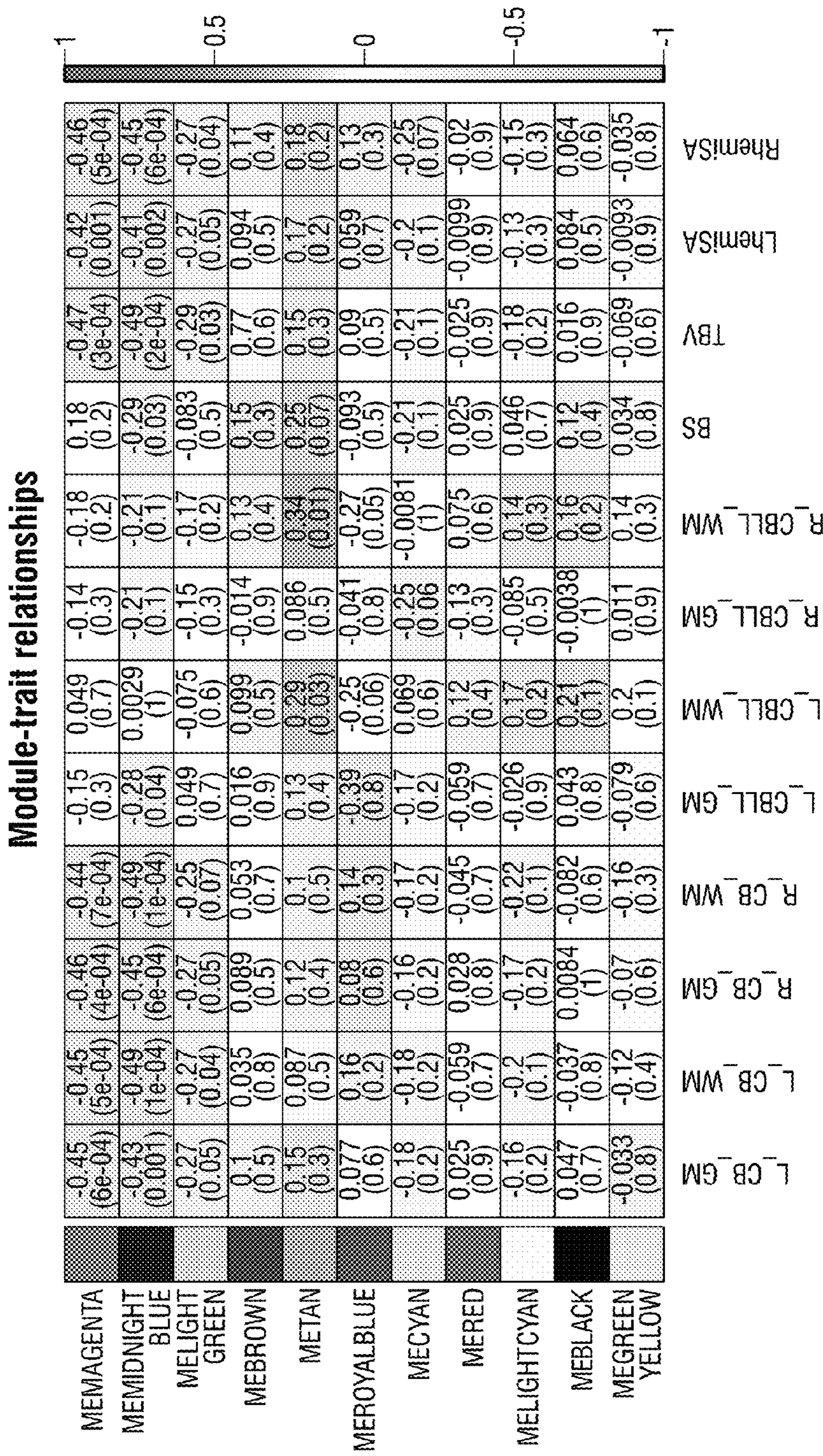
FIGS. 8A-8B Association analysis between modules and neuroanatomic measures using WGCNA on control toddlers. L=Left, R=Right, CB=Cerebrum, CBLL=Cerebellum, GM=Gray Matter, WM=White Matter, TBV=Total Brain Volume, hemi=hemisphere, SA=Surface Area, BS=Brain Stem.
Figure 8B:
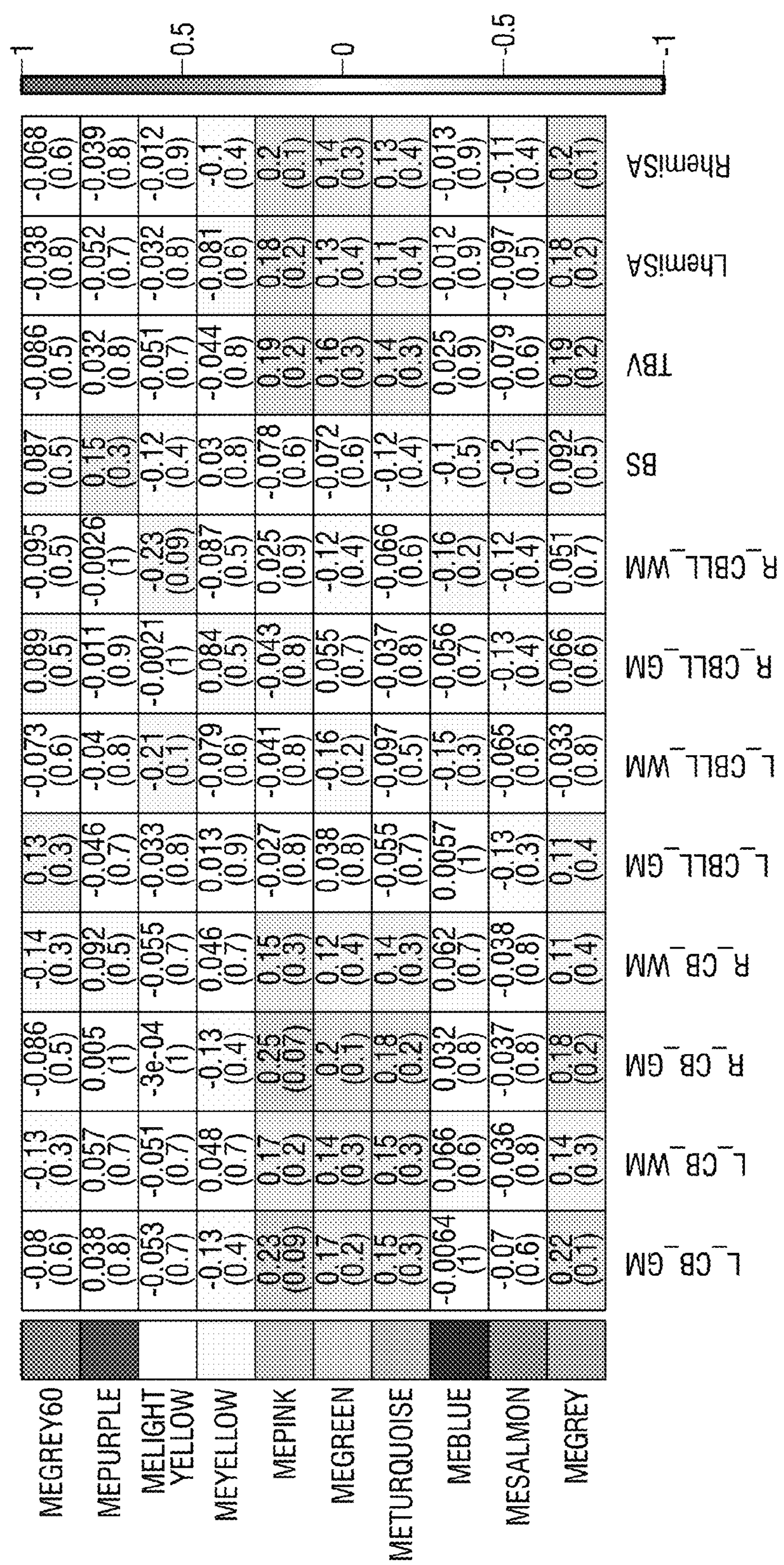
Figure 9A:
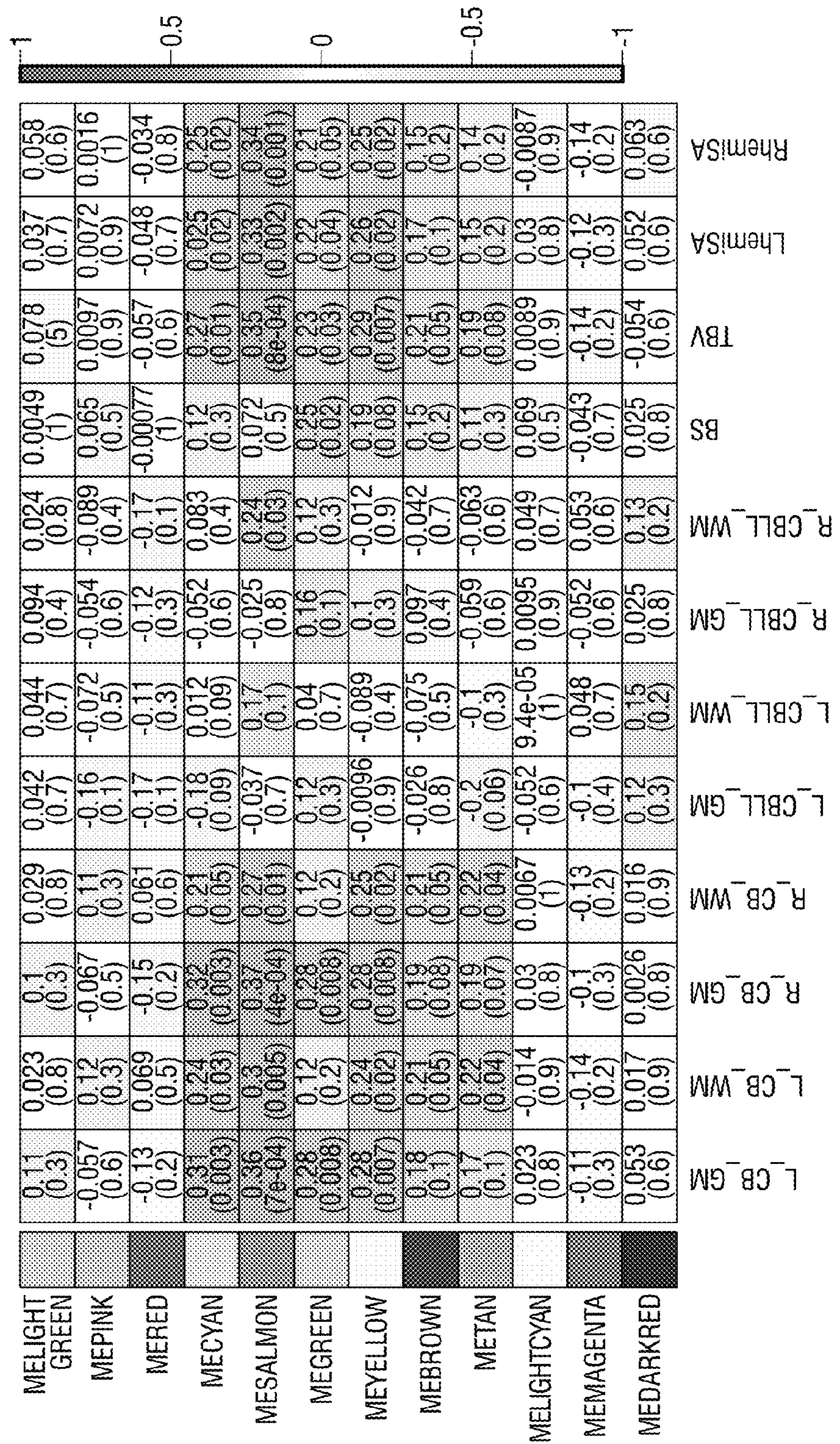
FIGS. 9A-9B Association analysis between modules and neuroanatomic measure using WGCNA on ASD toddlers. L=Left, R=Right, CB=Cerebrum, CBLL=Cerebellum, GM=Gay Matter, WM=White Matter, TBV=Total Brain Volume, hemi=hemisphere, SA=Surface Area, BS=Brain Stem.
Figure 9B:
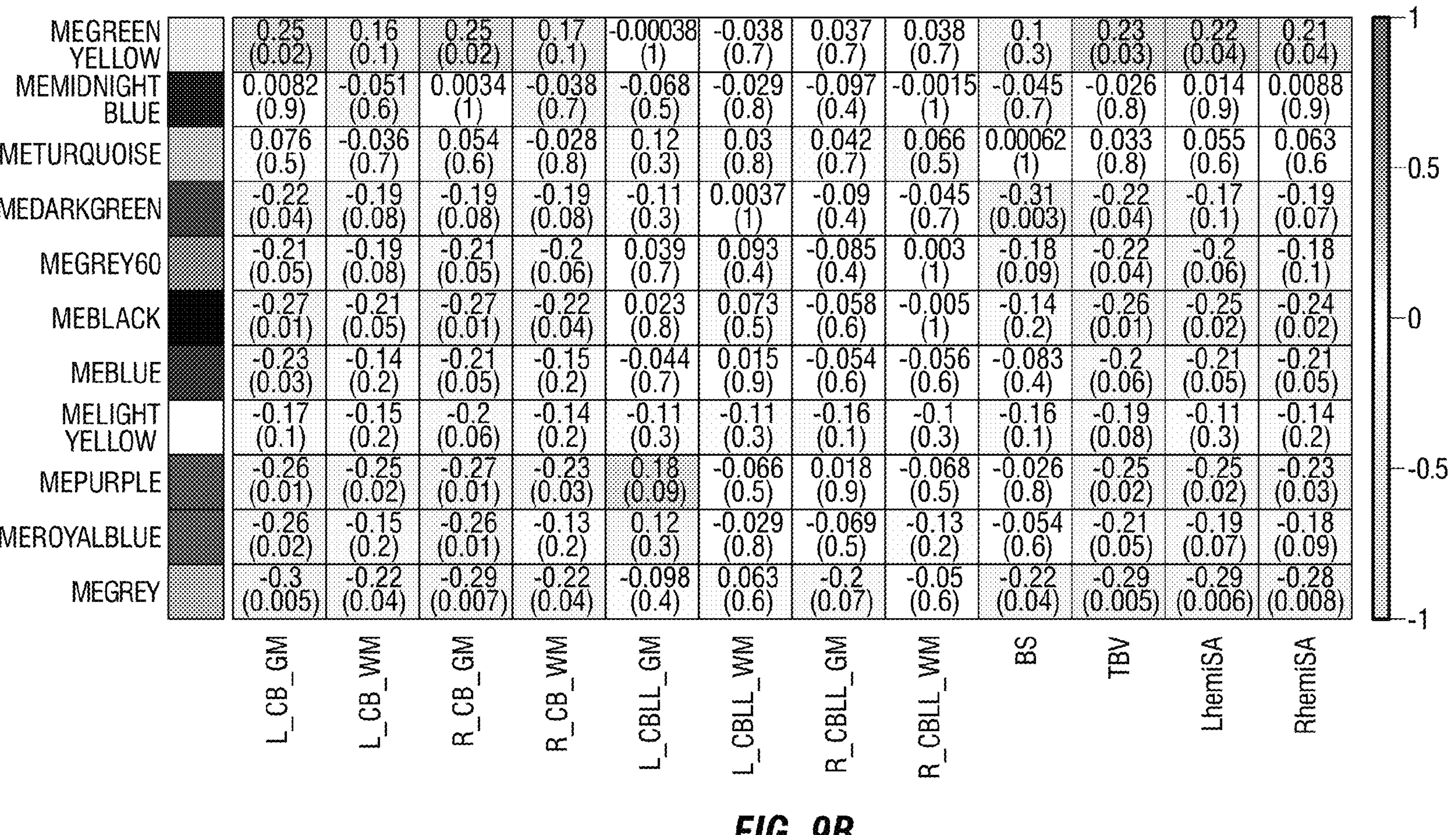

To further test for ASD-specific gene expression relationships to brain development, the same 12208 gene probes were analyzed by WGCNA within each study group (ASD, control) separately. Of 20 control-based co-expression modules, only 2 were significantly and strongly correlated to brain volume and cerebral measures (FIG. 8). As to the above across-groups analysis, these two modules were enriched in cell cycle and protein folding genes and displayed high GS values for normal TBV variation (FIG. 3; Table 9). Of 22 ASD-based co-expression modules, 11 were significantly correlated with one or more neuroanatomic measures (FIG. 9). Unlike control toddlers, these 11 modules had GS values consistent to the across-groups analysis and were enriched in multiple functional domains including immune, inflammation, cell adhesion, translation, and development (FIG. 3, Table 10).

Figure 4A:
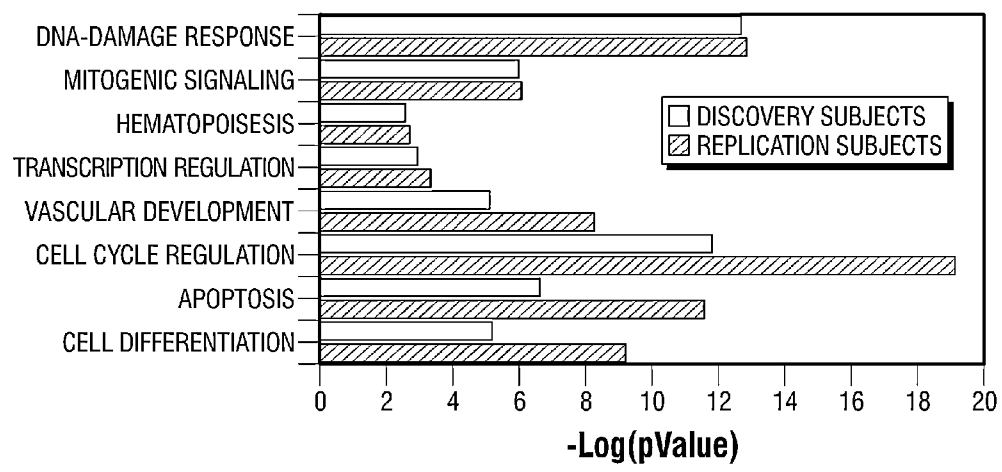
FIGS. 4A-4E. Pathway-based Replication analysis of differentially expressed (DE) genes. Module-based classifier efficiently distinguishes ASD from control subjects and displays a high protein-protein interactions (PPI) enriched in translation genes.
Figure 4B:
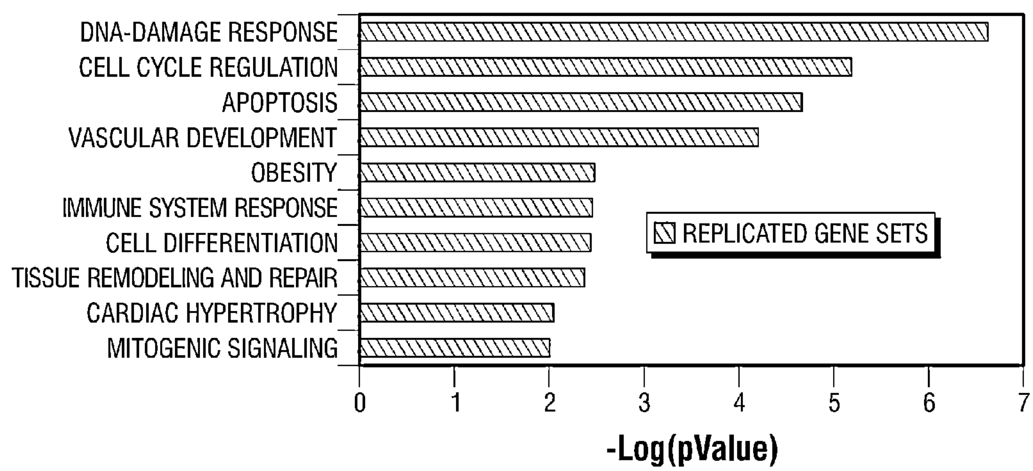

DNA-Damage and Mitogenic Gene-Networks are Consistently Dysregulated in ASD Vs Control Class comparison analyses between ASD and control toddlers found 2765 unique differentially expressed (DE) genes (see Table 16). Metacore enrichment displayed significant dysregulation for immune/inflammation response, DNA-damage/apoptosis and cell cycle regulation pathways as well as apoptosis, as the top Metacore process networks (Table 11). Pathway comparison between the Discovery and the Replication datasets indicated that DNA-damage response and mitogenic signaling were the most similarly and statistically significant dysregulated pathways in both samples (FIG. 4A, Table 12). At the gene level, 405 genes were commonly dysregulated and accounted primarily for networks involved in cell number regulation (FIG. 4B, Tables 13 and 17).

Venn analysis between the group-based gene modules associated with neuroanatomic measures and the 2765 DE genes, showed that 12.7% (37/290; Hyp. P=0.38) and 27.1% (786/2894; Hyp. P=1.8e-127) of the gene-modules were differentially expressed in control and ASD specific modules, respectively.

Key genes in the DNA-damage and mitogenic signaling categories were CDKs, CREB1, ATM, 14-3-3s, AKT, BCL2, PCNA, STAT1, PI3K, Beta-catenin, Caspases, NUMA1, NFBD1, PP2A, RADs and MAPKs (Tables 18 & 19).

Module-Based Classification Efficiently Distinguishes ASD from Control Toddlers

Figures 4C, 4D:
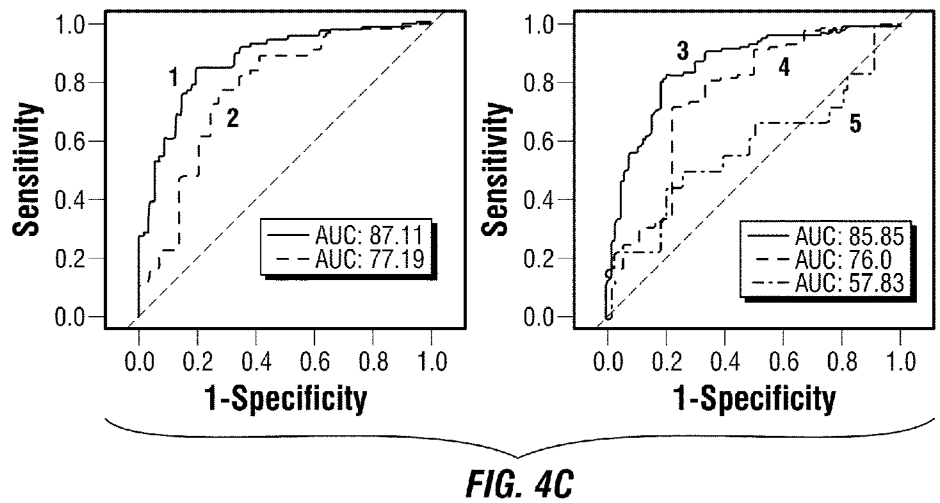
Figure 10:
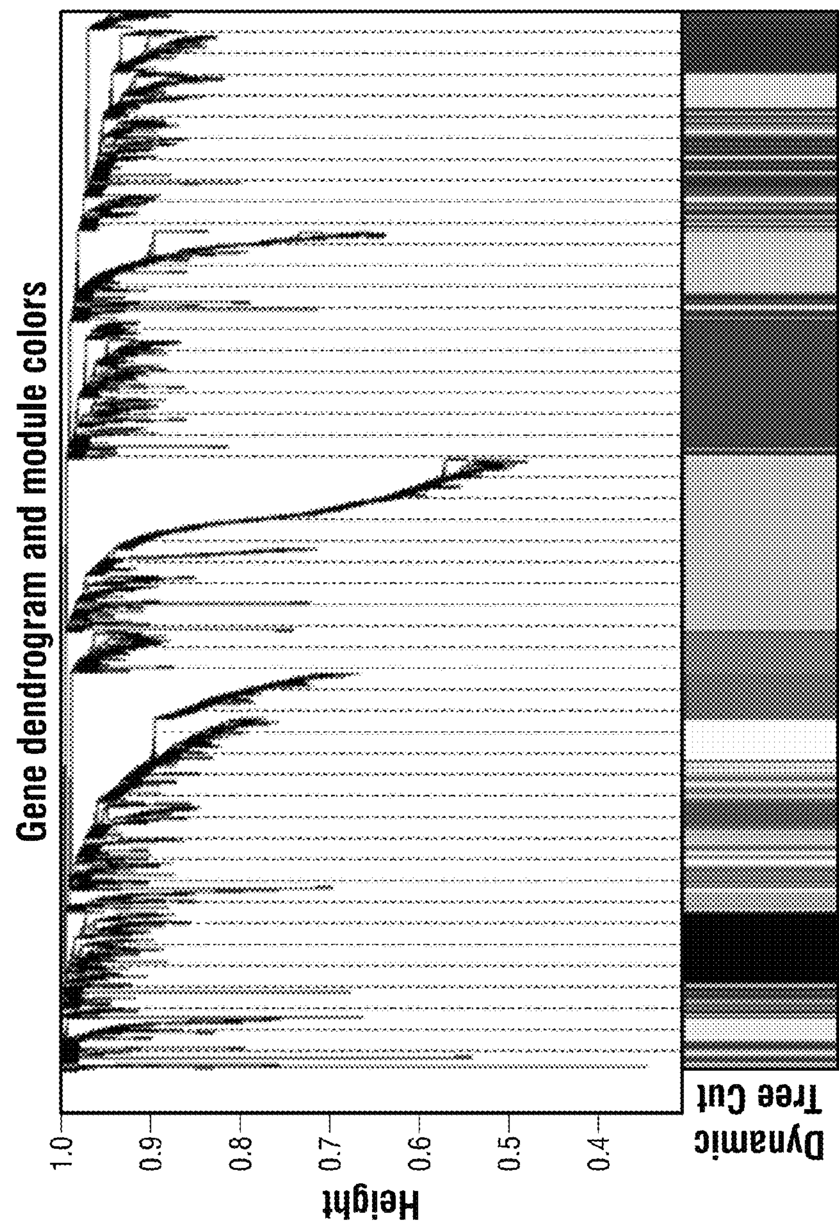
FIG. 10 WGCNA analysis across ASD and control toddlers using the differentially expressed genes. Co-expression modules are generated and color-coded (here showed in grey scale). Each vertical line corresponds to a gene, and genes with similar patterns are clustered into modules. Modules are herein called by the assigned WGCNA default colors. Module eigengenes are computed for each subject and each module.

Co-expression analysis of the 2765 DE genes using WGCNA found 12 gene modules and eigengenes were calculated for each subject and each module (FIG. 10). Four of these module eigengenes were used in the classification analysis together with subject's age as predictor. Logistic regression of diagnosis with age as predictor produced 1.07 odds ratio (P<0.05) and classification without age was 3-4% less accurate (data not shown). Of the 405 dysregulated genes in both Discovery and Replication subjects, 24.2% (98/405; Hyp. P=2.7e-48) were represented in these four modules. Logistic regression with repeated (3×) 10-fold cross-validation and ROC analysis displayed high AUC in both Discovery (training set) and Replication (independent validation test set) toddlers with 82.5% and 75% accuracy, respectively (FIG. 4C, D; Table 14). While specificity remained high across the different class comparisons, accuracy and sensitivity decreased as the samples size was reduced (FIG. 4D).

Characteristics of Genes in the Classification Signature

Figure 4E:
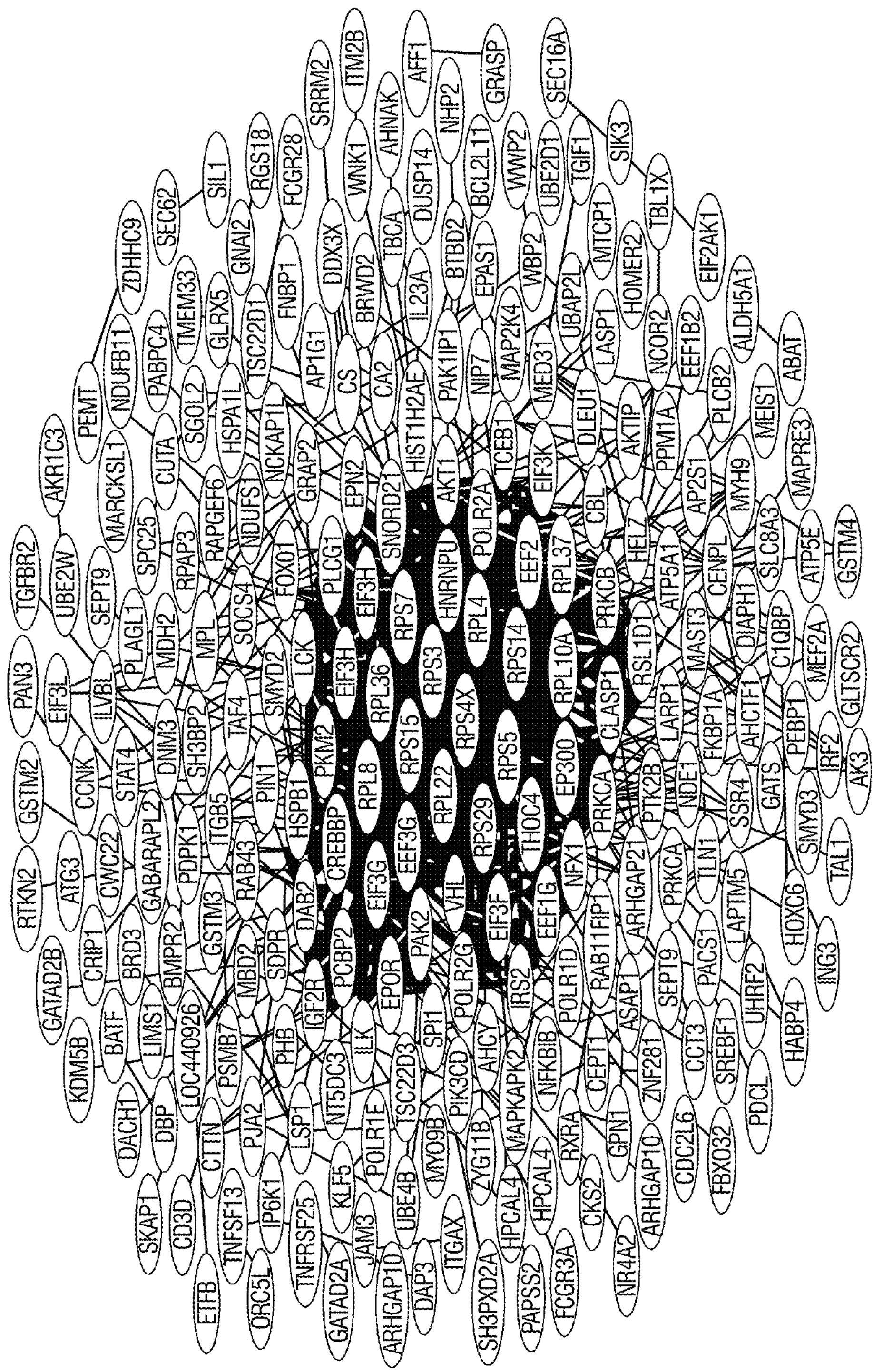

Metacore analysis of the four modules classifier displayed significant enrichment in translation and immune/inflammation genes (Table 14). DAPPLE analysis (broadinstitute.org/mpg/dapple)[20] of these gene modules revealed a statistical enrichment for protein-protein interaction (P<0.001). We next created a classification network based on the genes with the highest number of interactions. Consistent with the enrichment findings, a substantial number of ribosomal and translation genes were positioned at the center of the network (FIG. 4E). Enrichment analysis of the DAPPLE priority genes confirmed translation initiation as top process network (P=4e-18). Moreover, 17.2% of the classifier genes (131/762; Hyp. P=0.046) were located within Autism relevant CNVs (mindspec.org/autdb.html) of size below 1 Mb. This is in line with previous findings[21] suggesting CNVs as one potential genetic mechanism of gene expression dysregulation[22].

Comparison with recently reported classifiers[23,24] displayed modest to low overlap in gene content. Twelve (12/55) and eighteen (18/43) reported genes were differentially expressed in the Discovery subjects with only two and one genes, respectively, were present in our classifier (Table 15).

Prediction Performance and Subject Characteristics

Figure 11:
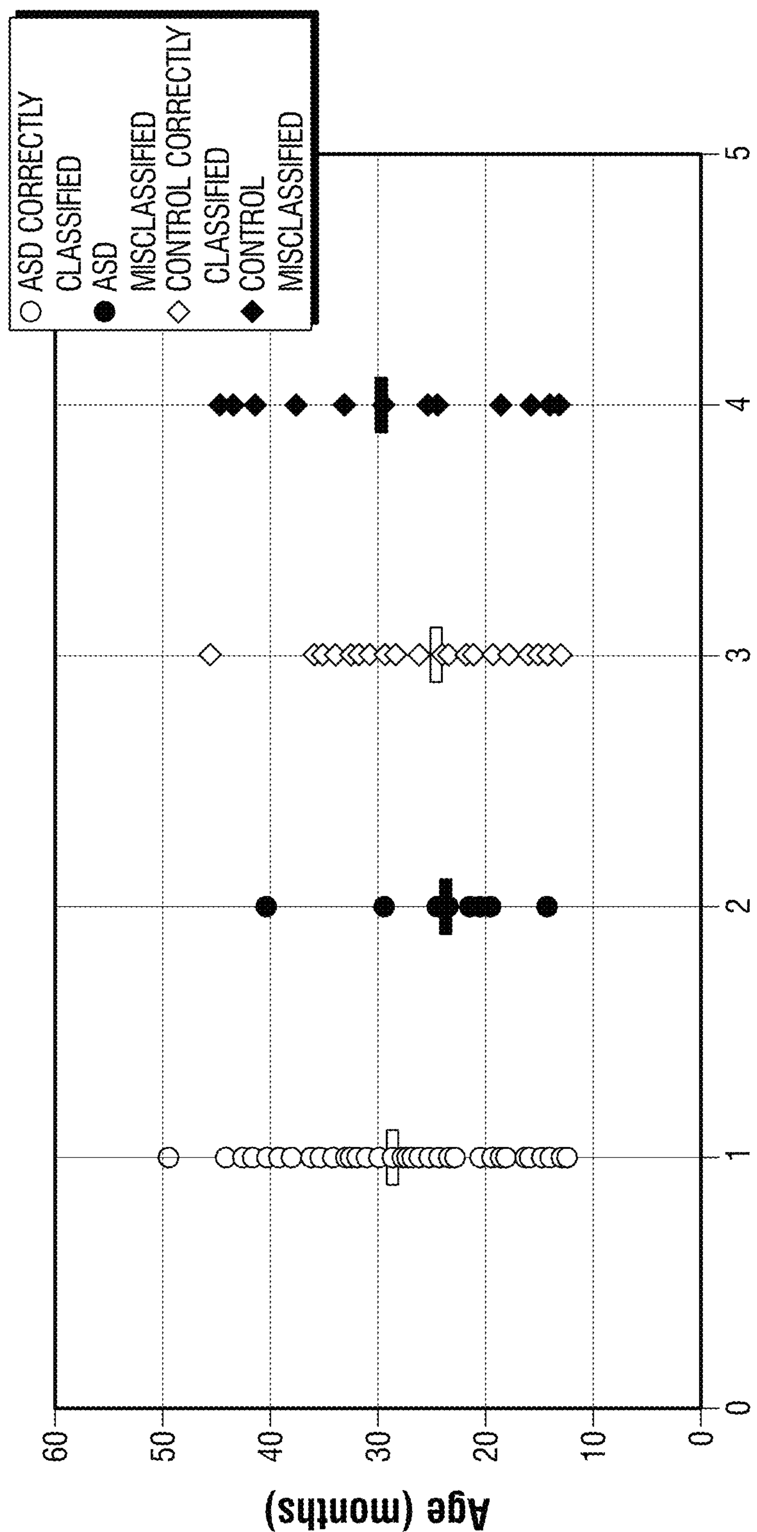
FIG. 11 Plot of classifier prediction performance relative to subject's age. Distribution of subject age separated by the accuracy of the classifier.
Figure 12:
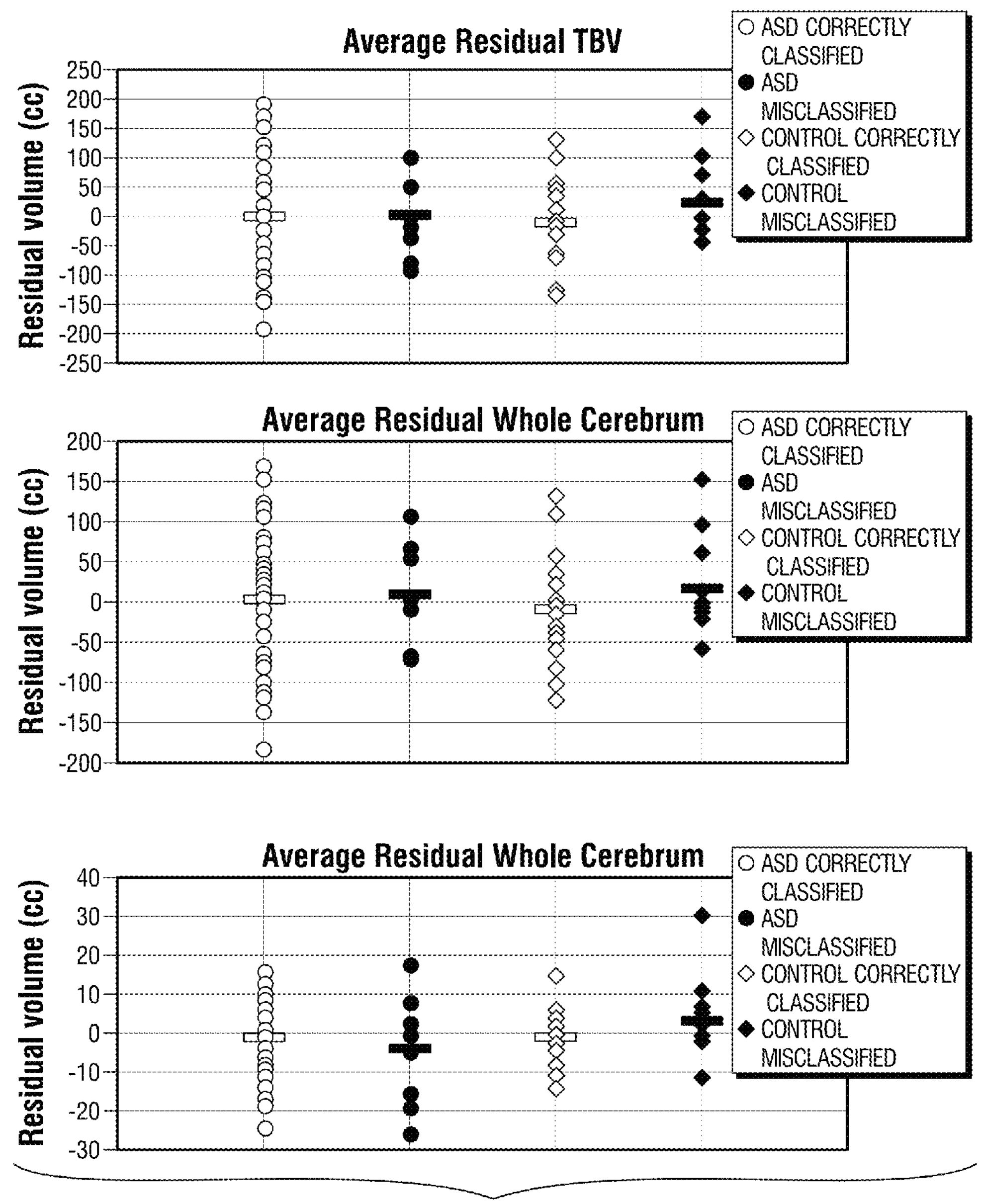
FIG. 12 Plots of the prediction performance and age-corrected total brain volume (TBV), whole cerebrum and cerebellum measures.

Prediction performance of all classified subjects (n=215) was correlated with age, diagnostic sub-groups, clinical and brain measures. Misclassified ASD toddlers were significantly younger, and misclassified control toddlers were significantly older than their correctly classified peers (FIG. 11); no other measure was found to be significantly different (FIG. 12).

A majority of the subjects were Caucasian, Hispanic or Mixed (58.4%, 22.4%, and 12.6% respectively). Of these groups, Mixed and Hispanic subjects were more accurately classified (97% and 88%), compared to Caucasians (74%). At a 0.5 threshold, 12 of the 14 miss-classified ASD subjects were genotyped for CNV analyses. A rare CNV of known ASD etiology, CNTNAP2 duplication, was found in only one subject (Table 7).

TABLE 7

CNV analysis of mis-classified ASD subjects

| SubjectID | CNV location (hg18) | Size (bp) | DEL/ DUP | Genes involved |
|---|---|---|---|---|
| X3F5T | chr6: 169182781-169723045 | 540,264 | DUP | AK055570, BX648586, THBS2, WDR27 |
| X3F5T | chr7: 147713357-147819466 | 106,109 | DUP | CNTNAP2, LOC392145 |
| M8K5X | chr20: 47589174-47611381 | 22,207 | DEL | PTGIS |
| Y2B4P | chr15: 21744675-21778678 | 34,003 | DEL | Intergenic (NDN, AK124131) |
| J3L5W | chr1: 231796069-231813713 | 17,644 | DEL | Intergenic (KIAA1804, KCNK1) |
| L5S3Z | chr1: 242582713-242601647 | 18,934 | DEL | C1orf100 |
| X2H3X | chr12: 72374075-72391780 | 17,705 | DUP | Intergenic (TRHDE, BC061638) |
| J3L5W | chr14: 19754117-19825127 | 71,010 | DEL | OR11H4, OR11H6 |
| S3D7F | chr5: 12578748-12906570 | 327,822 | DEL | AY328033, AY330599 |
| Z3W7W | chr6: 132884089-132906241 | 22,152 | DEL | TAAR9 |

DEL = heterozygous deletion, DUP = duplication.
Reference genome hg18

TABLE 8

Process Networks (Metacore) enrichment for the seven module with significant association with neuroanatomic measures by WGCNA across ASD and control toddlers

| # | Networks | pValue | Ratio |
|---|---|---|---|
| | GreenYellow_genelist | | |
| 1 | Cell cycle_Core | 9.34E−40 | 40/115 |
| 2 | Cell cycle_Mitosis | 2.27E−36 | 44/179 |
| 3 | Cytoskeleton_Spindle microtubules | 2.05E−30 | 33/109 |
| 4 | Cell cycle_S phase | 2.59E−29 | 36/149 |
| 5 | Cell cycle_G2-M | 9.81E−17 | 29/206 |
| 6 | Cell cycle_G1-S | 1.14E−10 | 20/163 |
| 7 | Cytoskeleton_Cytoplasmic microtubules | 6.53E−07 | 13/115 |
| 8 | DNA damage_DBS repair | 7.23E−07 | 13/116 |
| 9 | DNA damage_Checkpoint | 1.56E−06 | 13/124 |
| 10 | Cell cycle_Meiosis | 1.77E−06 | 12/106 |
| 11 | Proteolysis_Ubiquitin-proteasomal proteolysis | 1.67E−04 | 12/166 |
| | Cyan_genelist | | |
| 1 | Cytoskeleton_Regulation of cytoskeleton rearrangement | 2.87E−04 | 7/183 |
| 2 | Development_Hemopoiesis, Erythropoietin pathway | 3.79E−04 | 6/136 |
| 3 | Cell adhesion_Integrin-mediated cell-matrix adhesion | 7.38E−04 | 7/214 |
| 4 | Cytoskeleton_Actin filaments | 1.47E−03 | 6/176 |
| | Turquoise_genelist | | |
| 1 | Inflammation_Interferon signaling | 1.70E−06 | 24/110 |
| 2 | Inflammation_TREM1 signaling | 3.14E−06 | 28/145 |
| 3 | Inflammation_NK cell cytotoxicity | 4.48E−06 | 30/164 |

TABLE 8-continued

Process Networks (Metacore) enrichment for the seven module with significant association with neuroanatomic measures by WGCNA across ASD and control toddlers

| # | Networks | pValue | Ratio |
|---|---|---|---|
| 4 | Development_Blood vessel morphogenesis | 6.73E−06 | 37/228 |
| 5 | Protein folding_Folding in normal condition | 7.32E−06 | 24/119 |
| 6 | Immune response_TCR signaling | 1.52E−05 | 30/174 |
| 7 | Inflammation_Amphoterin signaling | 6.26E−05 | 22/118 |
| 8 | Chemotaxis | 8.33E−05 | 24/137 |
| 9 | Proliferation_Negative regulation of cell proliferation | 1.15E−04 | 29/184 |
| 10 | Protein folding_Response to unfolded proteins | 1.58E−04 | 15/69 |
| 11 | Apoptosis_Death Domain receptors & caspases in apoptosis | 3.30E−04 | 21/123 |
| | MidnightBlue_genelist | | |
| 1 | Cell adhesion_Integrin-mediated cell-matrix adhesion | 5.41E−10 | 18/214 |
| 2 | Cell adhesion_Platelet-endothelium-leucocyte interactions | 1.24E−08 | 15/174 |
| 3 | Cell adhesion_Platelet aggregation | 2.20E−07 | 13/158 |
| 4 | Muscle contraction | 4.10E−06 | 12/173 |
| 5 | Blood coagulation | 4.26E−05 | 8/94 |
| 6 | Cytoskeleton_Actin filaments | 7.00E−04 | 9/176 |
| 7 | Cytoskeleton_Regulation of cytoskeleton rearrangement | 9.26E−04 | 9/183 |
| 8 | Inflammation_Histamine signaling | 2.57E−03 | 9/212 |
| 9 | Proliferation_Positive regulation cell proliferation | 3.40E−03 | 9/221 |
| 10 | Development_Skeletal muscle development | 3.70E−03 | 7/144 |
| | Grey60_genelist | | |
| 1 | Protein folding_ER and cytoplasm | 2.34E−08 | 6/45 |
| 2 | Protein folding_Response to unfolded proteins | 3.21E−07 | 6/69 |
| 3 | Apoptosis_Endoplasmic reticulum stress pathway | 1.28E−06 | 6/87 |
| 4 | Protein folding_Folding in normal condition | 1.20E−04 | 5/119 |
| 5 | Immune response_Phagosome in antigen presentation | 4.34E−04 | 6/243 |
| 6 | Immune response_Antigen presentation | 1.23E−03 | 5/197 |
| 7 | Muscle contraction_Nitric oxide signaling in the cardiovascular system | 1.72E−03 | 4/125 |
| 8 | Protein folding_Protein folding nucleus | 1.76E−03 | 3/58 |
| | Yellow_genelist | | |
| 1 | Translation_Regulation of initiation | 3.13E−08 | 19/127 |
| 2 | Translation_Translation in mitochondria | 8.83E−07 | 21/187 |
| 3 | Signal Transduction_Cholecystokinin signaling | 9.71E−06 | 14/106 |
| 4 | Inflammation_Neutrophil activation | 1.17E−04 | 19/219 |
| 5 | Immune response_Phagocytosis | 1.40E−04 | 19/222 |
| 6 | Development_Hemopoiesis, Erythropoietin pathway | 1.61E−04 | 14/136 |
| 7 | Cell adhesion_Integrin priming | 2.75E−04 | 12/110 |
| 8 | Development_EMT_Regulation of epithelial-to-mesenchymal transition | 5.07E−04 | 18/226 |
| 9 | Reproduction_Spermatogenesis, motility and copulation | 5.94E−04 | 18/229 |
| 10 | Signal transduction_WNT signaling | 7.85E−04 | 15/177 |
| 11 | Apoptosis_Anti-Apoptosis mediated by external signals via MAPK and JAK/STAT | 8.82E−04 | 15/179 |
| | LightGreen_genelist | | |
| 1 | Inflammation_NK cell cytotoxicity | 4.90E−16 | 18/164 |
| 2 | Immune response_Antigen presentation | 3.35E−05 | 9/197 |
| 3 | Inflammation_Jak-STAT Pathway | 1.57E−04 | 8/188 |
| 4 | Chemotaxis | 9.52E−04 | 6/137 |
| 5 | Cell adhesion_Leucocyte chemotaxis | 1.53E−03 | 7/205 |

TABLE 9

Process networks (Metacore) enrichment for each of the 2 modules associated with neuroanatomic measures from the WGCNA analysis using control toddlers

| # | Networks | pValue | Ratio |
|---|---|---|---|
| | Magenta_genelist | | |
| 1 | Cell cycle_Core | 1.73E−39 | 37/115 |
| 2 | Cell cycle_Mitosis | 9.92E−36 | 40/179 |
| 3 | Cell cycle_S phase | 1.62E−30 | 34/149 |
| 4 | Cytoskeleton_Spindle microtubules | 1.49E−29 | 30/109 |
| 5 | Cell cycle_G2-M | 1.05E−19 | 29/206 |
| 6 | Cell cycle_G1-S | 7.99E−09 | 16/163 |
| 7 | DNA damage_Checkpoint | 1.02E−07 | 13/124 |
| 8 | Cell cycle_Meiosis | 8.62E−06 | 10/106 |
| 9 | DNA damage_MMR repair | 4.69E−05 | 7/59 |
| 10 | Cytoskeleton_Cytoplasmic microtubules | 1.09E−04 | 9/115 |
| | MidnightBlue_genelist | | |
| 1 | Protein folding_ER and cytoplasm | 6.17E−06 | 4/45 |
| 2 | Protein folding_Response to unfolded proteins | 3.43E−05 | 4/69 |
| 3 | Immune response_Phagosome in antigen presentation | 4.45E−04 | 5/243 |
| 4 | Proteolysis_Ubiquitin-proteasomal proteolysis | 1.02E−03 | 4/166 |
| 5 | Apoptosis_Endoplasmic reticulum stress pathway | 1.71E−03 | 3/87 |
| 6 | Immune response_Antigen presentation | 1.92E−03 | 4/197 |
| 7 | Protein folding_Folding in normal condition | 4.17E−03 | 3/119 |
| 8 | Signal transduction_Androgen receptor nuclear signaling | 4.90E−03 | 3/126 |

TABLE 10

Process networks (Metacore) enrichment for each of the 11 modules associated with neuroanatomic measures from the WGCNA analysis using ASD toddlers

| # | Networks | pValue | Ratio |
|---|---|---|---|
| | Yellow_genelist | | |
| 1 | Inflammation_NK cell cytotoxicity | 7.67E−08 | 23/164 |
| 2 | Cell adhesion_Leucocyte chemotaxis | 1.22E−06 | 24/205 |
| 3 | Chemotaxis | 1.29E−06 | 19/137 |
| 4 | Inflammation_TREM1 signaling | 1.21E−05 | 18/145 |
| 5 | Immune response_TCR signaling | 1.28E−05 | 20/174 |
| 6 | Immune response_BCR pathway | 2.14E−05 | 17/137 |
| 7 | Inflammation_Innate inflammatory response | 2.31E−05 | 20/181 |
| 8 | Immune response_T helper cell differentiation | 2.85E−05 | 17/140 |
| 9 | Development_Blood vessel morphogenesis | 7.41E−05 | 22/228 |
| 10 | Signal transduction_ERBB-family signaling | 1.39E−04 | 11/75 |
| | Salmon_genelist | | |
| 1 | Cell adhesion_Integrin-mediated cell-matrix adhesion | 7.07E−08 | 16/214 |
| 2 | Muscle contraction | 1.89E−07 | 14/173 |
| 3 | Cell adhesion_Platelet-endothelium-leucocyte interactions | 2.03E−07 | 14/174 |
| 4 | Cell adhesion_Platelet aggregation | 2.97E−06 | 12/158 |
| 5 | Blood coagulation | 6.50E−05 | 8/94 |
| 6 | Cytoskeleton_Actin filaments | 1.07E−03 | 9/176 |
| 7 | Proliferation_Positive regulation cell proliferation | 1.44E−03 | 10/221 |
| | Royalblue_genelist | | |
| 1 | Protein folding_Response to unfolded proteins | 3.21E−07 | 6/69 |
| 2 | Apoptosis_Endoplasmic reticulum stress pathway | 2.67E−05 | 5/87 |
| 3 | Protein folding_ER and cytoplasm | 3.34E−05 | 4/45 |
| 4 | Immune response_Phagosome in antigen presentation | 5.02E−05 | 7/243 |
| 5 | Immune response_Antigen presentation | 1.23E−03 | 5/197 |
| 6 | Muscle contraction_Nitric oxide signaling in the cardiovascular system | 1.72E−03 | 4/125 |
| | Brown_genelist | | |
| 1 | Development_Blood vessel morphogenesis | 2.08E−06 | 26/228 |
| 2 | Chemotaxis | 1.52E−04 | 16/137 |
| 3 | Cell adhesion_Leucocyte chemotaxis | 2.87E−04 | 20/205 |
| 4 | Immune response_IL-5 signalling | 3.71E−04 | 8/44 |
| 5 | Apoptosis_Death Domain receptors & caspases in apoptosis | 5.10E−04 | 14/123 |
| 6 | Proliferation_Negative regulation of cell proliferation | 5.57E−04 | 18/184 |

TABLE 10-continued

Process networks (Metacore) enrichment for each of the 11 modules associated with neuroanatomic measures from the WGCNA analysis using ASD toddlers

| # | Networks | pValue | Ratio |
|---|---|---|---|
| 7 | Inflammation_Neutrophil activation | 6.78E−04 | 20/219 |
| 8 | Reproduction_Feeding and Neurohormone signaling | 1.09E−03 | 19/211 |
| 9 | Reproduction_Progesterone signaling | 1.22E−03 | 19/213 |
| 10 | Development_Hedgehog signaling | 1.80E−03 | 21/254 |
| | Purple_genelist | | |
| 1 | Cell cycle_Core | 1.03E−43 | 42/115 |
| 2 | Cell cycle_Mitosis | 1.08E−30 | 39/179 |
| 3 | Cell cycle_S phase | 5.25E−30 | 36/149 |
| 4 | Cytoskeleton_Spindle microtubules | 3.84E−24 | 28/109 |
| 5 | Cell cycle_G2-M | 3.03E−17 | 29/206 |
| 6 | Cell cycle_G1-S | 5.30E−11 | 20/163 |
| 7 | DNA damage_Checkpoint | 6.06E−06 | 12/124 |
| 8 | DNA damage_DBS repair | 1.83E−05 | 11/116 |
| 9 | DNA damage_MMR repair | 1.59E−04 | 7/59 |
| 10 | DNA damage_BER-NER repair | 3.34E−04 | 9/110 |
| | Grey60_genelist | | |
| 1 | Translation_Translation initiation | 1.35E−09 | 11/171 |
| 2 | Translation_Elongation-Termination | 2.66E−04 | 7/233 |
| | Green_genelist | | |
| 1 | Inflammation_Interferon signaling | 1.18E−31 | 35/110 |
| 2 | Immune response_Innate immune response to RNA viral infection | 4.28E−11 | 16/84 |
| 3 | Inflammation_Inflammasome | 2.45E−06 | 13/118 |
| 4 | Immune response_Antigen presentation | 1.50E−04 | 14/197 |
| 5 | Inflammation_IFN-gamma signaling | 1.91E−04 | 10/110 |
| 6 | Inflammation_Complement system | 2.35E−04 | 8/73 |
| 7 | Chemotaxis | 2.75E−04 | 11/137 |
| | Black_genelist | | |
| 1 | Immune response_TCR signaling | 2.32E−05 | 11/174 |
| 2 | Translation_Regulation of initiation | 3.29E−04 | 8/127 |

TABLE 11

Process Networks (Metacore) enrichment of the Discovery DE genes

| # | Networks | pValue | Ratio | # | Map folders | pValue | Ratio |
|---|---|---|---|---|---|---|---|
| 1 | Apoptosis_Apoptotic nucleus | 4.00E−07 | 43/159 | 1 | Immune system response | 6.72E−24 | 169/1000 |
| 2 | Apoptosis_Death Domain receptors & caspases in apoptosis | 3.87E−06 | 34/123 | 2 | Inflammatory response | 2.80E−14 | 122/775 |
| 3 | Immune response_Phagosome in antigen presentation | 1.09E−05 | 54/243 | 3 | DNA-damage response | 1.66E−13 | 71/354 |
| 4 | Immune response_Phagocytosis | 1.58E−05 | 50/222 | 4 | Cell cycle and its regulation | 1.06E−12 | 89/516 |
| 5 | Immune response_TCR signaling | 6.83E−05 | 40/174 | 5 | Apoptosis | 3.71E−12 | 135/953 |
| 6 | Translation_Translation initiation | 1.01E−04 | 39/171 | 6 | Cell differentiation | 5.52E−10 | 127/940 |
| 7 | Inflammation_Interferon signaling | 1.35E−04 | 28/110 | 7 | Tissue remodeling and wound repair | 1.11E−09 | 86/557 |
| 8 | Apoptosis_Anti-apoptosis mediated by external signals via NF-kB | 1.59E−04 | 28/111 | 8 | Protein synthesis | 2.93E−09 | 56/306 |
| 9 | Cell adhesion_Leucocyte chemotaxis | 1.67E−04 | 44/205 | 9 | Vascular development (Angiogenesis) | 1.88E−08 | 81/543 |
| 10 | Inflammation_IFN-gamma signaling | 7.96E−04 | 26/110 | 10 | Cystic fibrosis disease | 3.70E−08 | 90/636 |
| 11 | Transcription_mRNA processing | 1.07E−03 | 34/160 | 11 | Calcium signaling | 1.95E−07 | 70/469 |
| 12 | Signal Transduction_TGF-beta, GDF and Activin signaling | 1.09E−03 | 33/154 | 12 | Protein degradation | 2.55E−07 | 47/269 |
| 13 | Cell cycle_Mitosis | 1.13E−03 | 37/179 | 13 | Mitogenic signaling | 7.87E−07 | 78/562 |
| 14 | Cytoskeleton_Actin filaments | 1.59E−03 | 36/176 | 14 | Obesity | 1.60E−04 | 33/211 |
| 15 | Cell adhesion_Platelet aggregation | 1.71E−03 | 33/158 | 15 | Myogenesis regulation | 1.74E−04 | 19/95 |
| 16 | Reproduction_Progesterone signaling | 2.63E−03 | 41/213 | 16 | Transcription regulation | 4.46E−04 | 15/71 |
| 17 | Proteolysis_Proteolysis in cell cycle and apoptosis | 2.64E−03 | 27/125 | 17 | Hypoxia response regulation | 4.64E−04 | Nov-43 |
| 18 | Reproduction_FSH-beta signaling pathway | 4.07E−03 | 32/160 | 18 | Hematopoiesis | 2.30E−03 | 40/313 |
| 19 | Cell cycle_G2-M | 4.45E−03 | 39/206 | 19 | Cardiac Hypertrophy | 4.62E−03 | 31/236 |
| 20 | Signal Transduction_Cholecystokinin signaling | 4.99E−03 | 23/106 | 20 | Blood clotting | 9.88E−03 | 34/279 |
| 21 | Cytoskeleton_Regulation of cytoskeleton rearrangement | 5.79E−03 | 35/183 | | | | |
| 22 | Development_Regulation of angiogenesis | 6.11E−03 | 41/223 | | | | |
| 23 | Development_Melanocyte development and pigmentation | 6.80E−03 | 13/50 | | | | |
| 24 | Inflammation_IL-4 signaling | 6.98E−03 | 24/115 | | | | |
| 25 | Proteolysis_Ubiquitin-proteasomal proteolysis | 7.21E−03 | 32/166 | | | | |
| 26 | Inflammation_Neutrophil activation | 7.52E−03 | 40/219 | | | | |

TABLE 12

Pathway comparison between discovery and replication datasets

| # | Map folders | −log (pValue) | pValue | err(−log (pValue)) | Ratio |
|---|---|---|---|---|---|
| 1 | DNA-damage response | 12.6825635 | 2.08E−13 | 0.007 | 115/354 |
| | | 12.87386859 | 1.34E−13 | | |
| 2 | Mitogenic signaling | 5.963371105 | 1.09E−06 | 0.01 | 131/564 |
| | | 6.084336396 | 8.24E−07 | | |

TABLE 12-continued

Pathway comparison between discovery and replication datasets

| # | Map folders | −log (pValue) | pValue | err(−log (pValue)) | Ratio |
|---|---|---|---|---|---|
| 3 | Hematopoiesis | 2.603451962 | 2.49E−03 | 0.023 | 66/313 |
| | | 2.72607322 | 1.88E−03 | | |
| 4 | Cardiac Hypertrophy | 2.307858391 | 4.92E−03 | 0.024 | 50/236 |
| | | 2.422163659 | 3.78E−03 | | |

TABLE 12-continued

Pathway comparison between discovery and replication datasets

| # | Map folders | −log (pValue) | pValue | err(−log (pValue)) | Ratio |
|---|---|---|---|---|---|
| 5 | Retinoid signaling | 0.201280315<br>0.216596719 | 6.29E−01<br>6.07E−01 | 0.037 | 13/105 |
| 6 | Androgen signaling | 0.439615077<br>0.401100113 | 3.63E−01<br>3.97E−01 | 0.046 | 32/224 |
| 7 | Lipid Biosynthesis and regulation | 0.300856313<br>0.334325219 | 5.00E−01<br>4.63E−01 | 0.053 | 51/389 |
| 8 | Transcription regulation | 3.33003263<br>2.960189446 | 4.68E−04<br>1.10E−03 | 0.059 | 25/71 |
| 9 | Neuro-transmission | 0.416914634<br>0.318216234 | 3.83E−01<br>4.81E−01 | 0.134 | 94/720 |
| 10 | Cystic fibrosis disease | 7.338376591<br>5.052909536 | 4.59E−08<br>8.85E−06 | 0.184 | 142/636 |
| 11 | Vascular development (Angiogenesis) | 8.300162274<br>5.156580335 | 5.01E−09<br>6.97E−06 | 0.234 | 123/553 |
| 12 | Cell cycle and its regulation | 11.86264589<br>19.1562068 | 1.37E−12<br>6.98E−20 | 0.235 | 158/516 |
| 13 | Vasodilation | 0.991825816<br>1.67325462 | 1.02E−01<br>2.12E−02 | 0.256 | 65/402 |
| 14 | Apoptosis | 11.57348874<br>6.646276062 | 2.67E−12<br>2.26E−07 | 0.27 | 206/964 |
| 15 | Cell differentiation | 9.182897596<br>5.207328211 | 6.56E−10<br>6.20E−06 | 0.276 | 197/958 |
| 16 | Vasocon-striction | 0.424927674<br>0.783570169 | 3.76E−01<br>1.65E−01 | 0.297 | 51/357 |
| 17 | Myogenesis regulation | 3.735654493<br>1.845576027 | 1.84E−04<br>1.43E−02 | 0.339 | 28/95 |
| 18 | Visual perception | 0.187353984<br>0.080451241 | 6.50E−01<br>8.31E−01 | 0.399 | 15/133 |
| 19 | Oxidative stress regulation | 0.351542406<br>0.844967771 | 4.45E−01<br>1.43E−01 | 0.412 | 93/697 |
| 20 | Calcium signaling | 6.633763876<br>2.38341947 | 2.32E−07<br>4.14E−03 | 0.471 | 101/469 |
| 21 | Tissue remodeling and wound repair | 9.020315<br>3.098542 | 9.54E−10<br>7.97E−04 | 0.489 | 126/562 |
| 22 | Nicotine action | 0.160836<br>0.052566 | 6.91E−01<br>8.86E−01 | 0.507 | 21/229 |
| 23 | Estrogen signaling | 0.32413<br>0.993962 | 4.74E−01<br>1.01E−01 | 0.508 | 43/287 |
| 24 | Diuresis | 0.092696<br>0.292771 | 8.08E−01<br>5.10E−01 | 0.519 | 13/139 |
| 25 | Protein degradation | 6.535809<br>1.91364 | 2.91E−07<br>1.22E−02 | 0.547 | 65/269 |
| 26 | Protein synthesis | 8.461803<br>2.360215 | 3.45E−09<br>4.36E−03 | 0.564 | 79/306 |
| 27 | Obesity | 3.377786<br>0.935168 | 4.19E−04<br>1.16E−01 | 0.566 | 41/203 |
| 28 | Inflammatory response | 13.93779<br>3.775208 | 1.15E−14<br>1.68E−04 | 0.574 | 179/790 |
| 29 | Nucleotide metabolism and its regulation | 0.039482<br>0.009839 | 9.13E−01<br>9.78E−01 | 0.601 | 42/401 |
| 30 | Hypoxia response regulation | 3.317314<br>0.748119 | 4.82E−04<br>1.79E−01 | 0.632 | 13/43 |
| 31 | Nuclear receptor signaling | 0.110138<br>0.515415 | 7.76E−01<br>3.05E−01 | 0.648 | 75/595 |
| 32 | Energy metabolism and its regulation | 0.311669<br>1.649752 | 4.88E−01<br>2.24E−02 | 0.682 | 133/927 |
| 33 | Blood clotting | 1.977572<br>0.313006 | 1.05E−02<br>4.86E−01 | 0.727 | 48/279 |
| 34 | Immune system response | 23.03588<br>3.06118 | 9.21E−24<br>8.69E−04 | 0.765 | 233/1007 |
| 35 | Spermato-genesis | 1.540909<br>0.098378 | 2.88E−02<br>7.97E−01 | 0.88 | 6/22 |
| 36 | Phospholipid Metabolism | 0.004935<br>0.108128 | 9.89E−01<br>7.80E−01 | 0.912 | 17/205 |
| 37 | Cholesterol and bile acid homeostasis | 4.34E−05<br>0.015158 | 1.00E+00<br>9.66E−01 | 0.995 | 38/471 |
| 38 | Aminoacid metabolism and its regulation | 0<br>4.34E−05 | 1.00E+00<br>1.00E+00 | 1 | 69/944 |
| 39 | Vitamin and cofactor metabolism and its regulation | 0<br>0 | 1.00E+00<br>1.00E+00 | 1 | 34/688 |

TABLE 13

Commonly dysregulated pathways in discovery and replication toddlers

| # | Map folders | -log(pValue) | pValue | Ratio |
|---|---|---|---|---|
| 1 | DNA-damage response | 6.598599 | 2.52E−07 | 20/354 |
| 2 | Cell cycle and its regulation | 5.160019 | 6.92E−06 | 22/516 |
| 3 | Apoptosis | 4.645892 | 2.26E−05 | 31/964 |
| 4 | Vascular development (Angiogenesis) | 4.177832 | 6.64E−05 | 21/553 |
| 5 | Obesity | 2.446238 | 3.58E−03 | 9/203 |
| 6 | Immune system response | 2.430275 | 3.71E−03 | 26/1007 |
| 7 | Cell differentiation | 2.406936 | 3.92E−03 | 25/958 |
| 8 | Tissue remodeling and wound repair | 2.353302 | 4.43E−03 | 17/562 |
| 9 | Cardiac Hypertrophy | 2.025304 | 9.43E−03 | 9/236 |
| 10 | Mitogenic signaling | 1.977159 | 1.05E−02 | 16/564 |

TABLE 14

Process Networks and Pathway Maps (Metacore) enrichment of the four genes modules used as classifier

| # | | -log(pValue) | pValue | Ratio |
|---|---|---|---|---|
| | Networks | | | |
| 1 | Translation_Translation initiation | 9.130416292 | 7.41E−10 | 27/171 |
| 2 | Inflammation_IFN-gamma signaling | 5.798876103 | 1.59E−06 | 17/110 |
| 3 | Translation_Elongation-Termination | 5.696587929 | 2.01E−06 | 26/233 |
| 4 | Translation_Elongation-Termination_test | 5.696587929 | 2.01E−06 | 26/233 |
| 5 | Cell adhesion_Platelet aggregation | 5.322575562 | 4.76E−06 | 20/158 |
| 6 | Immune response_Phagocytosis | 5.056653902 | 8.78E−06 | 24/222 |

TABLE 14-continued

Process Networks and Pathway Maps (Metacore) enrichment of the four genes modules used as classifier

| # | | -log(pValue) | pValue | Ratio |
|---|---|---|---|---|
| 7 | Cell adhesion_Leucocyte chemotaxis | 4.141102043 | 7.23E−05 | 21/205 |
| 8 | Signal Transduction_Cholecystokinin signaling | 4.088735829 | 8.15E−05 | 14/106 |
| 9 | Immune response_TCR signaling | 3.677367288 | 2.10E−04 | 18/174 |
| 10 | Cell cycle_G1-S Growth factor regulation | 3.513144645 | 3.07E−04 | 19/195 |
| | Map folders | | | |
| 1 | Immune system response | 11.64859025 | 2.25E−12 | 66/1007 |
| 2 | Protein synthesis | 9.648590248 | 2.25E−10 | 31/306 |
| 3 | Tissue remodeling and wound repair | 8.799423073 | 1.59E−09 | 42/562 |
| 4 | Inflammatory response | 7.558461961 | 2.76E−08 | 49/790 |
| 5 | Vascular development (Angiogenesis) | 7.451610582 | 3.54E−08 | 39/553 |
| 6 | Calcium signaling | 7.297741837 | 5.04E−08 | 35/469 |
| 7 | Cell differentiation | 6.130416292 | 7.41E−07 | 52/958 |
| 8 | Mitogenic signaling | 5.813326133 | 1.54E−06 | 36/564 |
| 9 | Hypoxia response regulation | 5.684659523 | 2.07E−06 | 9/43 |
| 10 | Cystic fibrosis disease | 5.016779785 | 9.62E−06 | 37/636 |

TABLE 15

| | |
|---|---|
| Kong et al., signature genes overlapping the DE genes from the discovery subjects | ADAM10 AHNAK CREBBP IFNAR2KBTBD11 KIAA0247 KIDINS220 MGAT4A PTPRE ROCK1 SERINC3 ZNF12 |
| Glatt et al., signature genes overlapping the DE genes from the discovery subjects | ANKRD22 ANXA3 APOBEC3G C11orf75 C3orf38 CARD17 FCGR1A FCGR1B GBP1 GBP5 GCH1 IFI16 IL1RN LOC644852 PARP9 PLSCR1TAP1 VWF |
| Kong et al., signature genes overlapping with the four gene modules classifier | AHNAK CREBBP KBTBD11 KIAA0247 KIDINS220 ROCK1 |
| Glatt et al., signature genes overlapping with the four gene modules classifier | VWF |

TABLE 16

| Gene Listing of Unique Differentially Expressed (DE) Genes | | | | | | | | | | | |
|---|---|---|---|---|---|---|---|---|---|---|---|
| SEPT6 | SEPT7 | SEPT9 | SEPT11 | SEPT14 | AAK1 | ABAT | ABCB1 | ABCC3 | ABCG1 | ABHD13 | ABHD14A |
| | ABHD14B | | ABHD15 | ABHD7 | ABL1 | ACAA1 | ACACB | ACAD11 | ACAD8 | ACADVL | ACD |
| | ACER2 | ACOT4 | ACOT9 | ACSL1 | ACSM3 | ACTA2 | ACTR2 | ACYP2 | ADAM10 | ADAM17 | ADAM19 |
| | ADAM28 | ADARB1 | ADCY7 | ADI1 | ADNP | ADNP2 | ADPRHL2 | | AES | AFF1 | AGAP8 |
| | AGER | AGPAT3 | AHCTF1 | AHCY | AHI1 | AHNAK | AIF1 | AIM2 | AIP | AIRE | AK2P2 |
| | AK3 | AK5 | AKAP7 | AKR1C3 | AKR1D1 | AKR7A3 | AKT1 | AKTIP | ALDH5A1 | ALG10B | ALG13 |
| | ALKBH7 | ALKBH8 | ALOX12 | ALOX5 | ALPK1 | ALPP | ALS2CR14 | | AMOTL2 | AMY1A | AMY1B |
| | AMY2B | AMZ2 | ANGPT1 | ANKRD12 | | ANKRD22 | | ANKRD28 | | ANKRD36 | |
| | ANKRD41 | | ANKRD44 | | ANP32A | ANP32C | ANXA1 | ANXA11 | ANXA2 | ANXA2P1 | ANXA2P3 |
| | ANXA3 | ANXA4 | AP1B1 | AP1G1 | AP1G2 | AP1M2 | AP1S1 | AP2A1 | AP2M1 | AP2S1 | APBA2 |
| | API5 | APOA1BP | APOBEC3G | | APOL2 | APPL2 | AQP12A | ARAP2 | ARAP3 | ARF1 | ARF6 |
| | ARFGAP3 | ARHGAP10 | | ARHGAP17 | | ARHGAP21 | | ARHGAP25 | | ARHGAP27 | |
| | ARHGAP30 | | ARHGAP9 | | ARHGDIA | | ARHGEF18 | | ARHGEF3 | | ARID1A |
| | ARID2 | ARID4A | ARID4B | ARL17B | ARL4C | ARL5A | ARL6IP1 | ARMC5 | ARRB2 | ARRDC2 | ASAP1 |
| | ASB1 | ASCC3 | ASMTL | ATG10 | ATG2A | ATG3 | ATG4C | ATHL1 | ATM | ATN1 | ATP1B1 |
| | ATP2B4 | ATP5A1 | ATP5D | ATP5E | ATP5O | ATP6V0C | ATP6V1C1 | | ATPGD1 | ATR | ATRX |
| | AXIN1 | AZIN1 | B3GALT6 | B3GAT1 | BAG4 | BATF | BATF2 | BAZ1B | BBX | BCAP31 | BCAS2 |
| | BCKDHA | BCL11B | BCL2 | BCL2A1 | BCL2L11 | BCL6 | BCL9 | BCL9L | BCOR | BCORL1 | BCR |
| | BEGAIN | BEX1 | BIN2 | BIRC3 | BIVM | BLNK | BMF | BMP8B | BMPR2 | BPGM | BRD3 |
| | BRD7P2 | BRDG1 | BRPF3 | BRWD1 | BRWD2 | BST1 | BTBD2 | BTF3 | BTK | BUB3 | C10orf104 |
| | C10orf35 | C10orf4 | C10orf47 | C10orf58 | C10orf76 | C11orf1 | C11orf2 | C11orf46 | C11orf63 | C11orf73 | C11orf75 |
| | C11orf82 | C12orf29 | C12orf30 | C12orf32 | C12orf65 | C13orf15 | C13orf18 | C14orf102 | C14orf11 | C14orf135 | C14orf138 |
| | C14orf19 | C14orf28 | C14orf32 | C14orf43 | C14orf82 | C15orf21 | C15orf26 | C15orf52 | C15orf57 | C16orf30 | C16orf53 |
| | C16orf57 | C16orf68 | C16orf69 | C17orf41 | C17orf45 | C17orf87 | C18orf10 | C18orf32 | C19orf12 | C19orf2 | C19orf25 |
| | C19orf39 | C19orf53 | C19orf56 | C19orf59 | C19orf6 | C19orf60 | C1D | C1GALT1 | C1GALT1C1 | | C1orf110 |
| | C1orf151 | C1orf166 | C1orf186 | C1orf43 | C1orf63 | C1orf71 | C1orf77 | C1orf85 | C1orf86 | C1orf9 | C1QB |
| | C1QBP | C20orf100 | C20orf108 | C20orf11 | C20orf196 | C20orf199 | C20orf29 | C20orf30 | C20orf4 | C20orf55 | C20orf94 |
| | C21orf33 | C21orf66 | C21orf7 | C22orf29 | C22orf32 | C22orf34 | C2orf15 | C2orf21 | C2orf69 | C2orf89 | C3orf10 |
| | C3orf17 | C3orf34 | C3orf38 | C3orf58 | C3orf63 | C4orf16 | C4orf32 | C4orf34 | C4orf43 | C5orf20 | C5orf4 |
| | C5orf41 | C5orf53 | C6orf150 | C6orf160 | C6orf170 | C6orf204 | C6orf211 | C6orf225 | C6orf48 | C6orf62 | C7orf11 |
| | C7orf28A | C7orf41 | C7orf70 | C8orf33 | C9orf109 | C9orf127 | C9orf130 | C9orf30 | C9orf5 | C9orf72 | C9orf80 |
| | C9orf85 | CA2 | CA5B | CABC1 | CABIN1 | CABP5 | CACYBP | CALM1 | CALML4 | CAMK1D | |
| | CAMSAP1L1 | | CANX | CAPS2 | CAPZA1 | CARD14 | CARD16 | CARD17 | CARS2 | CASP1 | CASP2 |
| | CASP4 | CASP5 | CASP8 | CAST | CBFB | CBL | CBR3 | CBS | CBWD1 | CBWD3 | CBX7 |
| | CCAR1 | CCDC115 | CCDC117 | CCDC147 | CCDC15 | CCDC16 | CCDC23 | CCDC25 | CCDC28B | CCDC50 | CCDC59 |
| | CCDC6 | CCDC65 | CCDC72 | CCDC82 | CCDC86 | CCDC90A | CCDC90B | CCDC91 | CCDC97 | CCL2 | CCL8 |
| | CCNG1 | CCNK | CCNL1 | CCNY | CCNYL1 | CCR4 | CCRL2 | CCS | CCT3 | CCT6P1 | CD164 |
| | CD1E | CD27 | CD274 | CD300LB | CD320 | CD3D | CD3E | CD3G | CD40LG | CD47 | CD6 |
| | CD74 | CD79B | CD84 | CD97 | CD99 | CDAN1 | CDC14A | CDC14B | CDC25B | CDC2L2 | CDC2L6 |
| | CDC42SE2 | | CDK2AP2 | CDK5RAP3 | | CEACAM1 | | CEACAM4 | | CECR1 | CENPL |
| | CENPV | CENTB2 | CENTD1 | CENTG2 | CENTG3 | CEP27 | CEP350 | CEP63 | CEP68 | CEPT1 | CERK |
| | CETN3 | CHCHD2 | CHD3 | CHD8 | CHES1 | CHM | CHML | CHMP2A | CHMP5 | CHORDC1 | |
| | CHP | CHPF2 | CICK0721Q.1 | | CIR1 | CITED4 | CKAP5 | CKS2 | CLASP1 | CLEC10A | CLEC11A |
| | CLEC12A | CLEC12B | CLEC4A | CLEC4D | CLEC7A | CLIC4 | CLIP1 | CLIP2 | CLIP3 | CLK1 | CLK3 |
| | CLN8 | CLSTN1 | CMIP | CMPK1 | CMTM3 | CMTM4 | CMTM7 | CNIH4 | CNN3 | CNNM3 | CNOT1 |
| | CNOT7 | COBRA1 | COL24A1 | COMMD7 | COMMD8 | COPS2 | COX11 | COX7A2L | CPEB3 | CPNE1 | CR1 |
| | CRBN | CREBBP | CREM | CRIP1 | CRIP2 | CRIPT | CROP | CRY2 | CRYZL1 | CS | CSDE1 |
| | CSE1L | CSF2RB | CSNK1A1L | | CSNK1E | CTAGE6 | CTDP1 | CTDSP1 | CTDSPL | CTNNB1 | CTRL |
| | CTSB | CTSC | CTSF | CTSL1 | CTTN | CUGBP2 | CUTA | CUTC | CUTL1 | CWC22 | CXCL5 |

TABLE 16-continued

| Gene Listing of Unique Differentially Expressed (DE) Genes | | | | | | | | | | |
|---|---|---|---|---|---|---|---|---|---|---|
| CXCR3 | CXCR6 | CXCR7 | CXorf12 | CXorf20 | CXorf21 | CXorf57 | CYB561D1 | | CYB5R1 | CYCSL1 |
| CYCSP52 | CYFIP2 | CYLD | CYLN2 | CYP20A1 | D4S234E | DAB2 | DACH1 | DAP | DAP3 | DAPK2 |
| DAPP1 | DBI | DBP | DBT | DCAF16 | DCAF7 | DCK | DCLRE1C | DCTN1 | DCTN6 | DCXR |
| DDHD1 | DDHD2 | DDIT4 | DDX27 | DDX3X | DDX3Y | DDX41 | DDX46 | DDX58 | DDX59 | DDX60 |
| DDX60L | DECR2 | DEDD | DENND2D | | DERL2 | DFFA | DGCR8 | DGKD | DHPS | DHRS3 |
| DHRS7 | DHX34 | DHX9 | DIAPH1 | DIP2B | DKFZp434K191 | | DKFZp686I15217 | | DKFZp761P0423 | |
| DLEU1 | DLEU2 | DLEU2L | DLGAP4 | DMWD | DMXL1 | DMXL2 | DNAJB14 | DNAJB2 | DNAJC25-GNG10 | |
| DNAJC30 | DNAJC7 | DNHD2 | DNHL1 | DNM3 | DNTT | DNTTIP2 | DOPEY2 | DPEP2 | DPM3 | DPP3 |
| DRD4 | DSC2 | DSTN | DTWD1 | DTX3L | DULLARD | | DUSP14 | DUSP22 | DYNLT3 | DYRK2 |
| ECHDC1 | ECT2 | EDAR | EDC3 | EEF1A1 | EEF1B2 | EEF1G | EEF2 | EEF2K | EFCAB2 | EIF2AK1 |
| EIF2AK4 | EIF2C2 | EIF2S3 | EIF3D | EIF3F | EIF3G | EIF3H | EIF3K | EIF3L | EIF4B | EIF4E |
| EIF5A | ELA1 | ELF2 | ELMO1 | ELOVL4 | ENDOD1 | ENO2 | ENO3 | EP300 | EP400 | EPAS1 |
| EPB41 | EPB49 | EPHA1 | EPHA10 | EPHA4 | EPN2 | EPOR | EPSTI1 | ERGIC1 | ERMN | ERMP1 |
| ERVWE1 | ESF1 | ESYT1 | ETFB | ETNK1 | EVI2B | EWSR1 | EXOC8 | FABP5 | FABP5L3 | FAHD1 |
| FAIM3 | FAM101B | FAM102A | FAM107B | FAM108B1 | | FAM10A4 | FAM116A | FAM119A | FAM120A | FAM122A |
| FAM125B | FAM126B | FAM134A | FAM134B | FAM13A | FAM153B | FAM173A | FAM195B | FAM19A2 | FAM26F | FAM3A |
| FAM40B | FAM62B | FAM65B | FAM72D | FAM73A | FAM84B | FAM91A2 | FANCL | FAS | FASTK | FBLN1 |
| FBLN2 | FBP1 | FBXL11 | FBXL3 | FBXO21 | FBXO3 | FBXO31 | FBXO32 | FBXO38 | FBXO44 | FBXO5 |
| FBXO6 | FCER1A | FCGBP | FCGR1A | FCGR1B | FCGR1C | FCGR2B | FCGR2C | FCGR3A | FCRL3 | FERMT3 |
| FEZ1 | FEZ2 | FFAR2 | FHL3 | FICD | FKBP14 | FKBP1A | FKBP1P1 | FKRP | FKTN | FLJ10088 |
| FLJ10916 | FLJ12078 | FLJ13611 | FLJ20444 | FLJ25363 | FLJ34047 | FLJ37396 | FLJ39639 | FLJ42627 | FLJ45256 | FLT3LG |
| FNBP1 | FNIP2 | FOXJ2 | FOXK1 | FOXO1 | FOXP1 | FTHL11 | FTHL16 | FTHL2 | FTHL3 | FTHL8 |
| FTO | FTSJ1 | FUT6 | FXYD5 | FYN | FYTTD1 | FZD7 | GABARAPL2 | | GABBR1 | GALNT3 |
| GALNT7 | GALT | GAR1 | GATAD2A | | GATAD2B | | GATS | GBA | GBP1 | GBP2 |
| GBP3 | GBP5 | GBP6 | GCC2 | GCET2 | GCH1 | GDI1 | GDPD1 | GDPD5 | GEMIN4 | GFI1B |
| GIMAP7 | GIPC1 | GIYD2 | GK | GKAP1 | GLG1 | GLRX5 | GLTSCR1 | GLTSCR2 | GMCL1 | GMPPB |
| GNAI2 | GNG10 | GNG5 | GNG7 | GNL3L | GNPDA2 | GNPTAB | GOLGA3 | GOLGA8B | | GOLPH3L |
| GOLPH4 | GOT2 | GP1BA | GPAM | GPBP1L1 | GPN1 | GPN3 | GPR1 | GPR128 | GPR141 | GPR180 |
| GPR65 | GPR68 | GPR84 | GPR97 | GPSM3 | GPX4 | GRAP2 | GRASP | GRB14 | GRN | GRPEL2 |
| GRWD1 | GSDM1 | GSDMB | GSTM1 | GSTM2 | GSTM3 | GSTM4 | GSTTP2 | GTF2IRD2B | | GTF3A |
| GTF3C6 | GTPBP8 | GUCY1A3 | | GUSBL1 | GVIN1 | HABP4 | HCCA2 | HCCS | HCFC1 | HCFC1R1 |
| HCLS1 | HCST | HEATR3 | HEBP1 | HECTD3 | HELZ | HEMGN | HERC1 | HERC2 | HERPUD2 | |
| HEXDC | HGD | HHEX | HIAT1 | HIBCH | HIGD2A | HINT3 | HIP1R | HIPK2 | HIST1H2AD | |
| HIST1H2AE | | HIST2H2AB | | HK1 | HLA-C | HLA-DRB4 | | HLA-DRB6 | | HLA-H |
| HM13 | HMBOX1 | HMGB1 | HMGN3 | HN1 | HNRNPA1L2 | | HNRNPK | HNRNPU | HNRPC | HNRPH1 |
| HNRPH3 | HNRPK | HNRPUL1 | | HOMER2 | HOOK1 | HOOK3 | HORMAD1 | | HOXC4 | HOXC6 |
| HPCAL4 | HPSE | HRSP12 | HSCB | HSH2D | HSP90AB4P | | HSPA13 | HSPA1L | HSPA9 | HSPB1 |
| HSPCAL3 | HVCN1 | HYAL3 | HYALP1 | HYOU1 | ICA1 | ICK | IDH2 | IDI1 | IFFO2 | IFI16 |
| IFI27 | IFI44 | IFI44L | IFI6 | IFIT3 | IFITM4P | IFNAR2 | IFT20 | IGF2BP2 | IGF2BP3 | IGF2R |
| IGFL3 | IKZF1 | IL10 | IL10RB | IL18RAP | IL19 | IL1RN | IL23A | IL25 | IL27 | IL27RA |
| IL4I1 | IL6ST | IL7R | ILF3 | ILK | ILVBL | IMMP1L | IMPA1 | IMPA2 | INADL | ING2 |
| ING3 | INPP4B | INSM1 | INTS1 | INTU | IP6K1 | IP6K2 | IPO13 | IQCB1 | IQGAP2 | IRAK1 |
| IRF2 | IRF5 | IRF7 | IRF9 | IRS2 | IRX3 | ISCA1 | ISG15 | ISG20L2 | ITFG1 | ITGAL |
| ITGAX | ITGB1BP1 | | ITGB5 | ITM2B | ITPKB | JAM3 | JARID1A | JARID2 | JUP | KATNAL1 |
| KBTBD11 | KCNA3 | KCNG1 | KCNH7 | KCTD12 | KCTD7 | KDM1B | KDM5B | KDM6B | KHDRBS1 | |
| KHNYN | KIAA0040 | KIAA0182 | KIAA0247 | KIAA0319L | | KIAA0355 | KIAA0408 | KIAA0776 | KIAA1026 | KIAA1033 |
| KIAA1147 | KIAA1279 | KIAA1324 | KIAA1430 | KIAA1545 | KIAA1704 | KIAA1715 | KIAA1737 | KIAA1881 | KIAA2026 | KIDINS220 |
| KIF13B | KIF21B | KIF22 | KIF2A | KIT | KLF12 | KLF5 | KLF6 | KLF9 | KLHL20 | KLHL24 |
| KLHL28 | KLRB1 | KLRG1 | KPNA2 | KPNA6 | KRCC1 | KREMEN1 | | KREMEN2 | | KRT40 |
| KRT73 | KRT8P9 | KRTAP19-6 | | KTELC1 | LACTB | LAPTM4A | | LAPTM4B | | LAPTM5 |
| LARGE | LARP1 | LARP1B | LASP1 | LASS6 | LAX1 | LCK | LCLAT1 | LCMT2 | LDHA | LDHB |

TABLE 16-continued

Gene Listing of Unique Differentially Expressed (DE) Genes

| | | | | | | | | | | |
|---|---|---|---|---|---|---|---|---|---|---|
| LDLRAP1 | LDOC1L | LEF1 | LEP | LEPROT | LFNG | LGALS3 | LGALS3BP | | LGALS8 | LGALS9 |
| LGALS9B | LGMN | LGSN | LHFPL2 | LIAS | LIG4 | LILRA1 | LILRA3 | LILRA6 | LILRB1 | LIMA1 |
| LIMK2 | LIMS1 | LIN7C | LLPH | LMF2 | LMNB1 | LMNB2 | LMTK3 | LOC100124692 | | |
| LOC100127893 | | LOC100127894 | | LOC100127922 | | LOC100127975 | | LOC100127993 | | |
| LOC100128060 | | LOC100128062 | | LOC100128252 | | LOC100128269 | | LOC100128274 | | |
| LOC100128291 | | LOC100128410 | | LOC100128460 | | LOC100128485 | | LOC100128498 | | |
| LOC100128516 | | LOC100128525 | | LOC100128533 | | LOC100128548 | | LOC100128627 | | |
| LOC100128729 | | LOC100128731 | | LOC100128908 | | LOC100128994 | | LOC100129055 | | |
| LOC100129067 | | LOC100129094 | | LOC100129139 | | LOC100129201 | | LOC100129243 | | |
| LOC100129267 | | LOC100129424 | | LOC100129426 | | LOC100129441 | | LOC100129445 | | |
| LOC100129466 | | LOC100129502 | | LOC100129543 | | LOC100129608 | | LOC100129637 | | |
| LOC100129645 | | LOC100129681 | | LOC100129686 | | LOC100129934 | | LOC100129952 | | |
| LOC100129960 | | LOC100129982 | | LOC100130000 | | LOC100130053 | | LOC100130070 | | |
| LOC100130154 | | LOC100130171 | | LOC100130255 | | LOC100130276 | | LOC100130289 | | |
| LOC100130332 | | LOC100130520 | | LOC100130550 | | LOC100130561 | | LOC100130562 | | |
| LOC100130598 | | LOC100130624 | | LOC100130707 | | LOC100130715 | | LOC100130764 | | |
| LOC100130769 | | LOC100130892 | | LOC100130932 | | LOC100130980 | | LOC100131076 | | |
| LOC100131096 | | LOC100131253 | | LOC100131349 | | LOC100131452 | | LOC100131526 | | |
| LOC100131572 | | LOC100131662 | | LOC100131672 | | LOC100131675 | | LOC100131713 | | |
| LOC100131718 | | LOC100131810 | | LOC100131835 | | LOC100131850 | | LOC100131866 | | |
| LOC100131989 | | LOC100132037 | | LOC100132086 | | LOC100132199 | | LOC100132288 | | |
| LOC100132323 | | LOC100132395 | | LOC100132425 | | LOC100132444 | | LOC100132493 | | |
| LOC100132499 | | LOC100132510 | | LOC100132521 | | LOC100132526 | | LOC100132547 | | |
| LOC100132652 | | LOC100132707 | | LOC100132717 | | LOC100132724 | | LOC100132728 | | |
| LOC100132742 | | LOC100132761 | | LOC100132797 | | LOC100132804 | | LOC100132888 | | |
| LOC100132901 | | LOC100132920 | | LOC100133034 | | LOC100133077 | | LOC100133080 | | |
| LOC100133129 | | LOC100133163 | | LOC100133177 | | LOC100133220 | | LOC100133298 | | |
| LOC100133329 | | LOC100133398 | | LOC100133692 | | LOC100133697 | | LOC100133760 | | |
| LOC100133770 | | LOC100133803 | | LOC100133875 | | LOC100134053 | | LOC100134159 | | |
| LOC100134172 | | LOC100134241 | | LOC100134291 | | LOC100134537 | | LOC100134624 | | |
| LOC100134688 | | LOC100134868 | | LOC100170939 | | LOC123688 | | LOC127295 | | LOC130773 |
| LOC146053 | | LOC147727 | | LOC147804 | | LOC163233 | | LOC196752 | | LOC197135 |
| LOC202134 | | LOC202227 | | LOC253039 | | LOC255809 | | LOC25845 | | LOC283267 |
| LOC283412 | | LOC283874 | | LOC283953 | | LOC284672 | | LOC286016 | | LOC286444 |
| LOC338799 | | LOC339192 | | LOC339352 | | LOC339799 | | LOC339843 | | LOC345041 |
| LOC345645 | | LOC347292 | | LOC374443 | | LOC387791 | | LOC387820 | | LOC387841 |
| LOC387934 | | LOC388122 | | LOC388339 | | LOC388556 | | LOC388564 | | LOC388955 |
| LOC389053 | | LOC389168 | | LOC389286 | | LOC389322 | | LOC389342 | | LOC389386 |
| LOC389404 | | LOC389765 | | LOC389816 | | LOC390183 | | LOC390345 | | LOC390414 |
| LOC390530 | | LOC390578 | | LOC390735 | | LOC390876 | | LOC391045 | | LOC391169 |
| LOC391334 | | LOC391655 | | LOC391670 | | LOC391769 | | LOC391825 | | LOC391833 |
| LOC392288 | | LOC392501 | | LOC399881 | | LOC399988 | | LOC400061 | | LOC400389 |
| LOC400446 | | LOC400455 | | LOC400464 | | LOC400652 | | LOC400750 | | LOC400759 |
| LOC400836 | | LOC400948 | | LOC400963 | | LOC401076 | | LOC401252 | | LOC401537 |
| LOC401623 | | LOC401717 | | LOC401817 | | LOC401845 | | LOC402057 | | LOC402112 |
| LOC402221 | | LOC402562 | | LOC402677 | | LOC402694 | | LOC439949 | | LOC439992 |
| LOC440055 | | LOC440093 | | LOC440157 | | LOC440280 | | LOC440396 | | LOC440525 |
| LOC440563 | | LOC440595 | | LOC440737 | | LOC440776 | | LOC440926 | | LOC440927 |
| LOC441013 | | LOC441032 | | LOC441154 | | LOC441155 | | LOC441246 | | LOC441642 |
| LOC441907 | | LOC441956 | | LOC442064 | | LOC442153 | | LOC442181 | | LOC442232 |
| LOC442270 | | LOC442319 | | LOC442517 | | LOC442582 | | LOC552889 | | LOC641727 |

TABLE 16-continued

| Gene Listing of Unique Differentially Expressed (DE) Genes | | | | | | | | | | |
|---|---|---|---|---|---|---|---|---|---|---|
| LOC641746 | | LOC641848 | | LOC641849 | | LOC641989 | | LOC641992 | | LOC642017 |
| LOC642031 | | LOC642033 | | LOC642035 | | LOC642073 | | LOC642076 | | LOC642083 |
| LOC642118 | | LOC642120 | | LOC642178 | | LOC642222 | | LOC642236 | | LOC642250 |
| LOC642299 | | LOC642357 | | LOC642393 | | LOC642443 | | LOC642458 | | LOC642502 |
| LOC642567 | | LOC642585 | | LOC642738 | | LOC642741 | | LOC642755 | | LOC642909 |
| LOC642954 | | LOC642974 | | LOC643007 | | LOC643015 | | LOC643031 | | LOC643187 |
| LOC643272 | | LOC643384 | | LOC643387 | | LOC643424 | | LOC643433 | | LOC643531 |
| LOC643534 | | LOC643550 | | LOC643668 | | LOC643680 | | LOC643779 | | LOC643870 |
| LOC643882 | | LOC643896 | | LOC643960 | | LOC643980 | | LOC643997 | | LOC644029 |
| LOC644037 | | LOC644063 | | LOC644094 | | LOC644101 | | LOC644131 | | LOC644315 |
| LOC644330 | | LOC644380 | | LOC644464 | | LOC644482 | | LOC644496 | | LOC644577 |
| LOC644642 | | LOC644655 | | LOC644745 | | LOC644774 | | LOC644799 | | LOC644852 |
| LOC644877 | | LOC644931 | | LOC644964 | | LOC645018 | | LOC645052 | | LOC645086 |
| LOC645173 | | LOC645233 | | LOC645236 | | LOC645251 | | LOC645351 | | LOC645452 |
| LOC645489 | | LOC645515 | | LOC645630 | | LOC645691 | | LOC645693 | | LOC645715 |
| LOC645737 | | LOC645762 | | LOC645944 | | LOC645968 | | LOC646034 | | LOC646044 |
| LOC646197 | | LOC646294 | | LOC646491 | | LOC646527 | | LOC646531 | | LOC646630 |
| LOC646672 | | LOC646688 | | LOC646766 | | LOC646784 | | LOC646785 | | LOC646808 |
| LOC646821 | | LOC646836 | | LOC646841 | | LOC646897 | | LOC646900 | | LOC646909 |
| LOC646942 | | LOC646949 | | LOC646956 | | LOC646966 | | LOC646996 | | LOC647030 |
| LOC647037 | | LOC647074 | | LOC647086 | | LOC647195 | | LOC647276 | | LOC647460 |
| LOC647654 | | LOC647908 | | LOC648059 | | LOC648283 | | LOC648343 | | LOC648509 |
| LOC648526 | | LOC648638 | | LOC648705 | | LOC648733 | | LOC648740 | | LOC648749 |
| LOC648822 | | LOC648863 | | LOC648907 | | LOC648921 | | LOC648980 | | LOC648984 |
| LOC649088 | | LOC649150 | | LOC649209 | | LOC649214 | | LOC649260 | | LOC649330 |
| LOC649447 | | LOC649456 | | LOC649801 | | LOC649821 | | LOC649839 | | LOC649873 |
| LOC650321 | | LOC650638 | | LOC650737 | | LOC650898 | | LOC651064 | | LOC651198 |
| LOC651316 | | LOC651738 | | LOC651816 | | LOC651919 | | LOC652113 | | LOC652274 |
| LOC652750 | | LOC652755 | | LOC652837 | | LOC653056 | | LOC653080 | | LOC653086 |
| LOC653105 | | LOC653115 | | LOC653157 | | LOC653162 | | LOC653316 | | LOC653324 |
| LOC653375 | | LOC653450 | | LOC653486 | | LOC653489 | | LOC653496 | | LOC653559 |
| LOC653596 | | LOC653737 | | LOC653829 | | LOC653884 | | LOC653888 | | LOC653994 |
| LOC654074 | | LOC654096 | | LOC654121 | | LOC654346 | | LOC654350 | | LOC727762 |
| LOC727821 | | LOC727848 | | LOC727962 | | LOC727970 | | LOC728002 | | LOC728026 |
| LOC728031 | | LOC728060 | | LOC728093 | | LOC728105 | | LOC728115 | | LOC728128 |
| LOC728170 | | LOC728179 | | LOC728207 | | LOC728310 | | LOC728416 | | LOC728428 |
| LOC728457 | | LOC728499 | | LOC728519 | | LOC728576 | | LOC728602 | | LOC728608 |
| LOC728650 | | LOC728661 | | LOC728666 | | LOC728715 | | LOC728744 | | LOC728748 |
| LOC728755 | | LOC728820 | | LOC728908 | | LOC728953 | | LOC728973 | | LOC729143 |
| LOC729196 | | LOC729200 | | LOC729236 | | LOC729255 | | LOC729279 | | LOC729342 |
| LOC729366 | | LOC729369 | | LOC729397 | | LOC729402 | | LOC729409 | | LOC729423 |
| LOC729505 | | LOC729510 | | LOC729513 | | LOC729519 | | LOC729645 | | LOC729652 |
| LOC729677 | | LOC729679 | | LOC729683 | | LOC729686 | | LOC729687 | | LOC729692 |
| LOC729739 | | LOC729760 | | LOC729764 | | LOC729779 | | LOC729789 | | LOC729798 |
| LOC729806 | | LOC729843 | | LOC729898 | | LOC729985 | | LOC730029 | | LOC730052 |
| LOC730060 | | LOC730187 | | LOC730202 | | LOC730246 | | LOC730281 | | LOC730316 |
| LOC730324 | | LOC730382 | | LOC730432 | | LOC730534 | | LOC730746 | | LOC730924 |
| LOC730990 | | LOC730993 | | LOC731096 | | LOC731308 | | LOC731314 | | LOC731365 |
| LOC731751 | | LOC731789 | | LOC732229 | | LOC732360 | | LOC92017 | | LOC92249 |
| LOC92755 | | LPAR5 | LPHN1 | LPIN2 | LRBA | LRFN3 | LRIG1 | LRPAP1 | LRRC14 | LRRC16A |
| LRRC26 | LRRC40 | LRRK2 | LSM5 | LSP1 | LTB4R | LUZP1 | LYAR | LYPLA1 | LYRM4 | LYRM7 |

TABLE 16-continued

Gene Listing of Unique Differentially Expressed (DE) Genes

| | | | | | | | | | | |
|---|---|---|---|---|---|---|---|---|---|---|
| LYSMD3 | MAD2L1 | MAD2L1BP | | MAEA | MAF | MAFF | MAGED4B | | MAGEE1 | Magmas |
| MAL | MAML3 | MAN1C1 | MAP1LC3A | | MAP2K4 | MAP3K7IP1 | | MAP3K8 | MAPBPIP | MAPK8IP3 |
| MAPKAPK2 | | MAPRE3 | MARCKSL1 | | MARS2 | MAST3 | MAZ | MBD2 | MBD3 | MBOAT2 |
| MBP | MBTPS1 | MCART1 | MCHR2 | MCM3APAS | | MCTP1 | MCTP2 | MCTS1 | MDC1 | MDH2 |
| ME2 | MED21 | MED24 | MED31 | MEF2A | MEF2C | MEF2D | MEGF6 | MEIS1 | METAP1 | METTL9 |
| MFNG | MGAT3 | MGAT4A | MGC10997 | | MGC12760 | | MGC13005 | | MGC21881 | |
| MGC26356 | | MGC3020 | MGC40489 | | MGC42367 | | MGC4677 | MGC52498 | | MGC87895 |
| MID1IP1 | MIER2 | MIIP | MIR1299 | MIR142 | MIR1974 | MIR2116 | MIR574 | MIR877 | MIR98 | MIS12 |
| MLEC | MLKL | MLL5 | MMGT1 | MMP28 | MNT | MOAP1 | MOBKL2C | | MORC2 | MPDU1 |
| MPHOSPH10 | | MPL | MPP6 | MRI1 | MRP63 | MRPL17 | MRPL3 | MRPL40 | MRPL41 | MRPL43 |
| MRPL44 | MRPL45 | MRPL47 | MRPL55 | MRPS10 | MRPS15 | MRPS25 | MRPS27 | MRPS34 | MRRF | MS4A1 |
| MS4A14 | MS4A2 | MS4A3 | MS4A4A | MS4A7 | MSH2 | MSL3 | MSRB3 | MSX2P1 | MTCP1 | MTF2 |
| MTHFD2 | MTMR14 | MTMR3 | MTUS1 | MTX1 | MTX3 | MUM1 | MUT | MVP | MXI1 | MYB |
| MYCBP2 | MYH9 | MYO9B | MYOM1 | MYST3 | N4BP2 | N4BP2L1 | NAALADL1 | | NACAP1 | NAGLU |
| NAGPA | NAIP | NAP1L1 | NAT6 | NAT8B | NBEA | NBL1 | NBN | NBPF14 | NCALD | NCBP2 |
| NCF1B | NCF4 | NCKAP1L | | NCOA5 | NCOR2 | NCR3 | NCRNA00081 | | NCRNA00085 | |
| NCRNA00092 | | NCRNA00152 | | NDE1 | NDFIP1 | NDRG3 | NDUFA4 | NDUFA5 | NDUFAF3 | |
| NDUFB11 | NDUFC1 | NDUFS1 | NEIL2 | NELL2 | NENF | NFATC2IP | | NFIC | NFIX | NFKBIA |
| NFKBIB | NFKBIL2 | NFX1 | NFYB | NHLRC4 | NHP2 | NIP7 | NIPSNAP3A | | NLRC5 | NLRP1 |
| NLRP12 | NLRP7 | NLRP8 | NLRX1 | NME2 | NMI | NMT2 | NNT | NOG | NOL9 | |
| NOTCH2NL | | NOX4 | NPAL3 | NPAT | NR1D2 | NR3C1 | NR3C2 | NR4A2 | NT5C | NT5C3L |
| NT5DC1 | NT5DC3 | NTNG2 | NUAK2 | NUBPL | NUCB2 | NUCKS1 | NUDCD2 | NUDT16L1 | | NUDT2 |
| NUDT21 | NUFIP2 | NUMA1 | OAF | OAS1 | OAS3 | OASL | ODC1 | OGFOD1 | OLA1 | OMA1 |
| OPN1SW | OR1J1 | OR2A42 | OR7E156P | | ORC5L | OSBPL1A | OSBPL8 | OSTCL | OTOF | OTUD1 |
| P2RX5 | P2RY8 | P4HB | P704P | P76 | PA2G4 | PABPC1 | PABPC4 | PACS1 | PAFAH2 | PAK1IP1 |
| PAK2 | PALLD | PAN3 | PAPD5 | PAPSS1 | PAPSS2 | PAQR4 | PAQR8 | PARM1 | PARP10 | PARP14 |
| PARP15 | PARP8 | PARP9 | PATE2 | PATL2 | PCBP2 | PCDHB9 | PCDHGB6 | | PCYOX1 | PDCD10 |
| PDCD2 | PDCL | PDE12 | PDE5A | PDE7A | PDF | PDIA3P | PDK1 | PDPK1 | PDZD4 | PEBP1 |
| PECI | PELI2 | PELP1 | PEMT | PEX11B | PEX14 | PFKFB3 | PFKL | PFN2 | PFTK1 | PGAM1 |
| PGAM4 | PGGT1B | PGLS | PGM2 | PGM2L1 | PHACTR2 | PHAX | PHB | PHC2 | PHC3 | PHF11 |
| PHF14 | PHF2 | PHF20L1 | PHKB | PHLDB3 | PI4K2B | PIAS2 | PID1 | PIGT | PIGX | PIK3AP1 |
| PIK3CD | PIK3CG | PIK3IP1 | PIK3R1 | PIM2 | PIM3 | PIN1 | PION | PIP3-E | PIP4K2A | PIP5K1C |
| PIP5K2A | PITPNC1 | PJA2 | PKIA | PKM2 | PKN1 | PKN2 | PLA2G2D | PLAA | PLAG1 | PLAGL1 |
| PLAUR | PLCB2 | PLCG1 | PLCXD1 | PLD3 | PLD6 | PLEKHA1 | PLEKHA5 | PLEKHB1 | PLEKHB2 | PLEKHF1 |
| PLIN2 | PLSCR1 | PLXNA4 | PML | PMM2 | PMS2L1 | PMS2L2 | PMS2L5 | PNKP | PNPLA2 | PNPLA6 |
| PNPT1 | PNRC2 | POGK | POLDIP3 | POLG2 | POLK | POLR1D | POLR1E | POLR2A | POLR2E | POLR2G |
| POLR2J4 | POLR2L | POLR3GL | POM121C | POTE2 | POTEE | PPAPDC2 | PPARBP | PPFIA1 | PPHLN1 | PPIB |
| PPID | PPIG | PPM1B | PPM1K | PPP1CB | PPP1R13B | | PPP1R15B | | PPP1R2 | PPP2R1A |
| PPP2R2B | PPP2R3A | PPP2R5C | PPP2R5D | PPP2R5E | PPP4R2 | PPPDE2 | PPTC7 | PRAGMIN | | PRDM4 |
| PRIM2 | PRKAG1 | PRKCA | PRKCB | PRKCB1 | PRKCH | PRKCQ | PRKY | PRMT2 | PRPF39 | PRPF8 |
| PRR13 | PRR7 | PRRG4 | PRRT3 | PRUNE | PSG3 | PSG9 | PSIP1 | PSMA3 | PSMA6 | PSMB7 |
| PSMB8 | PSMB9 | PSMC4 | PSMC6 | PSRC1 | PTBP1 | PTDSS2 | PTGR2 | PTGS1 | PTK2B | PTMS |
| PTOV1 | PTP4A2 | PTPLAD1 | PTPLAD2 | PTPLB | PTPN1 | PTPN2 | PTPN7 | PTPRC | PTPRE | PTPRO |
| PUM1 | PURA | PVALB | PYCARD | QARS | QRICH1 | RAB11FIP1 | | RAB11FIP4 | | RAB11FIP5 |
| RAB20 | RAB22A | RAB24 | RAB33A | RAB33B | RAB37 | RAB3IP | RAB43 | RABGEF1 | RAD21 | RAD23A |
| RAD23B | RAD51 | RAG1AP1 | RALA | RALGPS2 | RALY | RANBP9 | RANGRF | RAP1B | RAPGEF2 | RAPGEF6 |
| RASA2 | RASD1 | RASSF2 | RASSF5 | RASSF6 | RAVER1 | RAX2 | RAXL1 | RBBP4 | RBBP5 | RBM11 |
| RBM12B | RBM17 | RBM3 | RBM39 | RBM4 | RBMS1 | RC3H2 | RCN2 | REC8 | RFK | RFNG |
| RFX1 | RFX4 | RGL4 | RGMA | RGPD1 | RGS18 | RHBDD2 | RHBDF2 | RHOF | RHOQ | RHOT1 |
| RIOK1 | RIPK3 | RLN2 | RN5S9 | RN7SK | RNASE3 | RNASEH2B | | RNASEN | RNF10 | RNF103 |
| RNF135 | RNF144 | RNF144A | RNF213 | RNF26 | RNMT | RNPEPL1 | RNU12 | RNU4ATAC | | RNU5A |

TABLE 16-continued

Gene Listing of Unique Differentially Expressed (DE) Genes

| | | | | | | | | | | |
|---|---|---|---|---|---|---|---|---|---|---|
| RNU6-1 | RNY3 | ROCK1 | ROCK2 | ROD1 | RPAP2 | RPAP3 | RPL10A | RPL17 | RPL22 | RPL23A |
| RPL23AP13 | | RPL26L1 | RPL29P2 | RPL36 | RPL37 | RPL4 | RPL5 | RPL6 | RPL7L1 | RPL8 |
| RPP40 | RPRD2 | RPS10P3 | RPS14 | RPS15 | RPS18 | RPS29 | RPS3 | RPS4X | RPS5 | RPS6 |
| RPS6KA1 | RPS6KA2 | RPS6KA4 | RPS6P1 | RPS7 | RPS8 | RPUSD1 | RRBP1 | RRP1B | RSAD1 | RSF1 |
| RSL1D1 | RTBDN | RTKN2 | RTP4 | RUFY2 | RUNX1 | RUNX3 | RWDD1 | RXRA | RYBP | S100A10 |
| S100A6 | SAC3D1 | SAMD8 | SAMD9L | SAMSN1 | SAP30L | SBF1 | SBK1 | SCAMP1 | SCARNA16 | |
| SCARNA21 | | SCARNA22 | | SCARNA5 | | SCN3A | SDAD1 | SDHAF1 | SDHC | SDPR |
| SEC13 | SEC16A | SEC23A | SEC24A | SEC62 | SELL | SELM | SELPLG | SELS | SELT | SEMA3E |
| SEMA4D | SEMA4F | SENP6 | SEPN1 | SEPW1 | SERINC1 | SERINC3 | SERPINA1 | | SERPINB8 | |
| SERPINE2 | | SERPING1 | | SERTAD2 | SESN1 | SET | SETD1A | SETD1B | SETD6 | SF1 |
| SF3A1 | SF3A2 | SF3B14 | SF4 | SFRS11 | SFRS12 | SFRS12IP1 | | SFRS2B | SFRS3 | SGK |
| SGK3 | SGOL2 | SH2B2 | SH3BGRL3 | | SH3BP2 | SH3GL1 | SH3GLB2 | SH3KBP1 | SH3PXD2A | |
| SIAH1 | SIDT2 | SIGLEC7 | SIGLECP3 | | SIK3 | SIL1 | SIN3A | SKA2 | SKAP1 | SKP2 |
| SLA2 | SLAMF8 | SLC15A2 | SLC24A3 | SLC25A19 | | SLC25A23 | | SLC25A28 | | SLC25A3 |
| SLC2A14 | SLC2A6 | SLC35C1 | SLC35E1 | SLC36A4 | SLC38A1 | SLC39A11 | | SLC39A8 | SLC44A2 | SLC45A3 |
| SLC4A5 | SLC5A8 | SLC6A10P | | SLC7A1 | SLC7A3 | SLC7A6 | SLC8A3 | SLC9A4 | SMA5 | SMAD3 |
| SMAD5 | SMARCA5 | | SMARCB1 | | SMARCC1 | | SMARCC2 | | SMC5 | SMPD1 |
| SMYD2 | SMYD3 | SNAPC1 | SNHG10 | SNHG8 | SNHG9 | SNORA12 | SNORA28 | SNORD13 | SNORD16 | SNORD18C |
| SNORD21 | SNORD46 | SNORD58B | | SNORD62B | | SNORD71 | SNORD73A | | SNORD76 | SNORD95 |
| SNRPD3 | SNRPE | SNUPN | SNURF | SNX14 | SNX17 | SNX20 | SNX7 | SOCS3 | SOCS4 | SORBS3 |
| SP1 | SP100 | SP2 | SP4 | SPC24 | SPC25 | SPCS1 | SPCS2 | SPG21 | SPI1 | SPIN1 |
| SPNS3 | SPOCK2 | SPTAN1 | SPTLC1 | SREBF1 | SRFBP1 | SRM | SRP19 | SRP72 | SRPK2 | SRRM2 |
| SS18 | SSB | SSBP3 | SSH1 | SSNA1 | SSR4 | ST6GAL1 | ST6GALN | AC4 | ST6GALN | AC6 |
| STAR | STARD7 | STAT1 | STAT4 | STK40 | STRN4 | STX10 | STX7 | SULT1A2 | SULT1A3 | SUMF2 |
| SUMO1 | SUMO1P3 | SURF6 | SUV420H1 | | SVIL | SYAP1 | SYF2 | SYNC1 | SYNE1 | SYTL2 |
| SYTL3 | TACC1 | TADA1L | TAF1C | TAF1D | TAF4 | TAF8 | TAF9 | TAGAP | TAGLN | TAL1 |
| TANK | TAP1 | TARP | TATDN2 | TBC1D10B | | TBC1D22A | | TBC1D7 | TBC1D9B | TBCA |
| TBL1X | TCEA2 | TCEA3 | TCEAL4 | TCEAL8 | TCEB1 | TCEB2 | TCERG1 | TCFL5 | TCL1A | TCL1B |
| TCP1 | TDG | TDRD7 | TECR | TESK1 | TFEC | TFIP11 | TGFBR2 | TGIF1 | THEX1 | THOC2 |
| THOC4 | TIAF1 | TIAL1 | TIFA | TIMELESS | | TIMM10 | TIMM22 | TIMP2 | TLE2 | TLK1 |
| TLN1 | TLR10 | TLR5 | TMC6 | TMCC1 | TMCC3 | TMEM106A | | TMEM107 | | TMEM109 |
| TMEM111 | | TMEM116 | | TMEM126B | | TMEM137 | | TMEM156 | | TMEM165 |
| TMEM185A | | TMEM189-UBE2V1 | | TMEM191A | | TMEM203 | | TMEM204 | | TMEM209 |
| TMEM219 | | TMEM38B | | TMEM50B | | TMEM51 | TMF1 | TMSB4X | TMTC4 | TMUB1 |
| TMX4 | TNFAIP6 | TNFAIP8L1 | | TNFRSF21 | | TNFRSF25 | | TNFRSF9 | TNFSF10 | TNFSF12 |
| TNFSF13 | TNFSF13B | | TNFSF14 | TNFSF15 | TNIK | TNS1 | TOB1 | TOMM20 | TOMM7 | TOP1MT |
| TOP1P1 | TOP1P2 | TOP2B | TOX | TOX2 | TP53BP2 | TP53INP2 | TPI1 | TPM4 | TPP2 | TPRKB |
| TRA1P2 | TRAPPC4 | TRAPPC9 | TRAT1 | TRIM13 | TRIM16L | TRIM22 | TRIM23 | TRIM26 | TRIM4 | TRIM5 |
| TRIM52 | TRIM78P | TRIM9 | TRIOBP | TROVE2 | TRPC4AP | TRRAP | TSC22D1 | TSC22D3 | TSEN15 | TSEN54 |
| TSGA14 | TSHZ1 | TSPAN14 | TSPAN5 | TSTD1 | TTC3 | TTC4 | TTN | TTRAP | TUBA1A | TUBA3E |
| TUBB4Q | TUFM | TULP4 | TUT1 | TWSG1 | TYMP | TYSND1 | U2AF1 | UBA3 | UBAP2L | UBE1C |
| UBE2D1 | UBE2D2 | UBE2E3 | UBE2H | UBE2J1 | UBE2L6 | UBE2O | UBE2V1 | UBE2W | UBE3B | UBE4B |
| UBN2 | UBXN7 | UCRC | UGCGL1 | UGP2 | UHMK1 | UHRF2 | UIMC1 | UNC84B | UNC93B1 | UNKL |
| UPF3A | UQCRH | URG4 | USH1G | USP10 | USP13 | USP14 | USP18 | USP33 | USP47 | USP48 |
| USP5 | USP53 | USP6 | USP9X | UXT | VAC14 | VAMP2 | VAV3 | VDAC2 | VEGFB | VEZT |
| VHL | VPS13B | VPS13C | VPS28 | VPS41 | VPS52 | VSIG1 | VWF | WAS | WASH2P | WBP11 |
| WBP2 | WDFY3 | WDR1 | WDR23 | WDR48 | WDR73 | WDR74 | WDR75 | WDR82 | WHAMM | WNK1 |
| WRB | WRNIP1 | WWP1 | WWP2 | XAB2 | XAF1 | XRCC4 | XRCC6 | XRN1 | XRN2 | XYLT2 |
| YES1 | YIF1A | YIPF4 | YOD1 | YPEL3 | YTHDC1 | YY1 | ZBED4 | ZBTB16 | ZBTB3 | ZBTB4 |
| ZBTB42 | ZBTB43 | ZBTB9 | ZC3H4 | ZC3H5 | ZCCHC10 | ZCCHC14 | ZDHHC4 | ZDHHC9 | ZFAND1 | ZFHX3 |
| ZFP14 | ZFP30 | ZFP37 | ZFP91 | ZFPM1 | ZFYVE19 | ZFYVE27 | ZMYND11 | | ZNF12 | ZNF121 |

TABLE 16-continued

| Gene Listing of Unique Differentially Expressed (DE) Genes | | | | | | | | | | |
|---|---|---|---|---|---|---|---|---|---|---|
| ZNF131 | ZNF136 | ZNF142 | ZNF148 | ZNF185 | ZNF204 | ZNF223 | ZNF234 | ZNF24 | ZNF252 | ZNF256 |
| ZNF260 | ZNF274 | ZNF281 | ZNF282 | ZNF319 | ZNF32 | ZNF320 | ZNF329 | ZNF337 | ZNF33A | ZNF345 |
| ZNF364 | ZNF37A | ZNF395 | ZNF420 | ZNF430 | ZNF438 | ZNF441 | ZNF444 | ZNF471 | ZNF502 | ZNF518B |
| ZNF524 | ZNF526 | ZNF529 | ZNF540 | ZNF544 | ZNF559 | ZNF562 | ZNF567 | ZNF580 | ZNF589 | ZNF609 |
| ZNF615 | ZNF626 | ZNF638 | ZNF641 | ZNF644 | ZNF669 | ZNF683 | ZNF716 | ZNF738 | ZNF773 | ZNF792 |
| ZNF805 | ZNF818 | ZNF828 | ZNF831 | ZNF860 | ZNF91 | ZNF92 | ZNF93 | ZRSR2 | ZSCAN2 | ZYG11B |
| CREB1 | CLOCK | ZNF398 | ATXN7L3B | | MTRNR2L1 | | ZBED3 | PPM1A | ZNF160 | RORA |
| FBXO22 | TRDV3 | CCNG2 | DDI2 | TTC39C | ETS1 | ZMAT3 | LRRC8B | ZNF33B | TMEM33 | GDF11 |
| TNRC6C | RAB27B | | | | | | | | | |

TABLE 17

| Gene Listing of Commonly Dysregulated Genes in Discovery and Replication Toddlers | | | | | | | | | |
|---|---|---|---|---|---|---|---|---|---|
| ABCG1 | ACACB | AGER | AGPAT3 | AKR1C3 | AKR1D1 | AKT1 | ALG10B | ANKRD22 | ANKRD44 |
| ANXA1 | ANXA3 | AP2A1 | ARAP3 | ARHGAP10 | ARHGAP25 | ARHGAP30 | ARHGAP9 | ARL5A | ASCC3 |
| ASMTL | ATG2A | ATG4C | ATP1B1 | ATP5A1 | AXIN1 | BIRC3 | BMF | BPGM | BRDG1 |
| C10orf4 | C11orf82 | C14orf102 | C16orf53 | C19orf59 | C1GALT1 | C1GALT1C1 | C1QBP | C20orf30 | C3orf17 |
| C3orf38 | C3orf58 | C4orf16 | C4orf32 | C4orf34 | C6orf150 | C7orf28A | C9orf127 | C9orf72 | C9orf85 |
| CABC1 | CABIN1 | CAMK1D | CAPZA1 | CARD17 | CBFB | CBX7 | CCDC117 | CCDC50 | CCDC90B |
| CCDC91 | CCNY | CCNYL1 | CCS | CCT6P1 | CD274 | CD300LB | CD3E | CD84 | CD97 |
| CDAN1 | CDC2L6 | CDK2AP2 | CDK5RAP3 | CENPV | CEPT1 | CERK | CHES1 | CHM | CHMP5 |
| CHORDC1 | CHPF2 | CKS2 | CLEC4D | CLIC4 | CNIH4 | COMMD8 | COPS2 | CPNE1 | CRY2 |
| CSNK1E | CTDP1 | CTDSP1 | CTSF | CXorf57 | CYP20A1 | DAPK2 | DBI | DBP | DCK |
| DCTN6 | DDIT4 | DDX60 | DHPS | DHRS3 | DHX34 | DLEU1 | DNAJB14 | DNHD2 | DPEP2 |
| DPM3 | DRD4 | DTWD1 | DUSP22 | DYNLT3 | ECT2 | EEF2K | EIF3G | ENO2 | ENO3 |
| EPN2 | EPSTI1 | ETNK1 | FABP5 | FAM134A | FAM134B | FAM153B | FAM91A2 | FANCL | FBXO5 |
| FEZ1 | FHL3 | FICD | FKTN | FLJ39639 | FOXJ2 | FYN | FYTTD1 | GALT | GATAD2B |
| GATS | GBP1 | GCH1 | GNAI2 | GNPDA2 | GOLPH3L | GPR141 | GPR68 | GPR84 | GRASP |
| GSTM1 | GSTM2 | GTF3C6 | GTPBP8 | HCCS | HERC2 | HHEX | HIBCH | HINT3 | HK1 |
| HNRPK | HPCAL4 | HRSP12 | HSPA9 | IFI16 | IFI27 | IGF2BP3 | IL6ST | IMPA2 | INADL |
| IP6K1 | IQCB1 | ITFG1 | ITGAX | ITPKB | KCNG1 | KDM6B | KHNYN | KIAA0247 | KIAA1279 |
| KIAA1715 | KIF2A | KLHL20 | KPNA2 | KPNA6 | LACTB | LDHA | LFNG | LGALS3BP | LGALS8 |
| LMF2 | LMTK3 | LOC202134 | LOC387934 | LOC389816 | LOC442582 | LOC643272 | LOC648733 | LOC650898 | LOC652837 |
| LOC653105 | LOC654121 | LOC729843 | LPIN2 | LRRC26 | LYPLA1 | MAD2L1 | MAD2L1BP | MAP1LC3A | MAPRE3 |
| MAST3 | ME2 | METAP1 | MGAT3 | MGC12760 | MGC13005 | MGC3020 | MGC40489 | MID1IP1 | MLKL |
| MRPL3 | MRPL47 | MRPS10 | MS4A1 | MS4A2 | MS4A4A | MSH2 | MTHFD2 | MUT | MYH9 |
| MYO9B | MYOM1 | Magmas | N4BP2L1 | NAALADL1 | NAGLU | NAT6 | NBN | NCBP2 | NCOR2 |
| NCR3 | NDE1 | NDRG3 | NFATC2IP | NFIC | NFKBIB | NLRP1 | NNT | NR3C2 | NUCB2 |
| NUDT16L1 | OMA1 | OTOF | PACS1 | PAFAH2 | PARP9 | PCYOX1 | PDCD10 | PDZD4 | PFTK1 |
| PGGT1B | PHAX | PHC3 | PHF14 | PHF2 | PHKB | PI4K2B | PIAS2 | PIGX | PIK3CD |
| PITPNC1 | PKIA | PLCB2 | PLD3 | PLEKHF1 | PLSCR1 | PML | PNPLA2 | PNRC2 | POLR1E |
| PPM1K | PPPDE2 | PSMA3 | PSMA6 | PSMC6 | PTDSS2 | PTMS | PTP4A2 | PTPLAD1 | PTPN2 |
| PTPRE | PTPRO | RAB37 | RAD23B | RAD51 | RALY | RASSF2 | RBM3 | RFNG | RFX4 |
| RGPD1 | RHBDD2 | RHOT1 | RIOK1 | RN7SK | RPAP3 | RPL6 | RPP40 | RPS6KA2 | RPS7 |
| RTP4 | SAMD9L | SAMSN1 | SDHAF1 | SELL | SELM | SEMA4D | SERPINB8 | SF1 | SFRS12IP1 |
| SFRS3 | SGOL2 | SH3GL1 | SIGLEC7 | SIGLECP3 | SLC35E1 | SLC39A8 | SLC44A2 | SLC45A3 | SMARCA5 |
| SMARCC2 | SNX14 | SOCS4 | SORBS3 | SP100 | SPC25 | SPNS3 | SPTLC1 | SREBF1 | SRFBP1 |
| SRP72 | SS18 | SSB | SSBP3 | STAT1 | STRN4 | SUMO1P3 | SYTL3 | TADA1L | TANK |
| TBC1D9B | TBCA | TBL1X | TCEB2 | TDG | THEX1 | THOC2 | TIFA | TLR10 | TMEM126B |
| TMEM165 | TMTC4 | TNFRSF21 | TNFSF12 | TNFSF14 | TP53INP2 | TPRKB | TRIM22 | TRIM78P | TRPC4AP |
| TSC22D1 | TSC22D3 | TSEN54 | TSGA14 | TSPAN14 | UBA3 | UBE4B | UGP2 | UNKL | VAMP2 |
| VEZT | VPS13B | VPS28 | VPS41 | WDR73 | WNK1 | WRB | XYLT2 | YES1 | YPEL3 |
| YY1 | ZBTB16 | ZBTB4 | ZFPM1 | ZFYVE27 | ZNF24 | ZNF345 | ZNF395 | ZNF430 | ZNF518B |
| ZNF526 | ZNF567 | ZNF589 | ZNF626 | ZNF92 | | | | | |

TABLE 18

| Gene Listing of DNA-Damage Genes |
|---|
| 14-3-3 ATM Bax Bcl-2 ICAD CBP CDK1 (p34) CREB1 DNA ligase IV FasR(CD95) |
| G-protein alpha-s HSP90 I-kB PHAP1 (pp32) MRE11 PCNA AKT(PKB) PLC-beta |
| PP2A catalytic RPA3 RAD23A Rad51 Rb protein p90Rsk STAT1 SOS PDK(PDPK1) |
| XRCC4 Adenylate cyclase Beta- catenin c-Abl Calmodulin Caspase-7 Caspase-8 Cyclin D |
| Nibrin ERK1/2 ATR Ubiquitin PI3K cat class IA PI3K reg class IA |
| MEK4(MAP2K4) C-IAP2 c-IAP1 HSP27 PKC-alpha PKA-cat (cAMP- dependent)p300 Histone H1 |
| Caspase-2 POLR2A Cyclin A HSP70 SUMO-1 Lamin B MKK7 (MAP2K7) PML NCOA1 (SRC1) |
| SP1 MSH2 TDG GLK(MAP4K3) PLK3 (CNK) FHL2 Ku70 SET WRN |
| PP2C Bim BMF MAP1 RAP-1A Caspase-4 EGR1 CDC25B NURR1 POLD cat (p125) |
| Chk1 Keratin 1 NAIP Beta- arrestin2 14-3-3 theta Artemis BFL1 Centrin-2 Chk2 |
| ERCC-1 ERCC8 FANCL HMG2 Histone H2B La protein Lamin B1 MSH3 MUNC13-4 |
| MutSbeta complex N- myristoyltransferase NFBD1 NUMA1 PIAS2 PNKP POLD reg (p12) |
| PTOP RAD23B RBBP8 (CtIP) RPL22 Rab-27A Sirtuin USP1 VDAC2 XAB2 cPKC |
| (conventional) hnRNP A1 hnRNP C p23 co-chaperone |

TABLE 19

| Gene Listing of Mitogenic Signaling Genes |
|---|
| Bax Bcl-2 ERK5 (MAPK7) C3G CBP CDK1 (p34) CREB1 CRK c-Cbl CDC42 |
| ErbB2 FasR(CD95) Fyn G-protein alpha-i family G-protein alpha-s RASA2 |
| HSP90 I-kB JAK2 LIMK2 Lck NF-AT4(NFATC3) PAK2 PCNA |
| AKT(PKB) PKC-zeta PKR PLC-beta PLC-gamma Pim-1 Pyk2(FAK2) |
| Rb protein p90Rsk STAT1 SOS Tyk2 PDK(PDPK1) VEGF-B Adenylate cyclase |
| Beta-catenin Calmodulin Caspase-7 Cyclin D gp130 ERK1/2 SKP2 Paxillin |
| PKC Ubiquitin PI3K cat class IA PI3K reg class IA RPS6 MEK4(MAP2K4) C-IAP2 |
| c-IAP1 MAPKAPK2 HSP27 PKC-beta PKC-alpha ILK PKA-cat (cAMP-dependent) |

TABLE 19-continued

| Gene Listing of Mitogenic Signaling Genes | | | | | | | | | | |
|---|---|---|---|---|---|---|---|---|---|---|
| | FOX03A | RalA | p300 | MRLC | COX-1 (PTGS1) | | GMF | DCOR | Cyclin A2 | PKC-theta |
| | IRS-2 | SH2B | MKK7 (MAP2K7) | | NCK1 | N-Ras | NCOA1 (SRC1) | | SP1 | IBP |
| | DOK2 | TPL2(MAP3K8) | | GLK(MAP4K3) | | RASA3 | Sequestosome 1(p62) | | ICAM1 | Bax |
| | Bcl-2 | ERK5 (MAPK7) | | C3G | CBP | CDK1 (p34) | | CREB1 | CRK | c-Cbl |
| | CDC42 | ErbB2 | FasR(CD95) | | Fyn | G-protein alpha-i family | | | G-protein | alpha-s |
| | RASA2 | HSP90 | I-kB | JAK2 | LIMK2 | Lck | NF-AT4(NFATC3) | | PAK2 | PCNA |
| | AKT(PKB) | | PKC-zeta | PKR | PLC-beta | PLC-gamma | | Pim-1 | Pyk2(FAK2) | |
| | Rb protein p90Rsk | | STAT1 | SOS | Tyk2 | PDK(PDPK1) | | VEGF-B | Adenylate | cyclase |
| | Beta-catenin | | Calmodulin | | Caspase-7 | Cyclin D | gp130 | ERK1/2 | SKP2 | Paxillin |
| | PKC | Ubiquitin | PI3K cat class IA | | PI3K reg class IA | | RPS6 | MEK4(MAP2K4) | | C-IAP2 |
| | c-IAP1 | MAPKAPK2 | | HSP27 | PKC-beta | PKC-alphaILK | | PKA-cat | (cAMP-dependent) | |
| | FOXO3A | RalA | p300 | MRLC | COX-1 (PTGS1) | | GMF | DCOR | Cyclin A2 | PKC-theta |
| | IRS-2 | SH2B | MKK7 (MAP2K7) | | NCK1 | N-Ras | NCOA1 (SRC1) | | SP1 | IBP |
| | DOK2 | TPL2(MAP3K8) | | GLK(MAP4K3) | | RASA3 | Sequestosome 1(p62) | | ICAM1 | BCR |
| | PLAUR (uPAR) | | RAP-1A | PDZ-GEF1 | | MAGI-1(BAIAP1) | | Tuberin | EGR1 | NFKBIA |
| | CDC25B | SOCS3 | MEF2C | PLGF | ERK1 (MAPK3) | | Angiopoietin 1 | | PLC-gamma 1 | |
| | p90RSK1 | LPP3 | PI3K reg class IA (p85-alpha) | | | Neutral sphingomyelinase | | | DIA1 | 14-3-3 |
| zeta/delta | Acid sphingomyelinase | | | BFL1 | BUB1 | CCL2 | CERK1 | GIPC | GLCM | MLCP |
| (cat) | NCOA3 (pCIP/SRC3)PAQR7 | | | PAQR8 | PDGF-D | PEDF-R (iPLA2-zeta) | | PELP1 | PI3K cat class IA | |
| (p110-delta) | | PI3K reg class IA (p85) | | | PKA-cat alpha | | RGL2 | RNTRE | ROCK1 | ROCK2 |
| | SPT1 | TSAD | Tcf(Lef) | Tob1 | WNK1 | | | | | |

TABLE 20

| Top 30 Genes with the Highest Gene Connectivity Correlated with Brain Size Variation in ASD | | | | | | | | |
|---|---|---|---|---|---|---|---|---|
| Module greenyellow | | | | | | | | |
| DLGAP5 | HMMR | CEP55 | CDKN3 | CCNB2 | ASPM | KIF11 | KIAA0101 | OIP5 |
| TOP2A | BUB1 | NUSAP1 | TYMS | NCAPG | CDC45L | CCNA2 | MCM10 | CHEK1 |
| UBE2C | AURKA | CDC2 | CENPE | PTTG3P | PRC1 | CDCA5 | MELK | UHRF1 |
| MND1 | ZWINT | GMNN | | | | | | |
| Module grey60 | | | | | | | | |
| TXNDC5 | TNFRSF17 | ABCB9 | MGC29506 | CD38 | FKBP11 | SEC11C | LOC647450 | LOC647506 |
| LOC652493 | LOC652694 | CRKRS | IGJ | CAMK1G | GGH | CAV1 | GLDC | DNAJB11 |
| ELL2 | FAM46C | IGLL1 | ARMET | LOC642113 | ITM2C | HSP90B1 | LOC642131 | SLC25A4 |
| LOC651751 | LOC390712 | SDF2L1 | | | | | | |
| Module midnightblue | | | | | | | | |
| SH3BGRL2 | CTDSPL | GP9 | PDE5A | TUBB1 | ITGB5 | ESAM | SEPT5 | TREML1 |
| PTGS1 | TSPAN9 | CTTN | NRGN | PTCRA | SELP | ITGA2B | MARCH2 | MYLK |
| SDPR | ALOX12 | PEAR1 | ACRBP | ABLIM3 | F13A1 | CMTM5 | GNG11 | DDEF2 |
| C7orf41 | ASAP2 | ANKRD9 | | | | | | |
| Module yellow | | | | | | | | |
| SDCBP | LRRK2 | RP2 | FAM49B | MNDA | UBE2W | LOC100129960 | NDUFS3 | DDX3X |
| PLXNC1 | MCL1 | JMJD1C | CENTB2 | ST8SIA4 | SNX13 | SNX10 | ELOVL5 | C12orf35 |
| SPAG9 | MRPS12 | CYB5R4 | LOC729279 | LYST | POMGNT1 | SPOPL | PELI1 | OGFRL1 |
| SHOC2 | CDC42EP3 | ACSL4 | | | | | | |
| Module cyan | | | | | | | | |
| LOC440313 | SPRYD3 | LOC642469 | DPYSL5 | GPR175 | EPB42 | SERPINA13 | LOC100131726 | MUC6 |
| HBD | SLC25A39 | AHSP | SELENBP1 | LOC100132499 | RNF213 | ROPN1B | LOC100131391 | LOC100131164 |
| STRADB | IFIT1L | FBXO7 | UBXN6 | EPB49 | HBQ1 | ALAS2 | SEMA6B | TESC |
| HBE1 | GUK1 | LOC652140 | | | | | | |
| Module turquoise | | | | | | | | |
| ITPRIP | NUMB | REPS2 | AQP9 | SEPX1 | STX3 | FCGR2A | RNF149 | BASP1 |
| NCF4 | RBM47 | NFIL3 | MXD1 | PHC2 | LIMK2 | TLR1 | GK | BCL6 |
| CSF3R | GCA | LOC730278 | SLC22A4 | NDEL1 | CEACAM3 | RALB | PFKFB4 | LOC654133 |
| PSG3 | MANSC1 | CXCR1 | | | | | | |

TABLE 21

| Top 30 Genes with the Highest Gene Connectivity Correlated with Brain Size Variation in Control | | | | | | | | |
|---|---|---|---|---|---|---|---|---|
| Module greenyellow | | | | | | | | |
| NCAPG | HMMR | DLGAP5 | CCNB2 | CDC20 | TOP2A | C12orf48 | CDKN3 | CDC45L |
| CEP55 | NUSAP1 | BUB1 | KIF11 | CHEK1 | ASPM | TYMS | CDC2 | NEK2 |
| DEPDC1B | PTTG3P | PTTG1 | KIAA0101 | AURKA | OIP5 | MND1 | MELK | CCNA2 |
| GMNN | CDCA5 | CCNE2 | | | | | | |

TABLE 21-continued

| Top 30 Genes with the Highest Gene Connectivity Correlated with Brain Size Variation in Control | | | | | | | | |
|---|---|---|---|---|---|---|---|---|
| Module grey60 | | | | | | | | |
| TNFRSF17 | MGC29506 | TXNDC5 | LOC647450 | LOC652493 | ABCB9 | LOC652694 | LOC642113 | IGJ |
| LOC647506 | CD38 | GLDC | SEC11C | IGLL1 | CAMK1G | CRKRS | FKBP11 | ARMET |
| CAV1 | FAM46C | GGH | IGLL3 | ITM2C | LOC390712 | LOC729768 | HSP90B1 | PRDX4 |
| ELL2 | GMPPB | DNAJB11 | | | | | | |
| Module midnightblue | | | | | | | | |
| ITGB5 | PDE5A | ITGB3 | TSPAN9 | GP9 | TUBB1 | PPBP | CTDSPL | CTTN |
| SDPR | PTGS1 | NRGN | NCKAP5 | SEPT5 | PTCRA | SH3BGRL2 | ACRBP | ITGA2B |
| ALOX12 | TREML1 | C5orf4 | ESAM | ELOVL7 | F13A1 | GNG11 | PROS1 | DDEF2 |
| GP1BA | ANKRD9 | ASAP2 | | | | | | |
| Module yellow | | | | | | | | |
| SDCBP | LRRK2 | ZFYVE16 | NDUFS3 | CPSF4 | FAM49B | DCTPP1 | DNAJC8 | KRTCAP2 |
| TMEM154 | WDR54 | MEGF9 | LOC391811 | LOC100129960 | CMTM6 | PELI1 | NDUFS8 | NUDT1 |
| PLXNC1 | SLC12A6 | PAFAH1B3 | ADSL | SPAG9 | NHP2 | ITPA | NDUFB8 | SLC40A1 |
| CPEB2 | MRPS12 | APAF1 | | | | | | |
| Module cyan | | | | | | | | |
| LOC642469 | GPR175 | LOC100131726 | LOC440313 | SPRYD3 | MUC6 | AHSP | HBD | SLC25A39 |
| LOC100132499 | STRADB | EPB42 | LOC389599 | DPYSL5 | SERPINA13 | FBXO7 | EPB49 | UBXN6 |
| LOC100131164 | LOC100131391 | RNF213 | MIR98 | SELENBP1 | MRPL40 | LOC645944 | C1orf77 | LOC728453 |
| PMM1 | HBE1 | LOC100130255 | | | | | | |
| Module turquoise | | | | | | | | |
| GCA | NUMB | PFKFB4 | REPS2 | TLR6 | SRGN | RNF149 | TLR1 | ACSL1 |
| CSF3R | ITPRIP | LIMK2 | FCGR2A | SEPX1 | PHC2 | LILRB3 | STX3 | GK |
| FRAT2 | FPR1 | NFIL3 | PSG9 | LIN7A | S100A11 | TNFRSF1A | RALB | AQP9 |
| NCF4 | FTHL12 | LAMP2 | | | | | | |

TABLE 22

| Top 30 Genes with the Highest Gene Significance Correlated with Brain Size Variation in ASD | | | | | | | | |
|---|---|---|---|---|---|---|---|---|
| Module greenyellow | | | | | | | | |
| RNASEH2A | C6orf129 | EBP | STOML2 | RRM1 | RAPGEF5 | STMN1 | CENPM | CCNF |
| TOP2A | PSMB7 | KIF20A | FAM19A2 | PDCD1 | BIRC5 | LOC441455 | CDCA5 | PHF19 |
| FEN1 | MCM2 | CCNB2 | MND1 | RACGAP1 | PTTG3P | MTHFD1L | FABP5L2 | CHST12 |
| UBE2T | PLS3 | CENPA | | | | | | |
| Module grey60 | | | | | | | | |
| PDIA4 | RPN2 | MOXD1 | MTDH | IGLL3 | CRKRS | HYOU1 | LOC647506 | BCL2L11 |
| KLHL14 | SDF2L1 | IGLL1 | ABCB9 | EAF2 | DENND5B | IRF4 | ARMET | TNFRSF17 |
| ITM2C | PDIA5 | LOC652694 | DNAJB11 | SPATS2 | LOC647460 | SEC11C | GLDC | POU2AF1 |
| LOC541471 | C14orf145 | MGC29506 | | | | | | |
| Module midnightblue | | | | | | | | |
| RNF11 | PDGFC | MPP1 | CDC14B | TUBB1 | TPM1 | ZNF185 | P2RY12 | MMD |
| SDPR | NCKAP5 | SPOCD1 | FHL1 | MARCH2 | ARHGAP18 | ASAP2 | VCL | FRMD3 |
| CALD1 | GNG11 | GUCY1B3 | LY6G6F | F13A1 | LEPR | JAM3 | MYLK | BMP6 |
| ELOVL7 | PGRMC1 | SPARC | | | | | | |
| Module yellow | | | | | | | | |
| BLMH | DDT | SSFA2 | PHPT1 | TLR8 | HDAC1 | OSGIN2 | FAM159A | MAPK14 |
| NDUFB9 | LAGE3 | DMXL2 | PDCD2L | SLC2A1 | NTHL1 | STRA13 | NPM3 | HIST1H2AC |
| C6orf108 | LCP2 | CLPP | NDUFA7 | MRPL55 | MCTP1 | WBSCR22 | MFSD1 | LMAN2 |
| CDK10 | FAM105A | DUSP6 | | | | | | |
| Module cyan | | | | | | | | |
| EEF1D | LOC728453 | ZNF33B | PTDSS1 | PMM1 | TULP4 | ARL1 | CSDA | WDR40A |
| LOC731985 | TRIM58 | SSNA1 | SF4 | RPS29 | ADIPOR1 | SNCA | ERCC5 | GALT |
| LOC100132499 | LOC653635 | LOC440359 | ANKRD54 | LOC130773 | PDZK1IP1 | LOC441775 | MRPL40 | LOC100130255 |
| WDR70 | MARCH8 | VIL2 | | | | | | |
| Module turquoise | | | | | | | | |
| LOC346887 | C9orf72 | LAX1 | IGFBP4 | C3orf26 | NOTCH2 | RGS18 | NCOA4 | TRIB2 |
| MAX | BID | LOC641710 | CDS2 | MRPS9 | B4GALT5 | FAM193B | DSE | LOC388707 |
| SLAMF6 | IRAK3 | MEF2A | PARP1 | SNN | ARPC5 | AUTS2 | SNX6 | FAM98A |
| C9orf66 | HEY1 | ALOX5 | | | | | | |

TABLE 23

| Top 30 Genes with the Highest Gene Significance Correlated with Brain Size Variation in Control | | | | | | | | |
|---|---|---|---|---|---|---|---|---|
| Module greenyellow | | | | | | | | |
| CDC2 | KIF11 | NUSAP1 | MELK | PRC1 | DTL | DEPDC1B | TTK | OIP5 |
| CCNA2 | UHRF1 | TYMS | KIF20A | KPNA2 | MCM10 | UBE2C | TK1 | CENPE |
| NUF2 | ASPM | KIAA0101 | DLGAP5 | CDC20 | CCNE2 | DONSON | EZH2 | GMNN |
| MGC40489 | NEK2 | NCAPG | | | | | | |
| Module grey60 | | | | | | | | |
| IGLL3 | CRKRS | CAMK1G | PERP | HSPA13 | SPATS2 | IGLL1 | SLC25A4 | GGH |
| CD38 | ELL2 | UAP1 | MGC29506 | BIK | LOC401845 | PRDX4 | TNFRSF17 | XBP1 |
| SEC61B | GLDC | LOC649210 | LOC652694 | LOC652493 | FKBP11 | IGJ | CAV1 | TXNDC5 |
| LOC649923 | LOC647506 | LOC652102 | | | | | | |
| Module midnightblue | | | | | | | | |
| SMOX | ARHGAP18 | SPARC | HIST1H2AG | C15orf26 | PLOD2 | C16orf68 | ARHGAP21 | TREML1 |
| XPNPEP1 | ANKRD9 | TAL1 | C5orf62 | C11orf59 | KIFC3 | LOC650261 | LOC441481 | ESAM |
| TSPAN9 | GP9 | GNG11 | GRB14 | CMTM5 | ITGA2B | CLDN5 | CALD1 | PF4V1 |
| LY6G6F | TUBA4A | GPX1 | | | | | | |
| Module yellow | | | | | | | | |
| ZNF426 | ELMOD2 | ILKAP | LOC644739 | PRDM1 | PDPK1 | LOC653344 | TGFBR2 | UPF2 |
| ZNF480 | DMAP1 | CCDC28B | VARS | FAM44A | NTHL1 | KLHDC4 | MYO9A | OTUD1 |
| C10orf118 | IPMK | TCP11L2 | PHF3 | BTBD2 | PHF20L1 | PCSK7 | STRA13 | PDE4B |
| KIF22 | RTN4 | TMEM106C | | | | | | |
| Module cyan | | | | | | | | |
| SNORD8 | ZNF33A | AKAP7 | C20orf108 | BLVRB | UBE2F | DERL2 | PPIG | EWSR1 |
| SF4 | HPS1 | C17orf68 | HEMGN | DSCAM | TESC | LOC100134108 | NDUFAF1 | LOC100134102 |
| LOC100130769 | HECTD3 | GSPT1 | MAPK13 | KRT1 | SRRD | SNF8 | PPP2R2A | IGF2BP2 |
| LOC652968 | RN5S9 | PDZK1IP1 | | | | | | |
| Module turquoise | | | | | | | | |
| PPARBP | PPOX | ZNF551 | ZNF135 | ACOT4 | MSTO1 | CEP290 | MPZL1 | CPPED1 |
| KIAA1641 | METT11D1 | NUP43 | BTBD6 | OPTN | METTL2A | USP36 | TMEM45B | TOP3B |
| XYLT2 | ZNF805 | ALG9 | TBK1 | IRAK1BP1 | DIS3L | EFHC2 | TMEM217 | MGC42367 |
| LRRC25 | IL8RB | DCAF7 | | | | | | |

TABLE 24

| Top 30 Genes with the Highest Module Membership Correlated with Brain Size Variation in ASD | | | | | | | | |
|---|---|---|---|---|---|---|---|---|
| Module greenyellow | | | | | | | | |
| DLGAP5 | CDKN3 | HMMR | OIP5 | KIAA0101 | CEP55 | NUSAP1 | KIF11 | BUB1 |
| TOP2A | ASPM | CCNA2 | CCNB2 | TYMS | CHEK1 | NCAPG | PTTG3P | CDC45L |
| AURKA | MELK | MCM10 | CDC2 | CENPE | GMNN | UBE2C | PRC1 | PTTG1 |
| CDCA5 | MND1 | TTK | | | | | | |
| Module grey60 | | | | | | | | |
| TXNDC5 | ABCB9 | TNFRSF17 | MGC29506 | FKBP11 | CD38 | CRKRS | SEC11C | LOC647506 |
| CAMK1G | LOC647450 | LOC652694 | CAV1 | LOC652493 | GGH | DNAJB11 | FAM46C | ITM2C |
| ELL2 | GLDC | IGLL1 | IGJ | ARMET | LOC390712 | LOC642131 | HSP90B1 | SLC25A4 |
| LOC642113 | IGLL3 | LOC651751 | | | | | | |
| Module midnightblue | | | | | | | | |
| SH3BGRL2 | GP9 | CSTDPL | PDE5A | TUBB1 | ESAM | ITGB5 | SEPT5 | TREML1 |
| PTGS1 | CTTN | PTCRA | MYLK | NRGN | MARCH2 | SELP | ALOX12 | TSPAN9 |
| SDPR | ACRBP | ABLIM3 | PEAR1 | DDEF2 | F13A1 | ITGA2B | GNG11 | ASAP2 |
| CMTM5 | DNM3 | C7orf41 | | | | | | |
| Module yellow | | | | | | | | |
| NDUFS3 | POMGNT1 | LOC729279 | CPSF4 | DGCR6 | MRPS12 | AIP | POLR3C | PAFAH1B3 |
| KRTCAP2 | MRPL37 | ADSL | L3MBTL2 | BMS1 | NUDT1 | IMP4 | RPUSD2 | VEGFB |
| LAGE3 | WDR54 | C19orf53 | LAT | C11orf2 | EIF3B | B4GALT3 | APRT | DHPS |
| TRAPPC6A | NDUFS8 | C17orf70 | | | | | | |
| Module cyan | | | | | | | | |
| LOC642469 | SPRYD3 | LOC440313 | SERPINA13 | HBD | EPB42 | LOC100131726 | DPYSL5 | AHSP |
| SLC25A39 | GPR175 | MUC6 | SELENBP1 | ROPN1B | LOC100131164 | IFIT1L | LOC100131391 | STRADB |
| RNF213 | FBXO7 | HBQ1 | UBXN6 | EPB49 | ALAS2 | TESC | SESN3 | SEMA6B |
| WDR40A | HBE1 | TMEM111 | | | | | | |
| Module turquoise | | | | | | | | |
| ITPRIP | REPS2 | SEPX1 | STX3 | AQP9 | FCGR2A | NFIL3 | NUMB | LOC730278 |
| PSG3 | BASP1 | TLR1 | RNF149 | NCF4 | LOC100134728 | RALB | PHC2 | LIMK2 |

TABLE 24-continued

| Top 30 Genes with the Highest Module Membership Correlated with Brain Size Variation in ASD | | | | | | | | |
|---|---|---|---|---|---|---|---|---|
| TLR8 | GK | PSG9 | SLC22A4 | CCPG1 | CEACAM3 | FTHL12 | FAM49A | KCNJ2 |
| GCA | FPR1 | LOC729009 | | | | | | |

TABLE 25

| Top 30 Genes with the Highest Module Membership Correlated with Brain Size Variation in Control | | | | | | | | |
|---|---|---|---|---|---|---|---|---|
| Module greenyellow | | | | | | | | |
| C12orf48 | HMMR | NCAPG | CDKN3 | DLGAP5 | CCNB2 | CDC20 | CDC45L | TOP2A |
| CHEK1 | PTTG3P | NUSAP1 | CEP55 | PTTG1 | MND1 | CDC2 | BUB1 | DEPDC1B |
| NEK2 | KIAA0101 | KIF11 | AURKA | GMNN | OIP5 | TYMS | ASPM | CCNE2 |
| NUF2 | CCNA2 | CDCA5 | | | | | | |
| Module grey60 | | | | | | | | |
| MGC29506 | TNFRSF17 | TXNDC5 | ABCB9 | LOC647450 | LOC652694 | LOC652493 | LOC642113 | GLDC |
| LOC647506 | CD38 | IGJ | SEC11C | IGLL1 | CRKRS | FKBP11 | CAV1 | BUB1 |
| ARMET | CAMK1G | FAM46C | GGH | ITM2C | LOC390712 | IGLL3 | DNAJB11 | SPATS2 |
| HSP90B1 | XBP1 | ELL2 | | | | | | |
| Module midnightblue | | | | | | | | |
| ITGB5 | GP9 | PDE5A | TSPAN9 | SDPR | TUBB1 | CTTN | ITGB3 | PTCRA |
| NRGN | PPBP | PTGS1 | SEPT5 | NCKAP5 | CTDSPL | ESAM | ALOX12 | SH3BGRL2 |
| TREML1 | F13A1 | ACRBP | C5orf4 | GP1BA | ELOVL7 | ITGA2B | GNG11 | DDEF2 |
| PROS1 | TNFSF4 | ANKRD9 | | | | | | |
| Module yellow | | | | | | | | |
| CPSF4 | NDUFS3 | DNAJC8 | LOC391811 | ITPA | PAFAH1B3 | KRTCAP2 | ADSL | NDUFS8 |
| WDR54 | DCTPP1 | SAE1 | NDUFB8 | NUDT1 | SCAMP3 | CUTA | C19orf48 | CCT7 |
| NHP2L1 | NHP2 | PDXP | PTPRCAP | LSM2 | MRPS12 | ATIC | TTC4 | CCT3 |
| NXT1 | IMP3 | DPH2 | | | | | | |
| Module cyan | | | | | | | | |
| LOC642469 | GPR175 | AHSP | LOC100131726 | LOC440313 | SPRYD3 | MUC6 | HBD | SLC25A39 |
| EPB49 | EPB42 | STRADB | LOC389599 | FBXO7 | UBXN6 | DPYSL5 | LOC100131164 | SERPINA13 |
| SELENBP1 | LOC100131391 | RNF213 | HBE1 | TRIM58 | MYL4 | SNCA | SEMA6B | CSDA |
| LOC440359 | ROPN1B | HBQ1 | | | | | | |
| Module turquoise | | | | | | | | |
| GCA | PFKFB4 | SRGN | TLR6 | NUMB | SEPX1 | TLR1 | FTHL12 | ACSL1 |
| LIMK2 | MNDA | S100A11 | NFIL3 | ITPRIP | RALB | LIN7A | TLR8 | STX3 |
| LILRB3 | PSG9 | FCGR2A | GK | LOC730278 | FTHL7 | PHC2 | REPS2 | PGCP |
| FPR1 | RNF149 | LOC729009 | | | | | | |

Discussion

In this naturalistic study of autism brain size and gene expression conducted during very early development, evidence of specific early functional genomic pathology related to brain development and size in vivo in ASD toddlers was identified. Results show abnormal brain development and size in ASD toddlers involves disruption of cell cycle and protein folding networks plus induction of abnormal functioning of cell adhesion, translation and immune gene networks. Also, dysregulation of DNA-damage, cell cycle regulation, apoptosis, mitogenic signaling, cell differentiation and immune system response gene networks was replicated in both ASD study groups. It was previously reported several of these gene networks are disrupted in prefrontal cortex in postmortem ASD children[2]. Thus, postmortem and the present in vivo evidence raise the theory that very early, probably prenatal, disruption of several key developmental gene networks leads to known defects of abnormal neuron number[6], brain[6-9,11,12] and body[27] growth, and synaptic development and function[28], as previously reported.[7,11,29-31]

In the brain in animal model studies,[32,33] cell cycle and protein folding networks impact cerebral cortical neuron production and synapse development, respectively, and, therefore brain and cortical size and function. Using a novel approach that combines MRI and gene expression, it was discovered that gene expression signals of both networks are detectable in the blood in control toddlers and, remarkably, are strongly correlated with brain and cerebral size, including cortical surface area. Variations in brain size in ASD toddlers are only weakly correlated with cell production and protein folding expression levels, and instead are more strongly related to a variety of other functions, namely cell adhesion, immune/inflammation, translation and other developmental processes. Thus, even given similar brain sizes or cortical surface areas in ASD versus control toddlers, the genetic foundations for brain development and growth are apparently distinctly different. Dysfunction of cell cycle processes has long been theorized to underlie brain growth pathology in ASD[7]. The present evidence along with recent evidence of a 67% overabundance of prefrontal cortical neurons in ASD boys[6] underscores the relevance of this theory to elucidating the molecular and cellular developmental neuropathology and origins of ASD.

Dysregulation of cell adhesion networks, as well as protein folding in ASD toddlers, likely point to underlying abnormalities of synapse development and function, as well as to global alterations of transcriptional regulation.[34,35] Accumulation of misfolded proteins leads to the Unfolded Protein Response (UPR)[36]. Converging evidence shows that misfolded proteins and UPR may underlie impaired synaptic function in autism[37], as well as in neurodegenerative disorders[38]. Moreover, results of modeling studies of neurexin and neuroligin mutations identified in autistic patients, show ER retention and point to UPR as a mechanism behind synaptic malfunction in autism[34,39,40]. Due to preponderance of highly penetrant mutations, the disruption of synaptic cell adhesion molecules is a well-established mechanism underlying ASD pathophysiologyl[4], and recent evidence extends implications to dysregulation at the network level[28]. The instant findings show that genes of the integrin family are abnormally "activated" in ASD, and thus may underlie aberrant synaptic structure and function[41] as well as affect regulation of apoptosis, proliferation, migration and cell differentiation. Integrins also play roles in modulation of microglia behavior, and thereby additionally participate in regulation of neural inflammation and immune response[41].

Immune gene networks were dysregulated in both ASD study groups and were among top networks correlated with brain size in ASD, but not TD, toddlers. Dysregulation of immune/neuroinflammation mechanisms is a strong signal in a large number of studies of older ASD children and adults.[26,42] The present study, however, is the first to find significant dysregulation of immune/neuroinflammation gene networks at about the age of first clinical risk signs of ASD and the first to show a relationship with ASD brain development. Recently, abnormal immune/neuroinflammation gene expression in frozen cortex tissue has been reported in two independent studies of young as well as older postmortem autism cases.[2,28] Microglial activation, which typically occurs in association with neuroinflammation, was reported in prefrontal cortex across all ages studied from 2 years to adulthood in ASD.[43,44] While evidence of immune involvement has been argued to be a secondary later abnormality in ASD, there is no experimental evidence to favor that idea over the possibility that ASD involves both prenatal immune alterations as demonstrated by studies modeling prenatal maternal immune activation (MIA) in rodents[45]. Abnormal cell cycle control and cortical cell number strongly point to prenatal origins, and whether and how they and other genetic dysregulation and pathological cellular events intersect with immune alterations deserves careful investigation. In either event, this study provides the first evidence that immune gene networks are dysregulated at the age of first clinical concern and referral at 1 to 2 years of age and already relate to ASD brain development.

This study is unique in that it identified a candidate genomic signature that has a high level of accuracy, specificity and sensitivity in diagnostic classification of Discovery ASD vs control (TD and contrast) toddlers all of whom came from a general, naturalistic population screening. The strategy, which used the 1-Year Well-Baby Check-Up Approach, allowed the unbiased, prospective recruitment and study of ASD and control toddlers as they occur in the community pediatric clinics, something not previously done by research groups. Thus, not only did the ASD toddlers reflect the wide clinical phenotypic range expected in community clinics but the control toddlers also reflect the natural mix of typically developing, mild language delayed, transient language delayed, and global developmental delayed toddlers commonly seen in community clinics. Against this challenging control group, the signature of this study surprisingly correctly identified 82.5% of Discovery ASD toddlers. The candidate signature from this discovery sample performed well in the independent replication cohort, despite the completely different version of microarray chip used with that cohort.

This very good level of accuracy outperforms other behavioral and genetic screens for ASD infants and toddlers reported in the literature, especially when compared with performance of other tests applied to the young general pediatric population (as opposed to preselected syndromic patients or ASD patients from multiplex families). For example, the M-CHAT, a commonly used parent report screen, has very low specificity (27%)[46] and positive predictive value (PPV, 11-54%) when used in general populations[47,48]. While important strides have been made in understanding possible genetic risk factors in autism[3], current DNA tests detect only rare autism cases and lack specificity[49] or confirm autism at older ages and have not been demonstrated to be effective in ASD infants and toddlers[26]. Thus, the candidate functional genomic signature reported here, developed from a general pediatric population, is currently the best performing blood- or behavior-based candidate classifier in ASD infants and toddlers.

The results of this study support the model that in a great majority of affected toddlers, ASD involves disruption of a comment set of key neural developmental genetic pathways. These commonly disrupted pathways govern neuron number and survival, neuronal functional integrity and synapse formation, which are key neural developmental processes. Disruption of immune genetic networks is also involved in the majority ASD toddlers, an effect not detected in DNA studies of gene mutations and CNVs, but one that is found in ASD prefrontal brain tissue. Evidence indicates it is no longer a question of whether immune disruption is involved in ASD, but rather why and how. A subset of genes in these common pathways—notably translation, immune/inflammation, cell adhesion and cell cycle genes—provide a candidate genomic signature of risk for autism at young ages. Knowledge of these common pathways can facilitate research into biological targets for biotherapeutic intervention and development of accurate biomarkers for detecting risk for ASD in infants in the general pediatric population.

REFERENCES

1. Courchesne, E. et al. Unusual brain growth patterns in early life in patients with autistic disorder: an MRI study. Neurology 57, 245-54 (2001).
2. Redcay, E. & Courchesne, E. When is the brain enlarged in autism? A meta-analysis of all brain size reports. Biological Psychiatry 58, 1-9 (2005).
3. Courchesne, E. et al. Mapping early brain development in autism. Neuron 56, 399-413 (2007).
4. Stanfield, A. C. et al. Towards a neuroanatomy of autism: a systematic review and meta-analysis of structural magnetic resonance imaging studies. Eur Psychiatry 23, 289-99 (2008).
5. Vaccarino, F. M. & Smith, K. M. Increased brain size in autism—what it will take to solve a mystery. Biol Psychiatry 66, 313-5 (2009).
6. Stigler, K. A., McDonald, B. C., Anand, A., Saykin, A. J. & McDougle, C. J. Structural and functional magnetic resonance imaging of autism spectrum disorders. Brain Res 1380, 146-61 (2011).
7. Courchesne, E., Campbell, K. & Solso, S. Brain growth across the life span in autism: age-specific changes in anatomical pathology. Brain Res 1380, 138-45 (2011).
8. Lainhart, J. E. & Lange, N. Increased neuron number and head size in autism. JAMA 306, 2031-2 (2011).
9. Courchesne, E. et al. Neuron number and size in prefrontal cortex of children with autism. JAMA 306, 2001-10 (2011).

10. Chow, M. L. et al. Age-dependent brain gene expression and copy number anomalies in autism suggest distinct pathological processes at young versus mature ages. PLoS Genet 8, e1002592 (2012).

11. Pinto, D. et al. Functional impact of global rare copy number variation in autism spectrum disorders. Nature 466, 368-372 (2010).

12. Zoghbi, H. Y. & Bear, M. F. Synaptic dysfunction in neurodevelopmental disorders associated with autism and intellectual disabilities. Cold Spring Harb Perspect Biol 4(2012).

13. Pierce, K. et al. Detecting, studying, and treating autism early: the one-year well-baby check-up approach. J Pediatr 159, 458-465 e1-6 (2011).

14. Luyster, R. et al. The Autism Diagnostic Observation Schedule-toddler module: a new module of a standardized diagnostic measure for autism spectrum disorders. J Autism Dev Disord 39, 1305-20 (2009).

15. Lord, C. et al. The Autism Diagnostic Observation Schedule—Generic: A Standard Measure of Social and Communication Deficits Associated with the Spectrum of Autism. in Journal of autism and developmental disorders Vol. 30 205-223-223 (Springer Netherlands, 2000).

16. Mullen, E. M. Mullen Scales of Early Learning, (American Guidance Service Inc., MN, 1995).

17. Sparrow, S., Cicchetti D V, Balla D A. Vineland Adaptive Behavior Scales. Second Edition. Survey Forms Manual. Pearson Assessments (2005).

18. Hastie, T. & Tibshirani, R. Generalized additive models for medical research. Stat Methods Med Res 4, 187-96 (1995).

19. Sanders, S. J. et al. Multiple Recurrent De Novo CNVs, Including Duplications of the 7q11.23 Williams Syndrome Region, Are Strongly Associated with Autism. Neuron 70, 863-85 (2011).

20. Rossin, E. J. et al. Proteins encoded in genomic regions associated with immune-mediated disease physically interact and suggest underlying biology. PLoS Genet 7, e1001273 (2011).

21. Stranger, B. E. et al. Relative impact of nucleotide and copy number variation on gene expression phenotypes. Science 315, 848-53 (2007).

22. Luo, R. et al. Genome-wide transcriptome profiling reveals the functional impact of rare de novo and recurrent CNVs in autism spectrum disorders. Am J Hum Genet 91, 38-55 (2012).

23. Glatt, S. J. et al. Blood-based gene expression signatures of infants and toddlers with autism. J Am Acad Child Adolesc Psychiatry 51, 934-44 e2 (2012).

24. Kong, S. W. et al. Characteristics and predictive value of blood transcriptome signature in males with autism spectrum disorders. PloS one 7, e49475 (2012).

25. Chawarska, K. et al. Early generalized overgrowth in boys with autism. Arch Gen Psychiatry 68, 1021-31 (2011).

26. Voineagu, I. et al. Transcriptomic analysis of autistic brain reveals convergent molecular pathology. Nature 474, 380-4 (2011).

27. Courchesne, E. & Pierce, K. Brain overgrowth in autism during a critical time in development: implications for frontal pyramidal neuron and interneuron development and connectivity. Int J Dev Neurosci 23, 153-70 (2005).

28. Clement, J. P. et al. Pathogenic SYNGAP1 mutations impair cognitive development by disrupting maturation of dendritic spine synapses. Cell 151, 709-23 (2012).

29. Baudouin, S. J. et al. Shared synaptic pathophysiology in syndromic and nonsyndromic rodent models of autism. Science 338, 128-32 (2012).

30. Mitsuhashi, T. & Takahashi, T. Genetic regulation of proliferation/differentiation characteristics of neural progenitor cells in the developing neocortex. Brain Dev 31, 553-7 (2009).

31. Good, M. C., Zalatan, J. G. & Lim, W. A. Scaffold proteins: hubs for controlling the flow of cellular information. Science 332, 680-6 (2011).

32. Falivelli, G. et al. Inherited genetic variants in autism-related CNTNAP2 show perturbed trafficking and ATF6 activation. Hum Mol Genet 21, 4761-73 (2012).

33. Mendillo, M. L. et al. HSF1 drives a transcriptional program distinct from heat shock to support highly malignant human cancers. Cell 150, 549-62 (2012).

34. Walter, P. & Ron, D. The unfolded protein response: from stress pathway to homeostatic regulation. Science 334, 1081-6 (2011).

35. Fujita, E. et al. Autism spectrum disorder is related to endoplasmic reticulum stress induced by mutations in the synaptic cell adhesion molecule, CADM1. Cell Death Dis 1, e47 (2010).

36. Matus, S., Glimcher, L. H. & Hetz, C. Protein folding stress in neurodegenerative diseases: a glimpse into the ER. Curr Opin Cell Biol 23, 239-52 (2011).

37. Zhang, C. et al. A neuroligin-4 missense mutation associated with autism impairs neuroligin-4 folding and endoplasmic reticulum export. J Neurosci 29, 10843-54 (2009).

38. De Jaco, A. et al. Neuroligin trafficking deficiencies arising from mutations in the alpha/beta-hydrolase fold protein family. J Biol Chem 285, 28674-82 (2010).

39. Milner, R. & Campbell, I. L. The integrin family of cell adhesion molecules has multiple functions within the CNS. J Neurosci Res 69, 286-91 (2002).

40. Rossignol, D. A. & Frye, R. E. A review of research trends in physiological abnormalities in autism spectrum disorders: immune dysregulation, inflammation, oxidative stress, mitochondrial dysfunction and environmental toxicant exposures. Mol Psychiatry 17, 389-401 (2012).

41. Morgan, J. T. et al. Microglial activation and increased microglial density observed in the dorsolateral prefrontal cortex in autism. Biological Psychiatry 68, 368-76 (2010).

42. Vargas, D. L., Nascimbene, C., Krishnan, C., Zimmerman, A. W. & Pardo, C. A. Neuroglial activation and neuroinflammation in the brain of patients with autism. Annals of neurology 57, 67-81 (2005).

43. Oskvig, D. B., Elkahloun, A. G., Johnson, K. R., Phillips, T. M. & Herkenham, M. Maternal immune activation by LPS selectively alters specific gene expression profiles of interneuron migration and oxidative stress in the fetus without triggering a fetal immune response. Brain Behav Immun 26, 623-34 (2012).

44. Eaves, L. C., Wingert, H. & Ho, H. H. Screening for autism: agreement with diagnosis. Autism 10, 229-42 (2006).

45. Kleinman, J. M. et al. The modified checklist for autism in toddlers: a follow-up study investigating the early detection of autism spectrum disorders. J Autism Dev Disord 38, 827-39 (2008).

46. Chlebowski, C., Robins, D. L., Barton, M. L. & Fein, D. Large-scale use of the modified checklist for autism in low-risk toddlers. Pediatrics 131, e1121-7 (2013).

47. Devlin, B. & Scherer, S. W. Genetic architecture in autism spectrum disorder. Curr Opin Genet Dev 22, 229-37 (2012).

48. Roesser, J. Diagnostic yield of genetic testing in children diagnosed with autism spectrum disorders at a regional referral center. Clin Pediatr (Phila) 50, 834-43 (2011).

Example 2

Additional Methods, Analyses, and Results

Subjective Recruitment, Tracking and Developmental Evaluation

All toddlers were developmentally evaluated by a Ph.D. level psychologist and those that were younger than 3 years at the time of blood draw were tracked every 6 months until their $3^{rd}$ birthday when a final diagnosis was given. Only toddlers with a provisional or confirmed ASD diagnosis were included in this study. Toddlers were recruited via the 1-Year Well-Baby Check-Up Approach, a new general population based screening approach designed to identify toddlers with an ASD around the $1^{st}$ birthday or from general community sources (e.g., referred by a friend, or response to the website). In brief, the 1-Year Well-Baby Check-Up Approach utilizes a broad band screening tool, the CSBS DP IT Checklist) implemented at the routine first year pediatric exam. The recent study, which included the participation of 137 pediatricians who implemented >10,000 CSBS screens, showed that 75% of toddlers that fail the screen at the $1^{st}$ year exam have a true delay (either ASD, language delay, global developmental delay or other condition). While ASD toddlers were as young as 12 months at the time of blood sampling, all but 3 toddlers have been tracked and diagnosed using the ADOS toddler module[3] until at least age two years, an age where diagnosis of ASD is relatively stable[4-6]. Toddlers received the ADOS module that was most appropriate for their age and intellectual capacity. For the Discovery sample 64% of ASD population had an ADOST, 31% had an ADOS 1, and 5% had an ADOS 2 while for the replication sample 32% of ASD population had an ADOS T, 48% had an ADOS 1 and 20% had an ADOS 2. Only toddlers with a provisional or confirmed ASD diagnosis were included in this study. Twenty-four final diagnoses for participants older than 30 months were also confirmed with the Autism Diagnostic Interview—Revised[3].

All toddlers participated in a battery of standardized and experimental tests that included the Autism Diagnostic Observation Schedule[3], the Mullen Scales of Early Learning' and the Vineland Adaptive Behavior Scales[8]. Diagnoses were determined via these assessments and the Diagnostic and Statistical Manual, Fourth Edition (DSM IV-TR)[9]. Testing sessions generally lasted 4 hours and occurred across 2 separate days and the blood sample was usually taken at the end of the first day. All standardized assessments were administered by experienced Ph.D. level psychologists.

Ethnicity or Race information was self-reported by parents. Discovery subjects: ASD (87 subjects) were 44 Caucasian, 24 Hispanic, 13 Mixed, 4 Asian, 1 Indian, 1 African-American, ethnicity; control (55 subjects) were, 38 Caucasian, 7 Hispanic, 5 mixed, 2 African American, 3 Asian ethnicity. Replication subjects: ASD (44 subjects) were 23 Caucasian, 13 Hispanic, 6 mixed, 2 Asian ethnicity; control (29 subjects) were 20 Caucasian, 4 Hispanic/Latino, 3 mixed, 1 African American ethnicity, 1 unreported.

In order to monitor health status, the temperature of each toddler was taken using an ear digital thermometer immediately preceding the blood draw. If temperature was higher than 99, then the blood draw was rescheduled for a different day. Parents were also asked questions regarding their child's health status such as the presence of a cold or flu, and if any illnesses were present or suspected, the blood draw was rescheduled for a different day.

RNA Extraction, Preparation and Quality Control

Four-to-six ml of blood was collected into EDTA-coated tubes from toddlers on visits when they had no fever, cold, flu, infections or other illnesses or use of medications for illnesses 72 hours prior blood-draw. Blood samples were passed over a LEUKOLOCK filter (Ambion, Austin, Tex., USA) to capture and stabilize leukocytes and immediately placed in a −20° (C.) freezer.

Total RNA was extracted following standard procedures and manufacturer's instructions (Ambion, Austin, Tex., USA). In principle, LEUKOLOCK disks were freed from RNA-later and Tri-reagent was used to flush out the captured lymphocyte and lyse the cells. RNA was subsequently precipitated with ethanol and purified though washing and cartridge-based steps. The quality of mRNA samples was quantified by the RNA Integrity Number (RIN) and values of 7.0 or greater were considered acceptable[10] all processed RNA samples passed RIN quality control. Quantification of RNA was performed using Nanodrop (Thermo Scientific, Wilmington, Del., USA). Samples were prep in 96-well plates at the concentration of 25 ng/uL.

MRI Scanning and Neuroanatomic Measurement

A T1-weighted IR-FSPGR sagittal protocol (TE=2.8 ms, TR=6.5 ms, flip angle=12 deg, bandwidth=31.25 kHz, FOV=24× cm, slice thickness=1.2 mm, 165 images) was collected during natural sleep[11].

FSL's linear registration tool (FLIRT) rigidly registered brain images to a custom template that was previously registered into MNI space[12]. Registered images were then processed through FSL's brain extraction tool (BET) removing skull and non-brain tissue[13]. Remaining non-brain tissue was removed by an anatomist to ensure accurate surface measurement. Gray matter, white matter and CSF were segmented via a modified version of the FAST algorithm[14] using partial volumes rather than neighboring voxels to increase sensitivity for detecting thin white matter in the developing brain[15]. The brain was divided into cerebral hemispheres, cerebellar hemispheres, and brainstem via Adaptive Disconnection[16]. Each cerebral hemisphere mask was subtracted from a sulcal mask generated by BrainVisa and recombined with the original FSL segmentation to remove all sulcal CSF voxels. The final hemisphere mask was reconstructed into a smoothed, 3-dimensional mesh in BrainVisa to obtain surface measures[17].

Gene Expression and Data Processing

RNA was assayed at Scripps Genomic Medicine (La Jolla, Calif., USA) for labeling, hybridization, and scanning using expression BeadChips pipeline (Illumina, San Diego, Calif., USA) per the manufacturer's instruction. All arrays were scanned with the Illumina BEADARRAY READER and read into Illumina GENOMESTUDIO software (version 1.1.1). Raw data was exported from Illumina GENOMESTUDIO and data pre-processing was performed using the lumi package[18] for R (R-project.org) and Bioconductor (bioconductor.org)[19].

Several quality criteria were used to exclude low quality arrays as previously described.[20,21] In brief, low-quality arrays were those with poor signal intensity (raw intensity box plots and average signal >2 standard deviations below the mean), deviant pair-wise correlation plots, deviant cumulative distribution function plots, deviant multi-dimensional scaling plots, or poor hierarchical clustering[22]. Five samples (four ASD and one Control) were identified as low quality due to poor detection rates, different distributions and curved dot plots, and were removed prior normalization.

Eighteen (18) samples had 1 replicate and all pair-wise plots of each replica had a correlation coefficient of 0.99. Hierarchical clustering of these replicated samples showed 13 samples having with the two replicas that clustered together, therefore the B array was arbitrarily chosen for the following steps. For the remaining 5 of these replicated samples, the two replicas did not cluster together, thus the averaged gene expression levels were used in the following steps. No batch effects were identified. Raw and normalized data is deposited in Gene Expression Omnibus (GSE42133). BrB-array filtering Tool was used to obtain a final set of genes without missing expression values. Filtering criteria were Log Intensity Variation (P>0.05) and percent missing (>50% of subjects). 142 final samples/arrays (87 ASD, 55 control), and thus 142 unique subject datasets, were deemed high quality and entered the expression analysis. Inter-array correlation (IAC) was 0.983.

Differentially expressed genes (DE; P<0.05) were obtained by class comparison (ASD versus control) in BRB-Array Tool using a random variance model. The DE genes from the discovery toddlers was then used to identify differentially expressed pathways (Metacore) and a potential gene expression signature of ASD. The latter one was then validated on the replication toddlers. Both discovery and replication datasets underwent the same filtering and normalization steps.

WGCNA and Association Analyses

Weighted Gene Correlation Network Analysis (WGCNA) package[23,24] was used to identify functional associations between gene modules and neuroanatomic measures across all discovery subjects. Co-expression analysis was run by selecting the lowest power for which the scale-free topology fit index reached 0.90 and by constructing a signed (i.e., bidirectional) network with a hybrid dynamic branch cutting method to assign individual genes to modules[25]. Gene Significance (GS; absolute value of the correlation between gene expression levels and neuroanatomical measure) and Module Membership (MM; measure of intramodular connectivity or co-expression across genes within each biologically relevant module) were also computed using WGCNA. GS versus MM was computed to provide a measure of gene activity patterns change between ASD and control groups (See, labs.genetics.ucla.edu/horvath/CoexpressionNetwork/Rpackages/WGCNA/) for manuals and further details. To identify gene-brain associations within each study group separately, the WGCNA analyses were also performed within ASD and control groups of the discovery sample.

Hypergeometric and Venn Analyses

Hypergeometric distribution analysis was performed using the function sum(dhyper( )) in R. The total number of human genes from which random gene-sets of equal size were taken to test the significance of the identified gene-sets were: 21,405 for the enrichment analyses (this number represents all genes annotated in the Metacore database), 20,151 for the Venn analyses involving the DE genes and gene modules (this number represents all genes passing the pre-processing analysis of the discovery study) and 26,210 for the Venn analysis of the CNV gene-content (this number represents all refseq human genes currently mapped and present on the Illumina platform HumanHT-12v4). The number of unique genes within autism relevant CNV below 1 Mb in size was 4611 and was obtained from the analysis of the AutDB database (see, mindspec.org/autdb.html). Only cases strictly annotated as ASD with/without additional features (for examples: mental retardation, neurocognitive impairment) were selected. Cases annotated as intellectual disability, developmental delay, language delay Asperger syndrome, broad spectrum autism, bipolar disorder, learning disability even if associated with autistic features, were not selected. Only CNVs from the UCSC build 36 (Human Genome 18) were selected. Venn analysis was performed using the online tool at pangloss.com/seidel/Protocols/venn.cgi.

Classifier and Performance Analysis

Twelve module eigengenes were obtained from the WGCNA analysis of the 2765 DE genes in the discovery sample. Identification of the four modules was based on AUC performance after logistic regression in the same sample. The pair of modules that best performed in distinguishing ASD from control subjects was identified. Next, whether adding each single extra module would increase or decrease performance was tested and if performance increased that module was retained. The four modules (blue, black, purple and greenyellow) displayed the best AUC performance and were used to independently validate the classifier.

To validate the classifier gene-weights were calculated from the genes of the selected modules using their correlation with the eigengene values. Weights were applied to the gene expression levels of each replication subject and eigengenes were computed and used in the logistic regression to independently validate the classification performance. Clinical and MRI characteristics between the correctly classified and misclassified groups (ASD and control) were compared to determine if the classifier was sensitive to these measures. Results for the Mullen, ADOS, and Vineland scores were compared. Residual brain volumes for total brain volume, cerebral white and grey matter, and cerebellar white and grey matter were also compared.

TABLE 26

Pearson and Spearman correlations of module-eigengenes and diagnosis (Dx)

| MODULE | Dx | Top Network |
|---|---|---|
| Green | −0.18*/ns | Inflammation_interferon signaling |
| Black | 0.24**/0.2^ | Translation_Translation initiation |
| Magenta | −0.24**/−0.25^^ | ns |
| Purple | −0.26**/−0.32^^^ | Cell cycle_Meiosis |
| Salmon | −0.39***/−0.4^^^ | ns |
| MidnightBlue | 0.18*/0.18^ | Cell adhesion_integrin-mediated |
| LightCyan | −0.37***/−0.34^^^ | ns |
| DarkRed | −0.2*/−0.20^ | ns |

Signif. codes: p-value Pearson
***<0.001;
**<0.01;
*<0.05; p-value Spearman
^^^<0.001;
^^<0.01;
^<0.05;
ns = not significant enrichment

REFERENCES

1. Wetherby A M, Allen L, Cleary J, Kublin K, Goldstein H. Validity and reliability of the communication and symbolic behavior scales developmental profile with very young children. Journal of speech, language, and hearing research: JSLHR 2002; 45:1202-18.
2. Pierce K, Carter C, Weinfeld M, et al. Detecting, studying, and treating autism early: the one-year well-baby check-up approach. The Journal of pediatrics 2011; 159:458-65 e1-6.
3. Luyster R, Gotham K, Guthrie W, et al. The Autism Diagnostic Observation Schedule-toddler module: a new module of a standardized diagnostic measure for autism spectrum disorders. Journal of Autism and Developmental Disorders 2009; 39:1305-20.

4. Chawarska K, Klin A, Paul R, Macari S, Volkmar F. A prospective study of toddlers with ASD: short-term diagnostic and cognitive outcomes. J Child Psychol Psychiatry 2009; 50:1235-45.

5. Cox A, Klein K, Charman T, et al. Autism spectrum disorders at 20 and 42 months of age: stability of clinical and ADI-R diagnosis. J Child Psychol Psychiatry 1999; 40:719-32.

6. Kleinman J M, Ventola P E, Pandey J, et al. Diagnostic stability in very young children with autism spectrum disorders. J Autism Dev Disord 2008; 38:606-15.

7. Mullen E M. Mullen Scales of Early Learning. AGS ed. MN: American Guidance Service Inc.; 1995.

8. Sparrow S, Cicchetti D V, Balla D A. Vineland Adaptive Behavior Scales. Second Edition. Survey Forms Manual. Pearson Assessments 2005.

9. Association AP. Diagnostic and Statistical Manual of Mental Disorders. Fourth Edition. American Psychiatric Association 2000.

10. Schroeder A, Mueller O, Stocker S, et al. The RIN: an RNA integrity number for assigning integrity values to RNA measurements. BMC Mol Biol 2006; 7:3.

11. Eyler L T, Pierce K, Courchesne E. A failure of left temporal cortex to specialize for language is an early emerging and fundamental property of autism. Brain 2012; 135:949-60.

12. Jenkinson M, Smith S. A global optimisation method for robust affine registration of brain images. Medical image analysis 2001; 5:143-56.

13. Smith S M. Fast robust automated brain extraction. Hum Brain Mapp 2002; 17:143-55.

14. Zhang Y, Brady M, Smith S. Segmentation of brain MR images through a hidden Markov random field model and the expectation-maximization algorithm. IEEE transactions on medical imaging 2001; 20:45-57.

15. Altaye M, Holland S K, Wilke M, Gaser C. Infant brain probability templates for MRI segmentation and normalization. NeuroImage 2008; 43:721-30.

16. Zhao L, Ruotsalainen U, Hirvonen J, Hietala J, Tohka J. Automatic cerebral and cerebellar hemisphere segmentation in 3D MRI: adaptive disconnection algorithm. Medical image analysis 2010; 14:360-72.

17. Rivière D G D, Denghien I, Souedet N, Cointepas Y. BrainVISA: an extensible software environment for sharing multimodal neuroimaging data and processing tools. NeuroImage 2009; 47:S163.

18. Du P, Kibbe W A, Lin S M. lumi: a pipeline for processing Illumina microarray. Bioinformatics (Oxford, England) 2008; 24:1547-8.

19. Gentleman R C, Carey V J, Bates D M, et al. Bioconductor: open software development for computational biology and bioinformatics. Genome Biology 2004; 5:R80.

20. Chow M L, Li H R, Winn M E, et al. Genome-wide expression assay comparison across frozen and fixed postmortem brain tissue samples. BMC genomics 2011; 12:449.

21. Chow M L, Pramparo T, Winn M E, et al. Age-dependent brain gene expression and copy number anomalies in autism suggest distinct pathological processes at young versus mature ages. PLoS Genet 2012; 8:e1002592.

22. Oldham M C, Konopka G, Iwamoto K, et al. Functional organization of the transcriptome in human brain. Nature Neuroscience 2008; 11:1271-82.

23. Langfelder P, Horvath S. WGCNA: an R package for weighted correlation network analysis. BMC Bioinformatics 2008; 9:559.

24. Langfelder P, Horvath S. Eigengene networks for studying the relationships between co-expression modules. BMC systems biology 2007; 1:54.

25. Pramparo T, Libiger O, Jain S, et al. Global developmental gene expression and pathway analysis of normal brain development and mouse models of human neuronal migration defects. PLoS Genet 2011; 7:e1001331.

Example 3

Age-Related Changes in Gene Expression in ASD and Non-ASD Controls

Figure 13A:
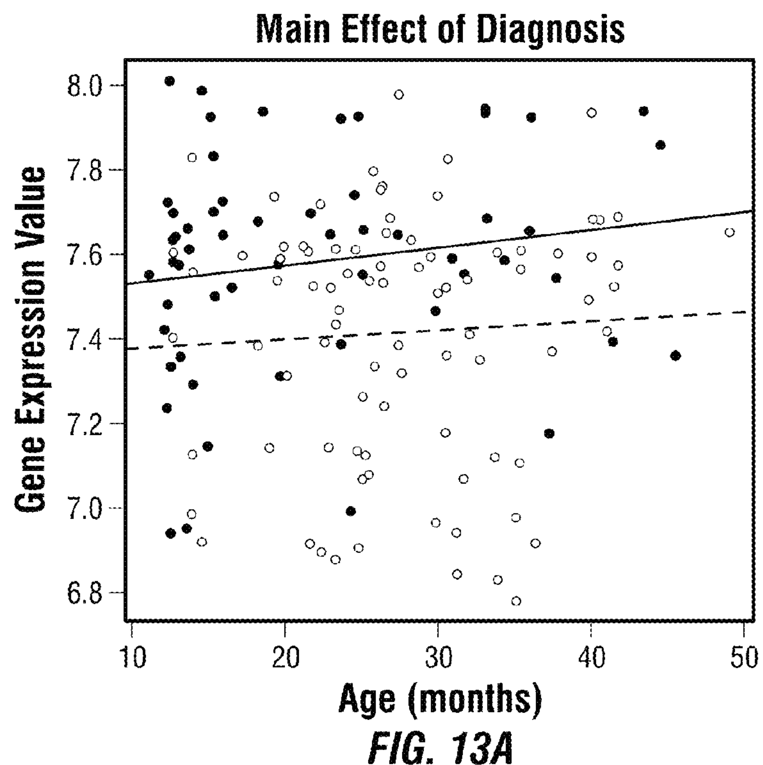
FIG. 13A-13C. Age- and diagnosis-related gene expression profiles.
Figure 13B:
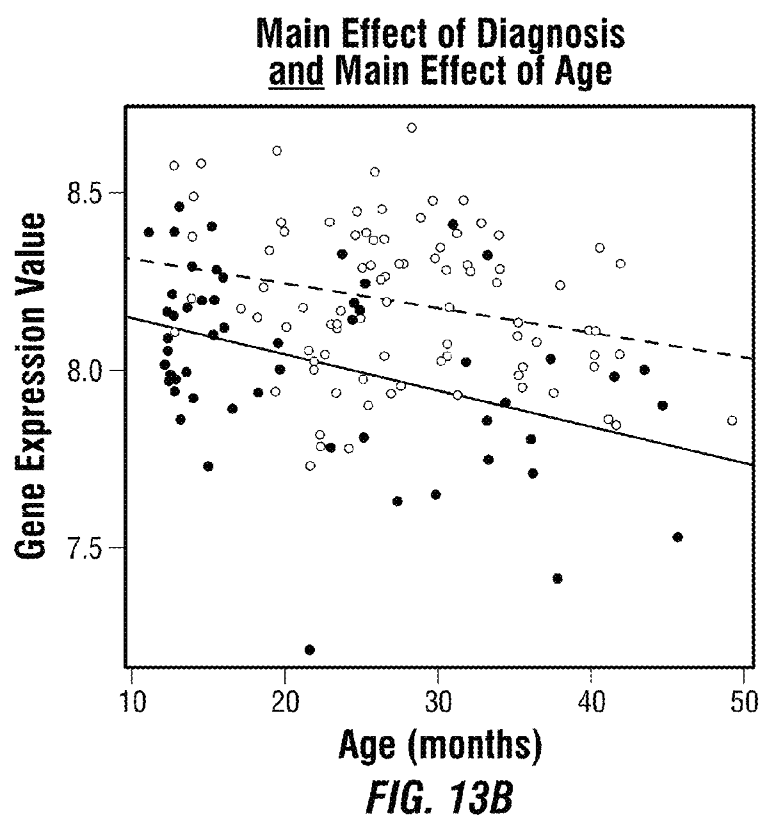
Figure 13C:
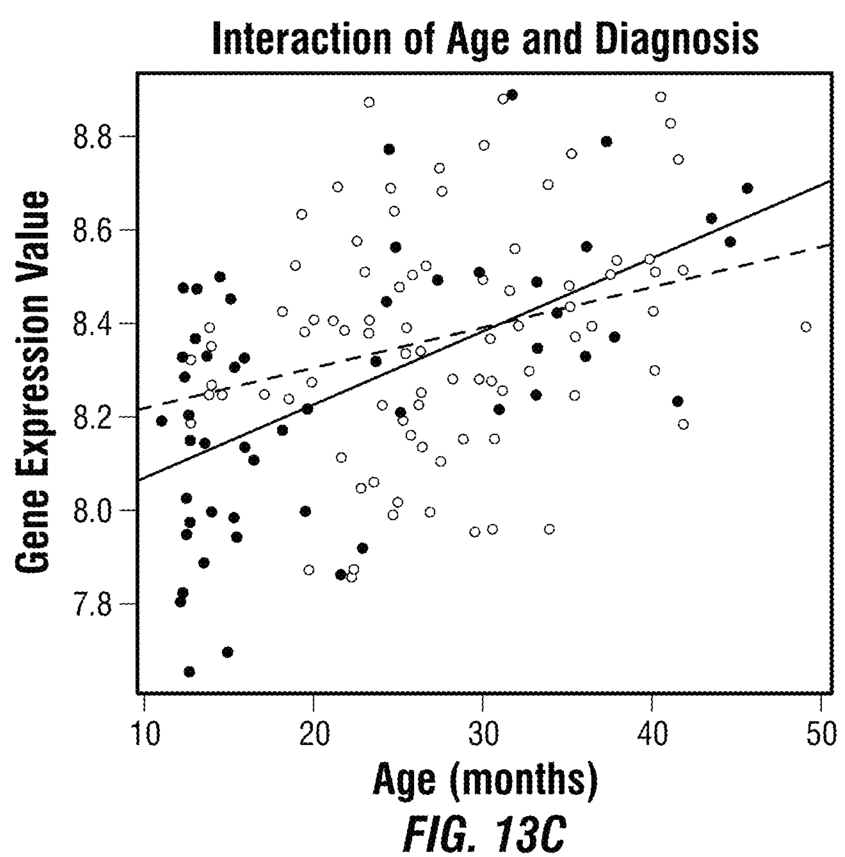

Age-related changes in ASD signature genes from infancy to young childhood were analyzed and compared to non-ASD controls. We discovered several patterns of age-dependent expression changes across ASD signature genes, including but not limited to the following three examples: First, genes were identified that showed main effects of diagnosis (ASD vs Control) and no statistically significant age-related changes (FIG. 13A; ASD—light grey vs Control—dark grey). For these genes (which are in the minority of all ASD signature genes), absolute expression level predicted diagnostic classification regardless of age at testing. Second, other genes were identified that showed main effects of diagnosis plus main effects of age (FIG. 13B); these represented a large portion of all ASD signature genes. Thus, for these genes knowledge of absolute expression level could give erroneous classification unless age at testing was taken into account. Third, still other signature genes were identified that showed an interaction between age and diagnosis (FIG. 13C) such that at some ages expression levels were greater in ASD than control, while at other ages expression levels did not significantly differ between ASD and control and at still other ages expression levels in controls exceeded ASD. A large portion of signature fell into this category of age-related change in gene expression level in ASD and controls. The age at which ASD and control expression change trajectories intersected varied across genes with some intersecting at early ages, others at 2-3 years and others after 2 to 3 years of age. For these genes, knowledge of absolute expression level will give completely erroneous classification unless age at testing is computationally taken into account.

Figure 14B:
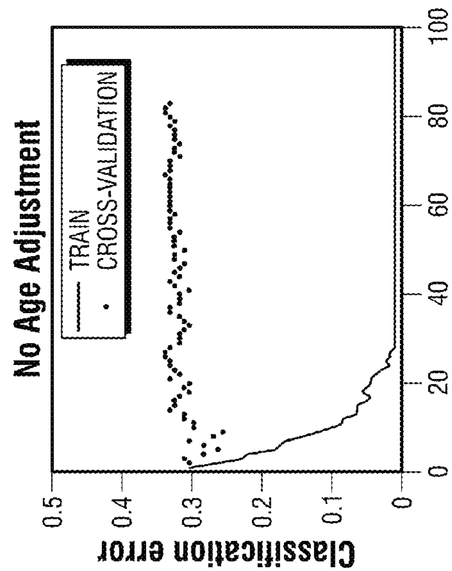
FIGS. 14A-14B. Inclusion of age in the classification analysis using Boosting.
Figure 14A:
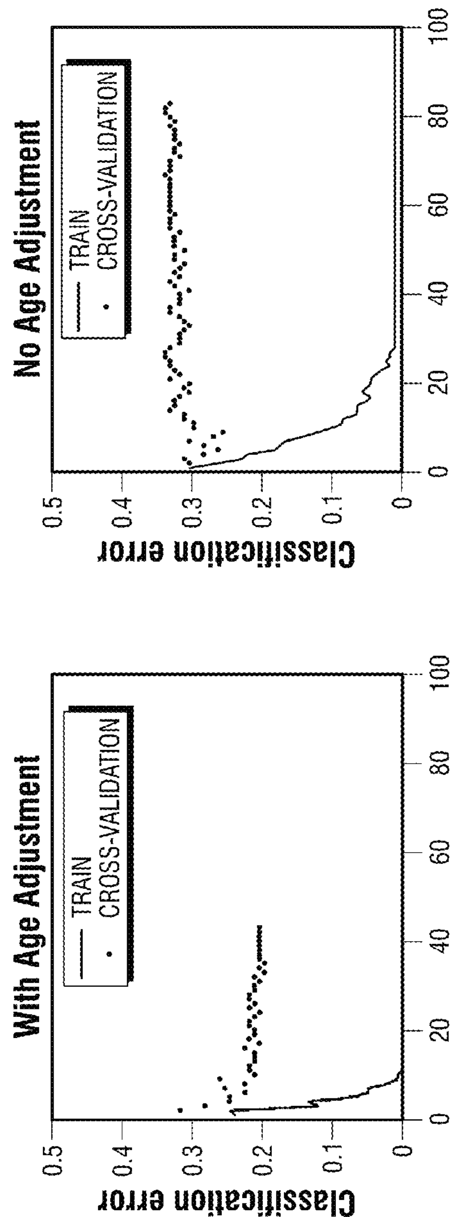

Knowledge we developed of these age-dependent changes in the expression levels of each and every signature gene is incorporated into the WGERD and is computationally combined with the weighted-gene expression values so that, with age changes as a predictor for each gene, we have optimized age-specific signatures of ASD. Given the child's age at the time of bioassay and the expression levels of each gene, the program calculates age-adjusted weight-gene expression values for the child to compare to the WGERD age-adjusted weight gene expression signature. Using different numbers of signature genes (ie, 10, 20, 40, 80, 160, etc) age-adjusted expression signatures out-perform expression signatures without any age correction by 4% to 10%. See FIG. 14 for one example of the invention's performance enhancement when knowledge of age effects is combined with gene expression (FIG. 14*a*) versus when age-adjusted calculations per gene are not used (FIG. 14*b*) as well as Table 3 above.

Example 4

Weighted Gene Expression Values in Combination with GeoPref Test Score

The magnitude of the problem articulated above in the Background section is substantial and immediate: Given the current prevalence rates, every year 52,000 and 84,000 babies born will go on to develop ASD. Therefore, there is an immediate need for feasible, practical, cost-effective and clinical-effective biological ASD tests that reduce the age of accurate and specific detection, evaluation, and referral to as young an age as possible in real world community settings. Procedures that have poor ASD specificity worsen the problem. Procedures that lack sensitivity leave a huge number of babies under-detect and un-diagnosed, which also fails to address the magnitude of the problem. Tests that are expensive, such as whole genome sequencing fail to address the problem because they are so expensive.

In brief, prior methods have not delivered screening, detection and diagnostic evaluation approaches that are easy, quick, and cost-effective to implement in ordinary community settings anywhere and by staff ordinarily present in the clinics. Missing from these methods is high ASD-specificity and very good sensitivity so that a large portion of all true cases of babies, 1 to 2 year olds, 2 to 3 year olds, and 3 to 4 year olds with ASD are detected and correctly diagnosed and a minimum percentage of non-ASD babies are not falsely misdiagnosed as ASD.

The methods of the invention provide the first procedure with a surprisingly high level of specificity and very good sensitivity in an easy, quick and cost-effective way. In some embodiments, the invention does this by using a novel method that combines gene expression as described above and GeoPref test data and signatures in the MMSM.

The GeoPref Test is fully described in Pierce et al. (2011). In brief, the GeoPref Test is a simple and quick 1-minute eye-tracking test that can be administered as a screen or evaluation test to individuals in the general pediatric population. Babies, infants, toddlers and young children are shown a computer screen that displays colorful moving patterns on one side (the "Geo" side) and lively moving children on the other (the "Social" side). Eye-tracking and scoring of how much time a child looks at one side or the other is automated. A child that looks at the "Geo" side by more than a threshold amount of time during a 1-minute test is considered a Geo preference (or "GeoPref") responder. GeoPref responders among babies, infants, toddlers and young children have a 99% chance of being ASD but only 20 to 30% of all ASD cases are detected by this test.

By computationally combining the weighted gene expression values and GeoPref score of a child, a gene expression-GeoPref signature of the child is obtained, and comparing it to the MMSM reference database compute a score for that child's ASD risk is computed based on divergence of the child's GeoPref MMSM signature to the GeoPref MMSM reference database. In one embodiment of this procedure, accuracy remains at 85% and sensitivity drops slightly to 72%, but ASD-specificity is a 98%. This is the highest overall performance of any previous biological or biobehavioral ASD test applied at any age from birth to 4 years. Importantly, this combined WGSM/MMSM signature is capable of very high beneficial impact in screening and diagnostic evaluation because it not only detects a very large portion of the general pediatric ASD population at young ages via a simple, quick 1 minute test plus ordinary blood draw to get a gene expression bioassay, but it has an extremely high correct detection rate and a very low false positive rate. Thus, it addresses in a very meaningful way the need for early and correct detection and diagnostic determination of ASD among the 52,000 to 84,000 babies born every year in the US who do develop ASD.

REFERENCES

1. Pierce, K., Conant, D., Hazin, R., Stoner, R. & Desmond, J. Preference for geometric patterns early in life as a risk factor for autism. *Archives of General Psychiatry* 68, 101-9 (2011).

Example 5

Weighted Gene Expression Values in Combination with Protein Signatures of ASD

ASD and other diseases are manifested by changes in gene expression, metabolite profiles and in the expression, post-translational processing and protein and small molecule interactions among the cellular and non-cellular constituents of blood and other tissues. There is wide variation in the correlation between gene expression and the level of any particular protein or modified variant thereof. These variations in the levels of particular proteins and protein variants have been found to correlate with disease and disease progression in numerous examples. Additionally, the poor correlation between gene expression and patterns of relative abundance of protein variants suggests that production of protein variants is subject to different aspects of disease biology than is gene expression, and further suggests that measurement of patterns of protein variants in blood and other tissues could be a valuable adjunct assessment of disease in combination with weighted gene expression.

Therefore, in certain embodiments, MMSM includes, but is not limited to, assays of proteins in peripheral blood. As with RNA tests, only a subset of blood proteins are likely to change in ways that allow their measurement to be informative for diagnosing autism. Simple changes in the abundance of certain proteins may be correlated with ASD, and measurement of the concentration of one or more of these proteins either directly in blood or extracted from blood can have diagnostic value. Useful measurement techniques span a range of specificity and technical approaches. Highly specific measurement of proteins derived from specific unique genes can use antibody reagents to specifically quantify particular protein species. The same approach can be extended to analyze large numbers of different proteins using collections of antibodies targeting the detection of multiple different protein species to enable the measurement of the abundance of larger groups of proteins in blood. For diagnostic assays, each of the antibodies would be chosen to recognize species of proteins that vary in abundance or protein quality as a function of ASD status, and this relationship to ASD would be established by experiment. Analogous to the weighted gene signatures used in the development of our diagnostic RNA signature, measurement of the weighted expression signature of multiple proteins can also be used to combine the ASD related changes in these proteins into a molecular fingerprint of ASD. An extension of this approach to use simple abundance measurements as a weighted diagnostic signature is to find and use ASD-associated changes in other protein properties to use as diagnostic molecular signatures. In addition to abundance measurement, these other informative changes include changes in protein post-translational modification, protein three dimensional conformation, complex formation with other serum components (other protein or non-protein components of blood) and changes in the ability to interact with ligands (e.g. protein or small molecules that can bind the proteins changed by ASD). Assays to discover these ASD changes in protein abundance or properties can also be incorporated directly or indirectly into diagnostic assays.

Protein signatures of ASD can be discovered by a large number of combinations of fractionation and analysis techniques. Whole blood proteins may be directly analyzed (for example using ForteBio Octet or other immunodetection systems), or the cellular and non-cellular fractions can be separated and separately analyzed with variable levels of fractionation of both cellular and plasma fractions. In general, analysis of proteins within a fraction becomes easier as the fraction is reduced in complexity by fractionation, but some analytical techniques can work directly on unfractionated or less fractionated samples. There is a long history of development of new protein extraction and fractionation techniques applied to research and commercial fractionation, purification and analysis of proteins to answer research questions or produce protein products. In general, proteins can be fractionated by solubility (e.g. by ammonium sulfate fractional precipitation, or by partitioning between solvents of differing composition), by selecting for particular binding affinity for functionalized surfaces (e.g. selecting for protein fractions with differing affinity for ion exchange or reverse phase matrices in HPLC, or for other more specific affinity reagents such as antibodies coupled to solid phase substrates or small molecule derivatized surfaces) or by selecting for specific migration characteristics in sieving matrices (e.g. size exclusion chromatography or electrophoresis). The affinity reagents used to capture and quantify specific protein species can be general (binding to all variants of a protein product of a particular gene), or the reagents could be specific for particular variants derived by post-translational processing, conformational change or liganding (e.g. antibodies specific for post-translationally modified forms of a protein). Once separated, the proteins can be analyzed by a number of techniques to identify and quantify particular proteins. Those skilled in the art would use mass spectrometry to define the genetic identity and quantity of intact or fragmented proteins within a mixture, or would use antibody or other specific affinity reagents to quantify these proteins.

As an example, we explored for protein biomarkers of ASD by doing immunoassays for the following 9 biomarkers: TNF-α, IL-6, IL-10, IP-10, sIL-6R, sFas, VEGF, sVEGFR-1 and tPAI-1 in serum samples derived from the following collection of 142 pediatric patients presenting for clinical assessment of ASD status.

| All | Typical | Language Delayed (LD) | ASD |
|---|---|---|---|
| 142 | 66 | 27 | 49 |

The results of this analyses suggested that abnormalities in levels of sFas (elevated) and, VEGF, sIL-6R, and IL-6 (all reduced) are significantly associated with ASD relative to TD patients. This demonstrates that there are multiple protein biomarkers of ASD, and integration of measurements of these protein changes into combination tests for ASD (e.g. combining weighted gene expression signatures, behavioral tests and measurements of blood protein composition) is expected to enhance the overall test performance. Extending this discovery approach to larger and more complex patient sets and to the use of additional combinations of fractionation, detection and protein identification will expand this list of diagnostically relevant protein changes, and choosing which tests to incorporate into combined assays is determined by prospective clinical trials as with the initial discovery of the weighted gene expression signatures. These results are a proof of principle demonstration that serum expression levels of proteins and protein variants can change as a function of ASD status, and that measurement of these levels can therefore be used as additional diagnostic assays in conjunction with WGSM in MMSM.

Other embodiments and uses are apparent to one skilled in the art in light of the present disclosures. Those skilled in the art will appreciate that numerous changes and modifications can be made to the embodiments of the invention and that such changes and modifications can be made without departing from the spirit of the invention. It is, therefore, intended that the appended claims cover all such equivalent variations as fall within the true spirit and scope of the invention.

We claim:

1. A method of conducting a weighted gene and feature test of autism (WGFTA) for autism screening, diagnosis or prognosis, comprising:

a) measuring gene expression levels for a subject for a group of genes consisting of at least 80 or more genes, wherein at least 20 or more genes are selected from each of the four gene sets listed in Tables 1.1 through 1.4 with absolute weight values ranging from about 0.50 to about 1.00 to form a set of raw gene expression data;

b) normalizing the gene expression level for each gene in the set of raw gene expression data to form a set of normalized gene expression data;

c) determining weighted gene expression levels for each gene in the set of normalized gene expression data using gene-specific weights from a reference autism weighted gene signature matrix (WGSM) to generate a set of weighted gene expression data, wherein the gene-specific weights are adjusted based on an age of the subject; and d) determining for the subject a risk, diagnosis, or prognosis of autism by comparing a divergence of the set of weighted gene expression data to reference gene expression data from the reference autism WGSM.

2. The method of claim 1, wherein the reference autism weighted gene signature matrix (WGSM) is derived from gene expression data from at least 40 healthy individuals and 40 autistic individuals.

3. The method of claim 1, wherein the at least 20 or more genes are involved in cell cycle, protein folding, cell adhesion, translation, DNA damage response, apoptosis, immune/inflammation functions, signal transduction ESR1-nuclear pathway, transcription-mRNA processing, cell cycle meiosis, cell cycle G2-M, cell cycle mitosis, cytoskeleton-spindle microtubule, and cytoskeleton-cytoplasmic microtubule functions.

4. The method of claim 1, wherein the determining for the subject the risk, diagnosis, or prognosis of autism further comprises comparing a divergence of a gene-network signature matrix (GNSM) of the subject to a reference autism GNSM wherein each said GNSM comprises interaction patterns of specific gene-weights and features calculated from gene-to-gene interactions, and wherein said interaction patterns are calculated based on the relationship or state of a gene with non-genomic features.

5. The method of claim 1, wherein the determining for the subject the risk, diagnosis, or prognosis of autism further comprises comparing a divergence of a multi-modal signature matrix (MMSM) of the subject to a reference autism MMSM wherein each said MMSM contains a quantification of non-genomic features obtained by clinical, behavioral, anatomical, and functional measurements.

6. The method of claim 5, wherein said non-genomic features comprise age, a GeoPreference test, a MRI test, a fMRI test, a DTI test, an Autism Diagnostic Observation Schedule (ADOS) test, or a Communication and Symbolic Behavior Scales (CSBS) test.

7. The method of claim 6, wherein said non-genomic feature is age.

8. The method of claim 1, wherein the determining for the subject the risk, diagnosis, or prognosis of autism further comprises comparing a divergence of a collateral feature signature matrix (CFSM) of the subject to a reference autism CFSM, wherein each said CFSM comprises analytes in maternal blood during pregnancy, a sibling with autism, or maternal genomic signature or preconditions.

9. The method of claim 1, wherein the group of genes consists of at least 160 or more genes, wherein at least 40 or more genes are selected from each of the four gene sets listed in Tables 1.1 through 1.4.

10. The method of claim 1, wherein the group of genes consists of up to 200 genes, wherein 50 genes are selected from each of the four gene sets listed in Tables 1.1 through 1.4.

* * * * *

UNITED STATES PATENT AND TRADEMARK OFFICE
CERTIFICATE OF CORRECTION

PATENT NO. : 10,002,230 B2
APPLICATION NO. : 14/604834
DATED : June 19, 2018
INVENTOR(S) : Eric Courchesne et al.

It is certified that error appears in the above-identified patent and that said Letters Patent is hereby corrected as shown below:

In the Specification

Column 1, Lines 17-20, please replace the paragraph under the STATEMENT REGARDING FEDERALLY SPONSORED RESEARCH from "This invention was made with government support under grant Nos. P50-MH081755, R01-MH080134, and R01-MH036840 awarded by National Institute of Mental Health (NIMH). The government has certain rights in the invention." to --This invention was made with government support under MH036840, MH080134, and MH081755 awarded by the National Institutes of Health. The government has certain rights in the invention.--

Signed and Sealed this
Second Day of December, 2025

John A. Squires
*Director of the United States Patent and Trademark Office*